United States Patent
Snow et al.

(10) Patent No.: US 6,489,328 B2
(45) Date of Patent: Dec. 3, 2002

(54) HETEROCYCLIC COMPOUNDS USEFUL AS INHIBITORS OF TYROSINE KINASES

(75) Inventors: Roger John Snow, Danbury, CT (US); Donghong A. Gao, Hopewell Junction, NY (US); Daniel R. Goldberg, Redding, CT (US); Abdelhakim Hammach, Danbury, CT (US); Daniel Kuzmich, Danbury, CT (US); Tina Marie Morwick, New Milford, CT (US); Neil Moss, Ridgefield, CT (US); Anthony S. Prokopowicz, III, Stormville, NY (US); Robert D. Selliah, Malden, MA (US); Hidenori Takahashi, LaGrangeville, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/921,510

(22) Filed: Aug. 2, 2001

(65) Prior Publication Data

US 2002/0119975 A1 Aug. 29, 2002

Related U.S. Application Data

(60) Provisional application No. 60/224,724, filed on Aug. 11, 2000.

(51) Int. Cl.$^7$ ..................... C07D 487/04; A61K 31/505
(52) U.S. Cl. .................. 514/252.16; 514/267; 544/250; 544/251
(58) Field of Search ............................. 544/250, 251; 514/252.16, 267

(56) References Cited

U.S. PATENT DOCUMENTS

| | | | |
|---|---|---|---|
| 4,176,184 A | 11/1979 | Austel et al. | .......... 424/248.52 |
| 5,646,153 A | 7/1997 | Spada et al. | ................ 514/259 |

FOREIGN PATENT DOCUMENTS

| | | |
|---|---|---|
| EP | 0 322 746 A1 | 7/1989 |
| WO | WO 98 28281 A1 | 7/1998 |
| WO | WO 98 54157 A1 | 12/1998 |
| WO | WO 99 24035 A1 | 5/1999 |

OTHER PUBLICATIONS

Simone, Oncology: Introduction, Cecil Textbook of Medicine, 20th Edition, vol. 1, pp. 1004–1010, 1996.*
Padmanabha, Et Al; "1–Methoxy–Agroclavine from Penicillium SP, WC 75209, A Novel Inhibitor of the LCK Tyrosine Kinase", Bioorganic & Medicinal Chemistry Letters 8 (1998) 569–574.*
Faltynek, Et Al; "Inhibition of T Lymphocyte Activation by a Novel p56lck Tyrosine Kinase Inhibitor"; J. Enzyme Inhibition, 1995, vol. 9, pp. 111–122.*
Hanke, Et Al, "Discovery of a Novel, Potent, and Src Family–selective Tyrosine Kinase Inhibitor"; Journal of Biological Chemistry, vol. 271, No. 2, 695–701, 1996.*
Bullington, Et Al; "The Development of Novel and Selective p56lck Tyrosine Kinase Inhibitors1"; Bioorganic & Medicinal Chemistry Letters 8 (1998) 2489–2494.*
Showalter, Et Al; "Small Molecule Inhibitors of the Platelet–Derived Growth Factor Receptor, the Fibroblast Growth Factor Receptor, and Src Family Tyrosine Kinases"; Pharmacol. Ther., vol. 76, Nos. 1–3, pp. 55–71, 1997.*
Traxler; "Protein tyrosine kinase inhibitors in cancer treatment"; Exp. Opin. Ther. Patents, 1997, 7(6); 571–588.*
Traxler; "Tyrosine kinase inhibitors in cancer treatment (Part II)"; Exp. Opin. Ther. Patents, 1998, 8(12); 1599–1625.*
Schneller, Et Al; "Linear and Proximal Benzo–Separated Alkylated Xanthines as Adenosine–Receptor Antagonists"; J. Med. Chem.; 1989, 32, 2247–2254.*
Kumar, Et Al;"Possible Anthelmintic Agents: Syntheses of Various Imidazoquinazolinone Carbamates"; Indian J. Chem., 1981, vol. 20B, 1068–1071.*
Agarwal, Et Al "Segregation of Activity Profile in Benzimidazoles: Effect of Spacers at 5(6)–Position of Methyl Benzimidazole–2–carbamates[1]"; Z. Naturforsch. 48c, 1993, 829–838.*

* cited by examiner

Primary Examiner—Deepak R. Rao
(74) Attorney, Agent, or Firm—Robert P. Raymond; Philip L. Datlow; Alan R. Stempel

(57) ABSTRACT

Disclosed are novel compounds of formula (I):

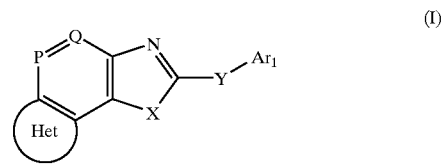

wherein Ar$_1$, X, Y, P, Q and Het are defined herein, which are useful as inhibitors of certain protein tyrosine kinases and are thus useful for treating diseases resulting from inappropriate cell proliferation, which include autoimmune diseases, chronic inflammatory diseases, allergic diseases, transplant rejection and cancer, as well as conditions resulting from cerebral ischemia, such as stroke. Also disclosed are pharmaceutical compositions comprising these compounds, processes for preparing these compounds and novel intermediate compounds useful in these processes.

21 Claims, No Drawings

HETEROCYCLIC COMPOUNDS USEFUL AS INHIBITORS OF TYROSINE KINASES

This application claims benefit from U.S. Provisional Application No. 60/224,724, filed Aug. 11, 2000, which is herein incorporated by reference in its entirety.

FIELD OF THE INVENTION

This invention relates to substituted compounds of formula (I):

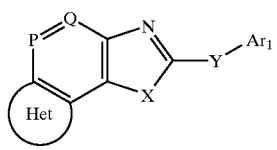

(I)

wherein $Ar_1$, X, Y, P, Q and Het are defined below, which are useful as inhibitors of certain protein tyrosine kinases and are thus useful for treating diseases resulting from inappropriate cell proliferation, which include autoimmune diseases, chronic inflammatory diseases, allergic diseases, transplant rejection and cancer, as well as conditions resulting from cerebral ischemia, such as stroke. This invention also relates to pharmaceutical compositions comprising these compounds, methods of using these compounds in the treatment of various diseases, processes for preparing these compounds and intermediate useful in these processes.

BACKGROUND OF THE INVENTION

Tyrosine kinases play an essential role in the regulation of cell signaling and cell proliferation by phosphorylating tyrosine residues of peptides and proteins. Inappropriate activation of tyrosine kinases is known to be involved in a variety of disease states, including immunologic and oncologic disorders.

It has been well established that T cells play an important role in regulating the immune response (F. Powrie and R. L. Coffman, *Immunol. Today*, 1993, 14, 270). Activation of T cells is often the initiating event in many inflammatory and autoimmune diseases. In addition to their role in immune surveillance, T cells can become autoreactive by recognizing self-antigens and thereby cause autoimmune disease such as rheumatoid arthritis and inflammatory bowel disease.

The T cell receptor (TCR) is the antigen-specific component of the T cell and is activated when the receptor is engaged with foreign or self-antigenic peptides. When the TCR is activated a series of enzyme-mediated signal transduction cascades is initiated which results in the production of pro-inflammatory cytokines such as interlukin-2 (IL-2). The release of IL-2 is critically important since this lymphokine is required for T-lymphocyte proliferation, differentiation, and effector function. Clinical studies have shown that interference with IL-2 activity effectively suppresses immune response in vivo (T. A. Waldmann, *Immunol. Today*, 1993, 14, 270). Accordingly, agents which inhibit T-lymphocyte activation and subsequent IL-2 production, or block the activity of IL-2 are therapeutically useful for selectively suppressing immune response in a patient in need of such immunosuppression.

The eight members of the src family of tyrosine kinases are src, lck, fyn, lyn, hck, fgr, blk and yes (J. B. Bolen, J. S. Brugge, *Ann. Rev. Immunol.*, 1997, 15, 371). These can be divided into 2 groups based on their pattern of tissue expression. Src, fyn and yes have a broad distribution while expression of lck, lyn, hck, fgr, and blk is largely limited to hemopoietic cells. The therapeutic effects of inhibiting kinases of the src family can be ascertained by linking functional defects seen in gene disruption studies in mice. Src(−/−) mice had severe abnormalities in bone remodeling. Inhibition of src may therefore be useful in treating osteoporosis. Lck(−/−) mice display a complete lack of CD4+ cells are unable to mount antigen-dependent immune responses.

A kinase of particular interest is p56lck, which is only expressed in T-cells. Within the TCR signal transduction cascade the tyrosine kinase p56lck is a required element to initiate the activation response from the TCR intracellular domains to other signaling proteins. For example, T cells which lack the p56lck protein are unable to signal through the T cell receptor (D. B. Straus and A. Weiss, *Cell*, 1992, 70, 585). Transfection of p56lck back into these cell lines restores TCR responsiveness. Also, it has been shown in mice that inactivation of the p56lck gene leads to lack of proper thymocyte development (T. J. Molina et al., *Nature*, 1992, 357, 161).

The conclusion drawn from these studies is that p56lck plays a crucial role in T cell maturation and antigen-induced T-cell activation. Therefore, an agent blocking p56lck would effectively block T cell function, act as an immunosuppressive agent and have potential utility in autoimmune diseases, for example rheumatoid arthritis, multiple sclerosis, lupus, transplant rejection and allergic diseases (J. H. Hanke et al., *Inflamm. Res.*, 1995, 44, 357).

Inhibitors of other members of the src family of non-receptor tyrosine kinases are also useful for treating various disease states. Src is present in osteoclasts, and is important in bone remodeling. For example, inactivation of p60src diminishes bone resorption by osteoclasts (P. Soriano et al., *Cell* 1991, 64, 693, B. F. Boyce et al. *J. Clin. Invest* 1992, 90, 1622), it is therefore possible that inhibitors of the kinase activity of p60src are useful in the treatment of osteoporosis, Paget's disease and inflammation of bones and joints.

Src kinases have been found to be activated in tumors, including breast and colon cancers, melanoma and sarcoma. For example, a number of primary tumors and tumor cell lines from patients with breast cancer, colon cancer, melanoma and sarcoma have been shown to have elevated src kinase activity, and activating src mutations are seen in some advanced colon cancers. Inhibitors of src kinase had significant antiproliferative activity against cancer cell lines (M. M. Moasser et al., *Cancer Res.*, 1999, 59, 6145) and inhibited the transformation of cells to an oncogenic phenotype (R. Karni et al., *Oncogene*, 1999, 18, 4654) suggesting that src kinase inhibitors may be useful anti-cancer agents.

Src inhibitors have also been reported to be effective in an animal model of cerebral ischemia (R. Paul et al. *Nature Medicine* 2001, 7, 222), suggesting that src kinase inhibitors may thus be useful in treating conditions involving cerebral ischemia. For example, src kinase inhibitors may be useful in reducing brain damage following stroke.

In addition, src family kinases participate in signal transduction in several cell types. For example, fyn, like lck, is involved in T-cell activation. Hck and fgr are involved in Fc gamma receptor mediated oxidative burst of neutrophils. Src and lyn are believed to be important in Fc epsilon induced degranulation of mast cells, and so may play a role in asthma and other allergic diseases. The kinase lyn is known to be involved in the cellular response to DNA damage induced by UV light (T. Hiwasa, *FEBS Lett.* 1999, 444, 173) or ionizing radiation (S. Kumar, *J. Biol Chem*, 1998, 273, 25654). Inhibitors of lyn kinase may thus be useful as potentiators in radiation therapy.

Platelet derived growth factor is a potent mitogen for smooth muscle cells. Its receptor (PDGFR) is a member of the receptor tyrosine kinase family (L. Claesson-Welsh, *J. Biol Chem*, 1994, 269, 32023). PDGF is involved in atherosclerosis and restenosis (K. E. Bomfeldt, *Trends Cardiovasc. Med.*, 1996, 6, 143). In addition, receptor tyrosine kinases including PDGFR kinase have been implicated as contributing factors in cancer (A. Levitzki and A. Gazit, *Science*, 1995, 267, 1782) including ovarian (M. B. Dabrow et al., *Gynecologic Oncology*, 1998, 71, 29) and prostate (S. M. Sintich et al., *Endocrinology*, 1999, 140, 3411) cancers and glioblastoma (B. J. Silver, *BioFactors*, 1992 3, 217). Inhibitors of PDGFR kinase are thus useful in the treatment of fibrotic diseases, restenosis and PDGF-dependent tumors.

Reports have appeared in the literature of agents that inhibit the kinase activity of p56lck kinase and thus inhibit T cell activation. These include the natural product lavendustin A, and analogs (M. S. Smyth, *J. Med. Chem.*, 1993, 36, 3010), the natural product damnacanthal (C. R. Faltynek et al., *Biochemistry*, 1995, 34, 12404), and a 1-methoxy agroclavine isolated from a fungal extract (R. Padmanabha et al. *Bioorganic and Med. Chem. Letters*, 1998, 8, 569). Other inhibitors reported include WIN 61651 (*J. Enzyme Inhibition*, 1995, 9, 111) pyrazolopyrimidines PP1 and PP2 (Hanke et al. *J. Biol Chem*, 1996, 271, 695) and indanone and indandione derivatives (J. L. Bullington et al., *Bioorganic and Med. Chem. Letters*, 1998, 8, 2489).

A. P. Spader et al. (WO 98/54157, 1998) describe quinoline and quinoxaline compounds that inhibit p56lck and PDGFR kinase. Fused polycyclic 2-aminopyrimidine derivatives that inhibit p56lck are reported by J. M. Davis et al. (WO 98/28281, 1998). J. Das et al. claim a series of benzothiazole amides as inhibitors of lck and other src family kinases (WO 99/24035, 1999). Inhibitors of PDGFR kinase and src-family kinases were reviewed by H. D. H. Showalter, A. J. Kraker, *Pharmacol. Ther.*, 1997, 76, 55. Several patents on inhibitors of lck are reviewed in P. M. Traxler, *Exp. Opin. Ther. Patents*, 1997, 7, 571, and P. M. Traxler, *Exp. Opin. Ther. Patents*, 1998, 8, 1599.

EP 322 746 A1 discloses heterocyclic lactam derivatives described as being useful as cardiotonic agents, antihypertensive agents and vasodilators.

Examples of tricyclic systems similar to formula (I) above are known, but not having the 2-amino substituents on the benzimidazole ring. See S. W. Schneller et al., *J. Med. Chem.*, 1989, 32, 2247. Examples of tricyclic systems similar to formula (I) with a carbamate at the 2-position have been reported in S. Kumar et al., *Indian J. Chem.* 1981, 20B, 1068 and S. Agarwal et al., *Z. Naturforsch. C*, 1993, 48, 829.

The compounds of the present invention represent a novel structural class, which is distinct from previously reported tyrosine kinase inhibitors.

BRIEF SUMMARY OF THE INVENTION

The work cited above supports the principle that inhibition of the kinases mentioned above will be beneficial in the treatment of various disease states.

It is therefore an object of the invention to provide novel compounds which inhibit PDGFR kinase and the src-family kinases including lck, src, fyn, lyn, hck, fgr, blk and yes.

It is a further object of the invention to provide methods for treating diseases and pathological conditions mediated by src-family tyrosine kinases and PDGFR kinase such as autoimmune diseases, transplant rejection, psoriasis, osteoporosis, Paget's disease, cancer, including src-dependent tumors and PDGF-dependent tumors, cerebral ischemic conditions, atherosclerosis, restenosis and allergic diseases, using the novel compounds of the invention.

It is yet a further object of the invention to provide processes of preparation of the above-mentioned novel compounds and pharmaceutical compositions comprising the same.

DETAILED DESCRIPTION OF THE INVENTION

The src-family tyrosine kinases and PDGFR kinase discussed above exhibit some homology in their amino acid structure. It is contemplated that due to structural differences between individual src-family kinases and PDGFR kinase, different compounds of the invention may have different inhibitory potencies against individual tyrosine kinases. Thus some of compounds of the invention may also be expected to be most effective in treating diseases mediated by tyrosine kinases that they inhibit most potently. Particular compounds disclosed herein have been shown to be active inhibitors of p56lck kinase, p60src kinase and PDGFR kinase. See the section entitled "Assessment of Biological Properties" disclosed herein.

In its broadest generic aspect, the invention provides novel compounds of the formula (I) below:

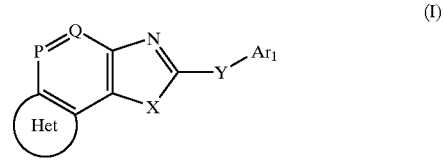

(I)

wherein:

Ar$_1$ is an aromatic or nonaromatic carbocycle, heteroaryl or heterocycle; wherein said carbocycle, heteroaryl or heterocycle is optionally substituted by one or more R$_1$, R$_2$ and R$_3$;

X is NH, N—C$_{1-3}$alkyl, N-cyclopropyl, S or O;

Y is NR$_{13}$;

R$_1$ and R$_2$ are the same or different and are selected from H, halogen, CN, NO$_2$, C$_{1-10}$ branched or unbranched saturated or unsaturated alkyl, C$_{1-10}$ branched or unbranched alkoxy, C$_{1-10}$ branched or unbranched acyl, C$_{1-10}$ branched or unbranched acyloxy, C$_{1-10}$ branched or unbranched alkylthio, aminosulfonyl, di-(C$_{1-3}$) alkylaminosulfonyl, NR$_8$R$_9$, aryl, aroyl, aryloxy, arylsulfonyl, heteroaryl and heteroaryloxy; wherein the abovementioned R$_1$ and R$_2$ are optionally partially or fully halogenated or optionally substituted with one to three groups independently selected from the group consisting of oxo, OH, NR$_8$R$_9$, C$_{1-6}$ branched or unbranched alkyl, C$_{3-7}$cycloalkyl, phenyl, naphthyl, heteroaryl, aminocarbonyl and mono- or di(C$_{1-3}$) alkylaminocarbonyl;

R$_3$ is selected from the group consisting of H, halogen, OH, (CH$_2$)$_n$NR$_8$R$_9$, (CH$_2$)$_n$CO$_2$R$_{10}$, C$_{1-3}$alkyl optionally substituted with OH, C$_{1-3}$ alkoxy optionally halogenated and C$_{1-3}$ alkylthio;

Het represents a fused heterocyclic ring having a formula A, B or C:

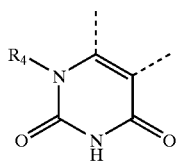

A

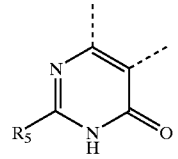

B

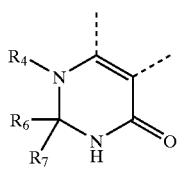

C $R_4$ is selected from H, $C_{1-6}$ alkyl branched or unbranched, saturated or unsaturated, and optionally substituted with phenyl, OH or $C_{1-3}$alkoxy, $C_{3-10}$-cycloalkyl, or $C_{5-8}$cycloalkenyl; or $R_4$ is selected from $(CH_2)_m NR_8 R_9$, $(CH_2)_m NR_8 COR_{10}$, $(CH_2)_n CO_2 R_{10}$, $(CH_2)_n CONR_8 R_9$, phenyl, heteroaryl or heterocycle, each phenyl, heteroaryl or heterocycle being optionally substituted with $C_{1-3}$alkyl, $C_{1-3}$alkoxy, $(CH_2)_m NR_8 R_9$, OH, $SO_3 H$ or halogen;

$R_5$ is selected from H, $C_{1-10}$alkyl branched or unbranched, $C_{3-10}$ cycloalkyl, $C_{5-7}$cycloalkenyl, $C_{2-6}$ alkenyl, $C_{2-6}$ alkynyl, $C_{1-6}$acyl, each being optionally substituted with one or more halogen, OH, oxo, CN, $C_{1-6}$alkyl, $C_{2-6}$ alkenyl, $C_{2-6}$ alkynyl, $C_{1-3}$alkoxy, $NR_8 R_9$, ureido, guanidino, $NR_8 COR_{10}$, $SR_{10}$, $CONR_8 R_9$, $CO_2 R_{10}$, $C_{3-10}$ cycloalkyl $C_{3-10}$cycloalkylidene, $C_{5-7}$cycloalkenyl, aryloxy, arylthio, aryl, heteroaryl or heterocycle; wherein each of $C_{1-6}$alkyl, $C_{2-6}$ alkenyl, $C_{2-6}$ alkynyl, $C_{3-10}$cycloalkyl, $C_{3-10}$cycloalkylidene, $C_{5-7}$cycloalkenyl, aryloxy, arylthio, aryl, heteroaryl or heterocycle is optionally substituted with one or more $C_{1-3}$alkyl, $C_{1-3}$alkoxy, halogen, CN, $NO_2$, amidino, guanidino, $(CH_2)_n NR_8 R_9$, or $O(CH_2)_{2-4} NR_8 R_9$; wherein one or more of the amino nitrogens in the ureido, amidino or guanidino groups in this paragraph may be optionally substituted with $C_{1-3}$alkyl, phenyl$C_{0-3}$alkyl, $C_{1-3}$alkoxy or $CO_2 R_{10}$;

or $R_5$ is selected from $CO_2 R_{10}$, $NR_8 R_9$, $CONR_8 R_9$, aryl, heteroaryl, heterocycle, aryl-CO—, heteroaryl-CO— or heterocycle-CO—, wherein each aryl, heteroaryl or heterocycle is optionally substituted with one to three:

$C_{1-3}$alkoxy, halogen, $NO_2$, CN, $S(O)_p NR_8 R_9$, $C_{0-3}$alkylS$(O)_p$, $NR_8 R_9$, $(CH_2)_n CO_2 R_{10}$, $(CH_2)_n CONR_8 R_9$, $CO(CH_2)_n NR_8 R_9$, $O(CH_2)_{2-4} NR_8 R_9$, ureido, guanidino, cycloalkyl, aryl, heteroaryl, heterocycle, cycloalkyl-Z—, aryl-Z—, heteroaryl-Z—, heterocycle-Z—, or $C_{1-3}$alkyl optionally substituted with phenyl or $NR_8 R_9$, wherein Z is a bridging group selected from $C_{1-10}$ alkylene branched or unbranched, CO, $S(O)_p$, O, S, NH, CONH, NHCO, COO or OOC, and wherein each cycloalkyl, aryl, heteroaryl or heterocycle is optionally substituted with $NO_2$, $C_{1-3}$alkyl, $C_{1-3}$alkoxy, halogen, $CO_2 R_{10}$, $(CH_2)_n NR_8 R_9$, $O(CH_2)_{2-4} NR_8 R_9$, ureido or guanidino, wherein one or more of the amino nitrogens in the ureido or guanidino groups in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-12}$ bridged- or spiro-bicyclic ring system, optionally having one or two double bonds in the ring system, and wherein up to 3 carbon atoms in the ring system may be replaced by heteroatoms selected from N, O and S; and wherein said ring system may be optionally substituted with $C_{1-3}$alkyl, $C_{1-3}$alkoxy, halogen, $CO_2 R_{10}$, ureido, guanidino, amidino, $(CH_2)_n NR_8 R_9$, or $O(CH_2)_{2-4} NR_8 R_9$; wherein one or more of the amino nitrogens in the ureido, guanidino or amidino groups in this paragraph may be optionally substituted with $C_{1-3}$alkyl, phenyl$C_{0-3}$alkyl or $C_{1-3}$alkoxy;

$R_6$ is selected from H, $C_{1-6}$alkyl branched or unbranched, $C_{2-6}$ alkenyl branched or unbranched, $CO_2 R_{10}$, $C_{3-8}$cycloalkyl, $C_{3-8}$cycloalkenyl, aryl, aryl$C_{1-3}$alkyl, heteroaryl and heterocyclyl; wherein said $C_{1-6}$alkyl, $C_{2-6}$alkenyl, $C_{3-8}$cycloalkyl, $C_{3-8}$cycloalkenyl, aryl, aryl$C_{1-3}$alkyl, heteroaryl or heterocyclyl are optionally substituted with OH, $C_{1-3}$alkoxy, $C_{1-3}$acyloxy, $CO_2 R_{10}$, $NR_{11} R_{12}$, $O(CH_2)_{2-4} NR_{11} R_{12}$, aryl, heteroaryl or heterocyclyl;

$R_7$ is H or $C_{1-6}$alkyl;

$R_8$ and $R_9$ are the same or different and are each independently selected from H, OH, $CO_2 R_{10}$, $C_{1-10}$ acyl branched or unbranched, $C_{1-3}$alkoxy, $C_{1-6}$alkyl branched or unbranched, $C_{3-6}$alkenyl, $C_{3-8}$cycloalkyl, aryl, aryl$C_{1-3}$alkyl, aroyl, heteroaryl or heterocycle; wherein said alkyl, cycloalkyl, aryl, aryl$C_{1-3}$alkyl, aroyl, heteroaryl or heterocycle are optionally substituted with OH, $C_{1-3}$alkoxy, $C_{1-3}$acyloxy, $CO_2 R_{10}$, $NR_{11} R_{12}$, $O(CH_2)_{2-4} NR_{11} R_{12}$, aryl, or heteroaryl;

or $R_8$ and $R_9$ together form a 3–7 member alkylene chain completing a ring about the N atom to which they are attached; wherein said alkylene chain is optionally interrupted by O, $S(O)_p$, $NCOR_{10}$, $NCO_2 R_{10}$, $NR_{11}$ or $NC(=NR_{11})NR_{11} R_{12}$; and wherein said ring is optionally substituted by $C_{1-3}$ alkyl, $C_{1-3}$alkoxy, OH or —$(CH_2)_n NR_{11} R_{12}$;

$R_{10}$ is selected from H, $C_{1-6}$alkyl, $C_{3-8}$cycloalkyl, wherein each alkyl or cycloalkyl is optionally substituted with phenyl, OH, $C_{1-3}$alkoxy, $C_{1-3}$alkanoyloxy or $NR_{11} R_{12}$, or $R_{10}$ is phenyl optionally substituted with one to three $C_{1-3}$alkyl, $C_{1-3}$alkoxy, halogen, $(CH_2)_m NR_8 R_9$, $(CH_2)_n CONR_8 R_9$ or $O(CH_2)_{2-4} NR_8 R_9$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2 O(CH_2)_2$;

$R_{13}$ is H or $C_{1-3}$alkyl;

P and Q are each independently CH or N;

m is 1–4;

n is 0–3;

and p is 0–2;

wherein one or more of the primary amine or secondary amine nitrogen atoms in any of the $R_4$, $R_5$, $R_6$ and $R_7$ substituent groups may optionally be protected by a protecting group;

and the pharmaceutically acceptable derivatives thereof.

In one embodiment of the invention, there are provided compounds of the formula (I) as described above, and wherein:

$Ar_1$ is
- a) a cycloalkyl group selected from cyclopropyl, cyclobutyl, cyclopentanyl, cyclohexanyl and cycloheptanyl;
- b) a cycloalkenyl group selected from cyclopentenyl, cyclohexenyl, and cycloheptenyl;
- c) an aromatic carbocycle selected from phenyl, naphthyl, indanyl, indenyl, dihydronaphthyl, tetrahydronaphthyl or fluorenyl,
- d) a heteroaryl selected from pyridyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl,or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or
- e) a heterocycle selected from: pyrrolinyl, pyrrolidinyl, pyrazolinyl, pyrazolidinyl, piperidinyl, morpholinyl, thiomorpholinyl, pyranyl, thiopyranyl, piperazinyl and indolinyl;

wherein each of the above $Ar_1$ are optionally substituted by one or more $R_1$, $R_2$ and $R_3$;

$R_1$ and $R_2$ are as defined in claim 1, and $R_3$ is hydrogen, halogen, methyl, methoxy, hydroxymethyl or OH;

wherein each of the above $Ar_1$ are optionally substituted by one or more $R_1$, $R_2$ and $R_3$;

$R_1$ and $R_2$ are as defined in claim 1, and $R_3$ is H, halogen, methyl, methoxy, hydroxymethyl or OH;

$R_4$ is H, $C_{1-3}$alkyl branched or unbranched, saturated or unsaturated, and optionally substituted with OH; or $R_4$ is $(CH_2)_{2-3}NR_8R_9$, $(CH_2)_nCO_2R_{10}$ or $(CH_2)_nCONR_8R_9$;

$R_5$ is selected from H, $C_{1-10}$alkyl branched or unbranched, $C_{3-10}$ cycloalkyl, $C_{5-7}$cycloalkenyl, $C_{2-6}$ alkenyl, $C_{2-6}$ alkynyl, $C_{1-6}$acyl, each being optionally substituted with one or more halogen, OH, oxo, CN, $C_{1-6}$alkyl, $C_{2-6}$ alkenyl, $C_{2-6}$ alkynyl, $C_{1-3}$alkoxy, $NR_8R_9$, ureido, guanidino, $NR_8COR_{10}$, $SR_{10}$, $CONR_8R_9$, $CO_2R_{10}$, $C_{3-10}$ cycloalkyl, $C_{3-10}$cycloalkylidene, $C_{5-7}$cycloalkenyl, aryloxy, arylthio, aryl, heteroaryl or heterocycle; wherein each of $C_{1-6}$alkyl, $C_{2-6}$ alkenyl, $C_{2-6}$ alkynyl, $C_{3-10}$cycloalkyl, $C_{3-10}$cycloalkylidene, $C_{5-7}$cycloalkenyl, aryloxy, arylthio, aryl, heteroaryl or heterocycle is optionally substituted with one or more $C_{1-3}$alkyl, $C_{1-3}$alkoxy, halogen, CN, $NO_2$, amidino, guanidino, $(CH_2)_nNR_8R_9$, or $O(CH_2)_{2-4}NR_8R_9$; wherein one or more of the amino nitrogens in the ureido, amidino or guanidino groups in this paragraph may be optionally substituted with $C_{1-3}$alkyl, phenyl$C_{0-3}$alkyl, $C_{1-3}$alkoxy or $CO_2R_{10}$;

or $R_5$ is selected from $CO_2R_{10}$, $NR_8R_9$, $CONR_8R_9$, aryl, heteroaryl, heterocycle, aryl-CO—, heteroaryl-CO— or heterocycle-CO—, wherein each aryl, heteroaryl or heterocycle is optionally substituted with one to three: $C_{1-3}$alkoxy, halogen, $NO_2$, CN, $S(O)_pN_8R_9$, $C_{0-3}$alkylS$(O)_p$, $NR_8R_9$, $(CH_2)_nCO_2R_{10}$, $(CH2)_nCONR_8R_9$, CO$(CH_2)_nNR_8R_9$, $O(CH_2)_{2-4}NR_8R_9$, ureido, guanidino, cycloalkyl, aryl, heteroaryl, heterocycle, cycloalkyl-Z—, aryl-Z—, heteroaryl-Z—, heterocycle-Z—, or $C_{1-3}$alkyl optionally substituted with phenyl or $NR_8R_9$, wherein Z is a bridging group selected from $C_{1-10}$ alkylene branched or unbranched, CO, $S(O)_p$, O, S, NH, CONH, NHCO, COO or OOC, and wherein each cycloalkyl, aryl, heteroaryl or heterocycle is optionally substituted with $NO_2$, $C_{1-3}$alkyl, $C_{1-3}$alkoxy, halogen, $CO_2R_{10}$, $(CH_2)_nNR_8R_9$, $O(CH_2)_{2-4}NR_8R_9$, ureido or guanidino, wherein one or more of the amino nitrogens in the ureido or guanidino groups in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-12}$ bridged- or spiro-bicyclic ring system, optionally having one or two double bonds in the ring system, and wherein up to 3 carbon atoms in the ring system may be replaced by heteroatoms selected from N, O and S; and wherein said ring system may be optionally substituted with $C_{1-3}$alkyl, $C_{1-3}$alkoxy, halogen, $CO_2R_{10}$, ureido, guanidino, amidino, $(CH_2)_nNR_8R_9$, or $O(CH_2)_{2-4}NR_8R_9$; wherein one or more of the amino nitrogens in the ureido, guanidino or amidino groups in this paragraph may be optionally substituted with $C_{1-3}$alkyl, phenyl$C_{0-3}$alkyl or $C_{1-3}$alkoxy;

$R_6$ is selected from H, $C_{1-6}$alkyl branched or unbranched, $C_{2-6}$ alkenyl branched or unbranched, or $CO_2R_{10}$; wherein said $C_{1-6}$alkyl or $C_{1-6}$ alkenyl are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl, heteroaryl or heterocyclyl;

$R_7$ is H or $C_{1-6}$alkyl;

$R_8$ and $R_9$ are the same or different and are each independently selected from H, OH, $C_{1-3}$alkyl branched or unbranched, $CO_2R_{10}$, $C_{3-8}$cycloalkyl, phenyl, benzyl, benzoyl, heteroaryl or heterocycle; wherein said alkyl, cycloalkyl, phenyl, benzyl, benzoyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl;

or $R_8$ and $R_9$ together form a 3–7 member alkylene chain completing a ring about the N atom to which they are attached; wherein said alkylene chain is optionally interrupted by O, $S(O)_p$, $NCOR_{10}$, $NCO_2R_{10}$, $NR_{11}$ or $NC(=NR_{11})NR_{11}R_{12}$; and wherein said ring is optionally substituted by $C_{1-3}$ alkyl, $C_{1-3}$alkoxy, OH or —$(CH_2)_nNR_{11}R_{12}$;

$R_{10}$ is H or $C_{1-6}$alkyl optionally substituted with phenyl, OH, $C_{1-3}$alkoxy, $C_{1-3}$alkanoyloxy or $NR_{11}R_{12}$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$;

$R_{13}$ is H; and

P and Q are each CH.

In another embodiment of the invention, there are provided compounds of the formula (I) as described immediately above, and wherein:

$Ar_1$ is phenyl or pyridyl, each optionally subsituted by one or more $R_1$, $R_2$ and $R_3$;

X is NH or N—$C_{1-3}$alkyl;

Y is NH;

$R_1$ and $R_2$ are the same or different and selected from: halogen, $C_{1-3}$ alkyl, wherein the $C_{1-3}$ alkyl is optionally partially or fully halogenated, $NO_2$ or $NR_8R_9$;

$R_3$ is H, halogen, methyl or methoxy;

$R_4$ is H, $C_{1-3}$alkyl branched or unbranched, saturated or unsaturated, and optionally substituted with OH; or $R_4$ is $(CH_2)_{2-3}NR_8R_9$ or $CO_2R_{10}$;

$R_5$ is selected from H, $C_{1-3}$alkyl branched or unbranched, $C_{3-8}$ cycloalkyl, $C_{5-7}$cycloalkenyl or $C_{2-4}$ alkenyl, each being optionally substituted with one or more OH, CN, $NR_8R_9$, $CONR_8R_9$, $C_{3-8}$ cycloalkyl, $C_{5-7}$cycloalkenyl, phenyl, heteroaryl or heterocycle; wherein each phenyl, heteroaryl or heterocycle is optionally substituted with one or more $C_{1-3}$alkyl, $C_{1-3}$alkoxy, halogen, CN, $NO_2$, amidino, guanidino, $(CH_2)_nNR_8R_9$, or $O(CH_2)_{2-4}NR_8R_9$; wherein one or more of the amino nitrogens in the amidino or guanidino groups in this paragraph may be optionally substituted with $C_{1-3}$alkyl, phenyl$C_{0-3}$alkyl, $C_{1-3}$alkoxy or $CO_2R_{10}$;

or $R_5$ is selected from $CO_2R_{10}$, $NR_8R_9$, $CONR_8R_9$, phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl, or indolyl-CO—, wherein each phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl or indolyl-CO— is optionally substituted with one to three:

halogen, $NO_2$, $S(O)_pNR_8R_9$, $C_{0-3}$alkyl$S(O)_p$, $NR_8R_9$, $(CH_2)_nCO_2R_{10}$, ureido, guanidino, cycloalkyl, phenyl, heteroaryl, heterocycle, cycloalkyl-Z—, phenyl-Z—, heteroaryl-Z—, heterocycle-Z—, or $C_{1-3}$alkyl optionally substituted with phenyl or $NR_8R_9$, wherein Z is a bridging group selected from $C_{1-3}$ alkylene branched or unbranched, O, $S(O)_p$ or NH, and wherein each cycloalkyl, phenyl, heteroaryl or heterocycle is optionally substituted with $NO_2$, $C_{1-3}$alkyl, $C_{1-3}$alkoxy, $CO_2R_{10}$, $(CH_2)_nNR_8R_9$, $O(CH_2)_{2-4}NR_8R_9$ or guanidino, wherein one or more of the amino nitrogens in the guanidino group in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-7}$ bridged-bicyclic ring system, optionally having one or two double bonds in the ring system, and wherein up to 1 carbon atom in the ring system may be replaced by a nitrogen atom; and wherein said ring system may be optionally substituted with $C_{1-3}$alkyl, $C_{1-3}$alkoxy, halogen, $(CH_2)_nNR_8R_9$, or $O(CH_2)_{2-4}N_8NR_9$;

$R_6$ is selected from H, $C_{1-6}$alkyl branched or unbranched or $CO_2R_{10}$;

$R_7$ is H or $C_{1-6}$alkyl;

$R_8$ and $R_9$ are the same or different and are each independently selected from H, $C_{1-3}$alkyl branched or unbranched, $CO_2R_{10}$, phenyl, or benzoyl; wherein said alkyl, phenyl or benzoyl are optionally substituted with OH or $C_{1-3}$alkoxy;

or $R_8$ and $R_9$ together form a —$(CH_2)_2$—$N(CO_2R_{10})$—$(CH_2)_2$— group, a —$(CH_2)_2$—$N(COR_{10})$—$(CH_2)_2$— group, a —$(CH_2)_2$—$N(R_{11})$—$(CH_2)_2$— group or a —$(CH_2)_2$—$N(C(=NR_{11})NR_{11}R_{12})$—$(CH_2)_2$— group; and wherein said ring is optionally substituted by $C_{1-3}$ alkyl, $C_{1-3}$alkoxy, or OH;

$R_{10}$ is H or $C_{1-6}$alkyl optionally substituted with phenyl, OH, $C_{1-3}$alkoxy, $C_{1-3}$alkanoyloxy or $NR_{11}R_{12}$;

$R_{11}$ and $R_{12}$ are each independently selected from H and $C_{1-3}$ alkyl optionally substituted with $C_{1-3}$alkoxy or OH;

or $R_{11}$ and $R_{12}$ together form a chain completing a ring, said chain is $(CH_2)_{4-5}$ or $(CH_2)_2O(CH_2)_2$.

In yet another embodiment of the invention there are provided compounds of the formula (I) as described immediately above, and wherein:

$Ar_1$ is phenyl;

$R_1$ and $R_2$ are the same or different and selected from: halogen, methyl optionally partially or fully halogenated, $NO_2$ and $NH_2$;

$R_3$ is H, chloro, fluoro, bromo or methoxy;

$R_5$ is selected from $C_{2-4}$ alkenyl, $C_{3-8}$ cycloalkyl or $C_{5-7}$cycloalkenyl, each being optionally substituted with one or more OH, CN, $NR_8R_9$, $CONR_8R_9$ or phenyl; wherein phenyl is optionally substituted with one or more $C_{1-3}$alkyl, $C_{1-3}$alkoxy, halogen, amidino, guanidino, $(CH_2)_nNR_8R_9$, or $O(CH_2)_{2-4}NR_8R_9$; wherein one or more of the amino nitrogens in the amidino or guanidino groups in this paragraph may be optionally substituted with $C_{1-3}$alkyl, phenyl$C_{0-3}$alkyl or $C_{1-3}$alkoxy;

or $R_5$ is selected from phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c]pyrrolyl or indolyl-CO—, wherein each phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c] pyrrolyl, or indolyl-CO— is optionally substituted with one to two:

halogen, $NO_2$, $SO_2NR_8R_9$, $NR_8R_9$, $(CH_2)_nCO_2R_{10}$, ureido, cycloalkyl, phenyl, heteroaryl, heterocycle, cycloalkyl-Z—, heteroaryl-Z— or heterocycle-Z—, or $C_{1-3}$alkyl optionally substituted with $NR_8R_9$, wherein Z is a bridging group selected from $C_{1-3}$ alkylene branched or unbranched, wherein each cycloalkyl, phenyl, heteroaryl or heterocycle is optionally substituted with $NO_2$, $C_{1-3}$alkyl, $CO_2R_{10}$, $NR_8R_9$ or guanidino, wherein one or more of the amino nitrogens in the guanidino group in this paragraph may be optionally substituted with $C_{1-3}$alkyl; and wherein each alkyl and phenyl in this paragraph is optionally partially or fully halogenated;

or $R_5$ is a 7-azabicyclo[2.2.1]heptane ring system, optionally having one or two double bonds in the ring system, wherein said ring system may be optionally substituted with $C_{1-3}$alkyl, $C_{1-3}$alkoxy, halogen, $(CH_2)_nNR_8R_9$, or $O(CH_2)_{2-4}NR_8R_9$;

$R_6$ is selected from H or $C_{1-3}$alkyl branched or unbranched;

R$_7$ is H or C$_{1-3}$alkyl;

R$_8$ and R$_9$ are the same or different and are each independently selected from H or C$_{1-3}$alkyl branched or unbranched; wherein said alkyl is optionally substituted with OH or C$_{1-3}$alkoxy;

or R$_8$ and R$_9$ together form a —(CH$_2$)$_2$—N(CO$_2$R$_{10}$)—(CH$_2$)$_2$—, a —(CH$_2$)$_2$—N(COR$_{10}$)—(CH$_2$)$_2$— group, a —(CH$_2$)$_2$—N(R$_{11}$)—(CH$_2$)$_2$— group or a —(CH$_2$)$_2$—N(C(=NR$_{11}$)NR$_{11}$R$_{12}$)—(CH$_2$)$_2$— group; and wherein said ring is optionally substituted by C$_{1-3}$ alkyl, C$_{1-3}$alkoxy, or OH;

R$_{10}$ is H or C$_{1-3}$alkyl optionally substituted with phenyl, OH or C$_{1-3}$alkanoyloxy; and R$_{11}$ is selected from H and C$_{1-3}$ alkyl.

In yet another embodiment of the invention, there are provided any of the compounds of formula (I) described above wherein Het represents a fused ring having formula B:

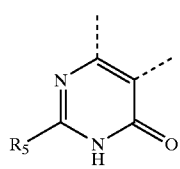

B

In still another embodiment of the invention, there are provided compounds of the formula (I') below:

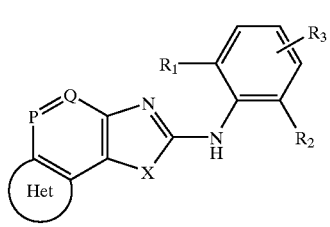

(I')

wherein:

X is NH, N—C$_{1-3}$alkyl, N-cyclopropyl, S or O;

R$_1$ and R$_2$ are the same or different and are selected from H, halogen, CN, NO$_2$, C$_{1-10}$ branched or unbranched saturated or unsaturated alkyl, C$_{1-10}$ branched or unbranched alkoxy, C$_{1-10}$ branched or unbranched acyl, C$_{1-10}$ branched or unbranched acyloxy, C$_{1-10}$ branched or unbranched alkylthio, aminosulfonyl, di-(C$_{1-3}$) alkylaminosulfonyl, NR$_8$R$_9$, aryl, aroyl, aryloxy, arylsulfonyl, heteroaryl and heteroaryloxy; wherein the abovementioned R$_1$ and R$_2$ are optionally partially or fully halogenated or optionally substituted with one to three groups independently selected from the group consisting of oxo, OH, NR$_8$R$_9$, C$_{1-6}$ branched or unbranched alkyl, C$_{3-7}$cycloalkyl, phenyl, naphthyl, heteroaryl, aminocarbonyl and mono- or di(C$_{1-3}$) alkylaminocarbonyl;

R$_3$ is selected from the group consisting of H, halogen, OH, (CH$_2$)$_n$NR$_8$R$_9$, (CH$_2$)$_n$CO$_2$R$_{10}$, C$_{1-3}$alkyl optionally substituted with OH, C$_{1-3}$ alkoxy optionally halogenated and C$_{1-3}$ alkylthio;

Het represents a fused heterocyclic ring having a formula A, B or C:

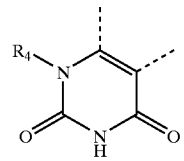

A

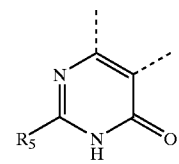

B

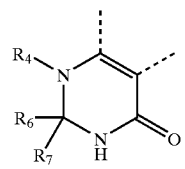

C

R$_4$ is selected from H, C$_{1-6}$ alkyl branched or unbranched, saturated or unsaturated, and optionally substituted with phenyl, OH or C$_{1-3}$alkoxy, C$_{3-10}$-cycloalkyl, or C$_{5-8}$cycloalkenyl; or R$_4$ is selected from (CH$_2$)$_m$NR$_8$R$_9$, (CH$_2$)$_m$NR$_8$COR$_{10}$, (CH$_2$)$_n$CO$_2$R$_{10}$, (CH$_2$)$_n$CONR$_8$R$_9$, phenyl, heteroaryl or heterocycle, each phenyl, heteroaryl or heterocycle being optionally substituted with C$_{1-3}$alkyl, C$_{1-3}$alkoxy, (CH$_2$)$_m$NR$_8$R$_9$, OH, SO$_3$H or halogen;

R$_5$ is selected from H, C$_{1-10}$alkyl branched or unbranched, C$_{3-10}$ cycloalkyl, C$_{5-7}$cycloalkenyl, C$_{2-6}$ alkenyl, C$_{2-6}$ alkynyl, C$_{1-6}$acyl, each being optionally substituted with one or more halogen, OH, oxo, CN, C$_{1-6}$alkyl, C$_{2-6}$ alkenyl, C$_{2-6}$ alkynyl, C$_{1-3}$alkoxy, NR$_8$R$_9$, ureido, guanidino, NR$_8$COR$_{10}$, SR$_{10}$, CONR$_8$R$_9$, CO$_2$R$_{10}$, C$_{3-10}$ cycloalkyl, C$_{3-10}$cycloalkylidene, C$_{5-7}$cycloalkenyl, aryloxy, arylthio, aryl, heteroaryl or heterocycle; wherein each of C$_{1-6}$alkyl, C$_{2-6}$ alkenyl, C$_{2-6}$ alkynyl, C$_{3-10}$cycloalkyl, C$_{3-10}$cycloalkylidene, C$_{5-7}$cycloalkenyl, aryloxy, arylthio, aryl, heteroaryl or heterocycle is optionally substituted with one or more C$_{1-3}$alkyl, C$_{1-3}$alkoxy, halogen, CN, NO$_2$, amidino, guanidino, (CH$_2$)$_n$NR$_8$R$_9$, or O(CH$_2$)$_{2-4}$NR$_8$R$_9$; wherein one or more of the amino nitrogens in the ureido, amidino or guanidino groups in this paragraph may be optionally substituted with C$_{1-3}$alkyl, phenylC$_{0-3}$alkyl, C$_{1-3}$alkoxy or CO$_2$R$_{10}$;

or R$_5$ is selected from CO$_2$R$_{10}$, NR$_8$R$_9$, CONR$_8$R$_9$, aryl, heteroaryl, heterocycle, aryl-CO—, heteroaryl-CO— or heterocycle-CO—, wherein each aryl, heteroaryl or heterocycle is optionally substituted with one to three:

C$_{1-3}$alkoxy, halogen, NO$_2$, CN, S(O)$_p$NR$_8$R$_9$, C$_{0-3}$alkylS(O)$_p$, NR$_8$R$_9$, (CH$_2$)$_n$CO$_2$R$_{10}$, (CH$_2$)$_n$CONR$_8$R$_9$, CO(CH$_2$)$_n$NR$_8$R$_9$, O(CH$_2$)$_{2-4}$NR$_8$R$_9$, ureido, guanidino, cycloalkyl, aryl, heteroaryl, heterocycle, cycloalkyl-Z—, aryl-Z—, heteroaryl-Z—, heterocycle-Z—, or C$_{1-3}$alkyl optionally substituted with phenyl or NR$_8$R$_9$, wherein Z is a bridging group selected from C$_{1-10}$ alkylene branched or unbranched, CO, S(O)$_p$, O, S, NH, CONH, NHCO, COO or OOC, and wherein each cycloalkyl, aryl, heteroaryl or heterocycle is optionally substituted with NO$_2$, C$_{1-3}$alkyl, C$_{1-3}$alkoxy, halogen, $CO_2R_{10}$, $(CH_2)_nNR_8R_9$, $O(CH_2)_{2-4}NR_8R_9$, ureido or guanidino, wherein one or more of the amino nitrogens in the ureido or guanidino groups in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-12}$ bridged- or spiro-bicyclic ring system, optionally having one or two double bonds in the ring system, and wherein up to 3 carbon atoms in the ring system may be replaced by heteroatoms selected from N, O and S; and wherein said ring system may be optionally substituted with $C_{1-3}$alkyl, $C_{1-3}$alkoxy, halogen, $CO_2R_{10}$, ureido, guanidino, amidino, $(CH_2)_nNR_8R_9$, or $O(CH_2)_{2-4}NR_8R_9$; wherein one or more of the amino nitrogens in the ureido, guanidino or amidino groups in this paragraph may be optionally substituted with $C_{1-3}$alkyl, phenyl$C_{0-3}$alkyl or $C_{1-3}$alkoxy;

$R_6$ is selected from H, $C_{1-6}$alkyl branched or unbranched, $C_{2-6}$ alkenyl branched or unbranched, $CO_2R_{10}$, $C_{3-8}$cycloalkyl, $C_{3-8}$cycloalkenyl, aryl, aryl$C_{1-3}$alkyl, heteroaryl and heterocyclyl; wherein said $C_{1-6}$alkyl, $C_{2-6}$alkenyl, $C_{3-8}$cycloalkyl, $C_{3-8}$cycloalkenyl, aryl, aryl$C_{1-3}$alkyl, heteroaryl or heterocyclyl are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl, heteroaryl or heterocyclyl;

$R_7$ is H or $C_{1-6}$alkyl;

$R_8$ and $R_9$ are the same or different and are each independently selected from H, OH, $CO_2R_{10}$, $C_{1-10}$ acyl branched or unbranched, $C_{1-3}$alkoxy, $C_{1-6}$alkyl branched or unbranched, $C_{3-6}$alkenyl, $C_{3-8}$cycloalkyl, aryl, aryl$C_{1-3}$alkyl, aroyl, heteroaryl or heterocycle; wherein said alkyl, cycloalkyl, aryl, aryl$C_{1-3}$alkyl, aroyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl;

or $R_8$ and $R_9$ together form a 3–7 member alkylene chain completing a ring about the N atom to which they are attached; wherein said alkylene chain is optionally interrupted by O, $S(O)_p$, $NCOR_{10}$, $NCO_2R_{10}$, $NR_{11}$ or $NC(=NR_{11})NR_{11}R_{12}$; and wherein said ring is optionally substituted by $C_{1-3}$ alkyl, $C_{1-3}$alkoxy, OH or —$(CH_2)_nNR_{11}R_{12}$;

$R_{10}$ is selected from H, $C_{1-6}$alkyl, $C_{3-8}$cycloalkyl, wherein each alkyl or cycloalkyl is optionally substituted with phenyl, OH, $C_{1-3}$alkoxy, $C_{1-3}$alkanoyloxy or $NR_{11}R_{12}$, or $R_{10}$ is phenyl optionally substituted with one to three $C_{1-3}$alkyl, $C_{1-3}$alkoxy, halogen, $(CH_2)_mNR_8R_9$, $(CH_2)_nCONR_8R_9$ or $O(CH_2)_{2-4}NR_8R_9$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$;

$R_{13}$ is H or $C_{1-3}$alkyl;

P and Q are each independently CH or N;

m is 1–4;

n is 0–3;

and p is 0–2;

wherein one or more of the primary amine or secondary amine nitrogen atoms in any of the $R_4$, $R_5$, $R_6$ and $R_7$ substituent groups may optionally be protected by a protecting group;

and the pharmaceutically acceptable derivatives thereof.

In another embodiment of the invention there are provided compounds of the formula(I') as described above, and wherein:

X is NH or N—$C_{1-3}$alkyl;

$R_1$ and $R_2$ are the same or different and selected from: halogen, $C_{1-3}$ alkyl, wherein the $C_{13}$ alkyl is optionally partially or fully halogenated, $NO_2$ or $NR_8R_9$;

$R_3$ is H, halogen, methyl or methoxy;

$R_4$ is H, $C_{1-3}$alkyl branched or unbranched, saturated or unsaturated, and optionally substituted with OH; or $R_4$ is $(CH_2)_{2-3}NR_8R_9$ or $CO_2R_{10}$;

$R_5$ is selected from H, $C_{1-3}$alkyl branched or unbranched, $C_{3-8}$ cycloalkyl, $C_{5-7}$cycloalkenyl or $C_{2-4}$ alkenyl, each being optionally substituted with one or more OH, CN, $NR_8R_9$, $CONR_8R_9$, $C_{3-8}$ cycloalkyl, $C_{5-7}$cycloalkenyl, phenyl, heteroaryl or heterocycle; wherein each phenyl, heteroaryl or heterocycle is optionally substituted with one or more $C_{1-3}$alkyl, $C_{1-3}$alkoxy, halogen, CN, $NO_2$, amidino, guanidino, $(CH_2)_nNR_8R_9$, or $O(CH_2)_{2-4}NR_8R_9$; wherein one or more of the amino nitrogens in the amidino or guanidino groups in this paragraph may be optionally substituted with $C_{1-3}$alkyl, phenyl$C_{0-3}$alkyl, $C_{1-3}$alkoxy or $CO_2R_{10}$;

or $R_5$ is selected from $CO_2R_{10}$, $NR_8R_9$, $CONR_8R_9$, phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl, or indolyl-CO—, wherein each phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl or indolyl-CO— is optionally substituted with one to three:

halogen, $NO_2$, $S(O)_pNR_8R_9$, $CO_{0-3}$alkyl$S(O)_p$, $NR_8R_9$, $(CH_2)_nCO_2R_{10}$, ureido, guanidino, cycloalkyl, phenyl, heteroaryl, heterocycle, cycloalkyl-Z—, phenyl-Z—, heteroaryl-Z—, heterocycle-Z—, or $C_{1-3}$alkyl optionally substituted with phenyl or $NR_8R_9$, wherein Z is a bridging group selected from $C_{1-3}$ alkylene branched or unbranched, O, $S(O)_p$ or NH, and wherein each cycloalkyl, phenyl, heteroaryl or heterocycle is optionally substituted with $NO_2$, $C_{1-3}$alkyl, $C_{1-3}$alkoxy, $CO_2R_{10}$, $(CH_2)_nNR_8R_9$, $O(CH_2)_{2-4}NR_8R_9$ or guanidino, wherein one or more of the amino nitrogens in the guanidino group in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-7}$ bridged-bicyclic ring system, optionally having one or two double bonds in the ring system, and wherein up to 1 carbon atom in the ring system may be replaced by a nitrogen atom; and wherein said ring system may be optionally substituted with $C_{1-3}$alkyl, $C_{1-3}$alkoxy, halogen, $(CH_2)_nNR_8R_9$, or $O(CH_2)_{2-4}NR_8R_9$;

$R_6$ is selected from H, $C_{1-6}$alkyl branched or unbranched or $CO_2R_{10}$;

$R_7$ is H or $C_{1-6}$alkyl;

$R_8$ and $R_9$ are the same or different and are each independently selected from H, $C_{1-3}$alkyl branched or unbranched, $CO_2R_{10}$, phenyl, or benzoyl; wherein said alkyl, phenyl or benzoyl are optionally substituted with OH or $C_{1-3}$alkoxy;

or $R_8$ and $R_9$ together form a —$(CH_2)_2$—N(CO$_2$R$_{10}$)—$(CH_2)_2$— group, a —$(CH_2)_2$—N(COR$_{10}$)—$(CH_2)_2$— group, a —$(CH_2)_2$—N(R$_{11}$)—$(CH_2)_2$— group or a —$(CH_2)_2$—N(C(=NR$_{11}$)NR$_{11}$R$_{12}$)—$(CH_2)_2$— group; and wherein said ring is optionally substituted by $C_{1-3}$ alkyl, $C_{1-3}$alkoxy, or OH;

$R_{10}$ is H or $C_{1-6}$alkyl optionally substituted with phenyl, OH, $C_{1-3}$alkoxy, $C_{1-3}$alkanoyloxy or NR$_{11}$R$_{12}$;

$R_{11}$ and $R_{12}$ are each independently selected from H and $C_{1-3}$ alkyl optionally substituted with $C_{1-3}$alkoxy or OH;

or $R_{11}$ and $R_{12}$ together form a chain completing a ring, said chain is $(CH_2)_{4-5}$ or $(CH_2)_2O(CH_2)_2$; and P and Q are each CH.

In still a further embodiment of the invention there are provided compounds of the formula (I') as described immediately above, and wherein:

$R_1$ and $R_2$ are the same or different and selected from: halogen, methyl optionally partially or fully halogenated, NO$_2$ and NH$_2$;

$R_3$ is H, chloro, fluoro, bromo or methoxy;

$R_5$ is selected from $C_{2-4}$ alkenyl, $C_{3-8}$ cycloalkyl or $C_{5-7}$cycloalkenyl, each being optionally substituted with one or more OH, CN, NR$_8$R$_9$, CONR$_8$R$_9$ or phenyl; wherein phenyl is optionally substituted with one or more $C_{1-3}$alkyl, $C_{1-3}$alkoxy, halogen, amidino, guanidino, $(CH_2)_n$NR$_8$R$_9$, or O(CH$_2$)$_{2-4}$NR$_8$R$_9$; wherein one or more of the amino nitrogens in the amidino or guanidino groups in this paragraph may be optionally substituted with $C_{1-3}$alkyl, phenylC$_{0-3}$alkyl or $C_{1-3}$alkoxy;

or $R_5$ is selected from phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c]pyrrolyl or indolyl-CO—, wherein each phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c]pyrrolyl or indolyl-CO— is optionally substituted with one to two:

halogen, NO$_2$, SO$_2$NR$_8$R$_9$, NR$_8$R$_9$, $(CH_2)_n$CO$_2$R$_{10}$, ureido, cycloalkyl, phenyl, heteroaryl, heterocycle, cycloalkyl-Z—, heteroaryl-Z— or heterocycle-Z—, or $C_{1-3}$alkyl optionally substituted with NR$_8$R$_9$, wherein Z is a bridging group selected from $C_{1-3}$ alkylene branched or unbranched or S(O)$_p$, wherein each cycloalkyl, phenyl, heteroaryl or heterocycle is optionally substituted with NO$_2$, $C_{1-3}$alkyl, CO$_2$R$_{10}$, NR$_8$R$_9$ or guanidino, wherein one or more of the amino nitrogens in the guanidino group in this paragraph may be optionally substituted with $C_{1-3}$alkyl; and wherein each alkyl and phenyl in this paragraph is optionally partially or fully halogenated;

or $R_5$ is a 7-azabicyclo[2.2.1]heptane ring system, optionally having one or two double bonds in the ring system, wherein said ring system may be optionally substituted with $C_{1-3}$alkyl, $C_{1-3}$alkoxy, halogen, $(CH_2)_n$NR$_8$R$_9$, or O(CH$_2$)$_{2-4}$NR$_8$R$_9$;

$R_6$ is selected from H or $C_{1-3}$alkyl branched or unbranched;

$R_7$ is H or $C_{1-3}$alkyl;

$R_8$ and $R_9$ are the same or different and are each independently selected from H or $C_{1-3}$alkyl branched or unbranched; wherein said alkyl is optionally substituted with OH or $C_{1-3}$alkoxy;

or $R_8$ and $R_9$ together form a —$(CH_2)_2$—N(CO$_2$R$_{10}$)—$(CH_2)_2$—, a —$(CH_2)_2$—N(COR$_{10}$)—$(CH_2)_2$— group, a —$(CH_2)_2$—N(R$_{11}$)—$(CH_2)_2$— group or a —$(CH_2)_2$—N(C(=NR$_{11}$)NR$_{11}$R$_{12}$)—$(CH_2)_2$— group; and wherein said ring is optionally substituted by $C_{1-3}$ alkyl, $C_{1-3}$alkoxy, or OH;

$R_{10}$ is H or $C_{1-3}$alkyl optionally substituted with phenyl, OH or $C_{1-3}$alkanoyloxy; and $R_{11}$ is selected from H and $C_{1-3}$ alkyl.

In yet another embodiment of the invention, there are provided any of the compounds of formula (I') described above wherein Het represents a fused ring having formula B:

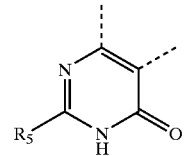

B

In yet another aspect of the invention, there are provided compounds of the following formula Ib:

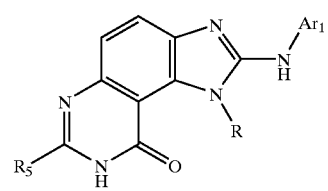

Ib wherein R is H, $C_{1-3}$alkyl or cyclopropyl, and Ar$_1$ and R$_5$ are as defined in formula (I) above.

The present invention is also directed to the intermediate compounds of the following formulae (VI), (XII), (XVIII) and (XIX) useful in the synthetic schemes and examples set forth below.

Formula (VI)

In their broadest generic aspect, intermediate compounds of the formula (VI) are represented by the following formula:

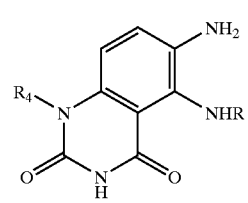

VI wherein:

R is H, $C_{1-3}$alkyl or cyclopropyl;

$R_4$ is selected from H, $C_{1-6}$ alkyl branched or unbranched, saturated or unsaturated, and optionally substituted with phenyl, OH or $C_{1-3}$alkoxy; or $R_4$ is selected from $(CH_2)_m$NR$_8$R$_9$, $(CH_2)_m$NR$_8$COR$_{10}$, $(CH_2)_n$CO$_2$R$_{10}$ or $(CH_2)_n$CONR$_8$R$_9$;

$R_8$ and $R_9$ are the same or different and are each independently selected from H, OH, CO$_2$R$_{10}$, $C_{1-10}$acyl branched or unbranched, $C_{1-3}$alkoxy, $C_{1-6}$alkyl branched or unbranched, $C_{3-6}$alkenyl, $C_{3-8}$cycloalkyl, aryl, arylC$_{1-3}$alkyl, aroyl, heteroaryl or heterocycle; wherein said alkyl, cycloalkyl, aryl, arylC$_{1-3}$alkyl, aroyl, heteroaryl or heterocycle are optionally substituted with OH, C$_{1-3}$alkoxy, C$_{1-3}$acyloxy, CO$_2$R$_{10}$, NR$_{11}$R$_{12}$, O(CH$_2$)$_{2-4}$NR$_{11}$R$_{12}$, aryl or heteroaryl;

or R$_9$ and R$_9$ together form a 3–7 member alkylene chain completing a ring about the N atom to which they are attached; wherein said alkylene chain is optionally interrupted by O, S(O)$_p$, NCOR$_{10}$, NCO$_2$R$_{10}$, NR$_{11}$ or NC(=NR$_{11}$)NR$_{11}$R$_{12}$; and wherein said ring is optionally substituted by C$_{1-3}$ alkyl, C$_{1-3}$alkoxy, OH or —(CH$_2$)$_n$NR$_{11}$R$_{12}$;

R$_{10}$ is selected from H, C$_{1-6}$alkyl, C$_{3-8}$cycloalkyl, wherein each alkyl or cycloalkyl is optionally substituted with phenyl, OH, C$_{1-3}$alkoxy, C$_{1-3}$alkanoyloxy or NR$_{11}$R$_{12}$, or R$_{10}$ is phenyl optionally substituted with one to three C$_{1-3}$alkyl, C$_{1-3}$alkoxy, halogen, (CH$_2$)$_m$NR$_8$R$_9$, (CH$_2$)$_n$CONR$_8$R$_9$ or O(CH$_2$)$_{2-4}$NR$_8$R$_9$;

R$_{11}$ and R$_{12}$ are each independently selected from H and C$_{1-6}$ alkyl optionally substituted with C$_{1-3}$alkoxy, OH or phenyl;

or R$_{11}$ and R$_{12}$ together form a chain completing a ring, said chain is (CH$_2$)$_{4-5}$ or (CH$_2$)$_2$O(CH$_2$)$_2$;

m is 1–4;

n is 1–3;

and p is 0–2;

wherein one or more of the primary amine or secondary amine nitrogen atoms in the R$_4$ substituent group may optionally be protected by a protecting group.

One embodiment of the compounds of formula (VI) are those wherein:

R is H or C$_{1-3}$alkyl; and

R$_4$ is H, C$_{1-3}$alkyl branched or unbranched, saturated or unsaturated, and optionally substituted with OH; or R$_4$ is (CH$_2$)$_{2-3}$NR$_8$R$_9$, (CH$_2$)$_n$CO$_2$R$_{10}$ or (CH$_2$)$_n$CONR$_8$R$_9$.

Formula (XII)

In their broadest generic aspect, intermediate compounds of formula (XII) are represented by the following formula:

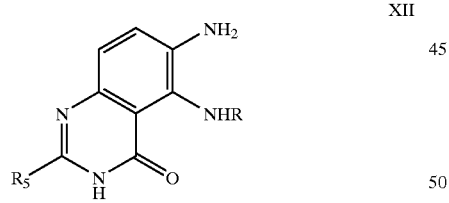

XII wherein:

R is H, C$_{1-3}$alkyl or cyclopropyl; and

R$_5$ is selected from H, C$_{1-10}$alkyl branched or unbranched, C$_{3-10}$ cycloalkyl, C$_{5-7}$cycloalkenyl, C$_{2-6}$ alkenyl, C$_{2-6}$ alkynyl, C$_{1-6}$acyl, each being optionally substituted with one or more halogen, OH, oxo, CN, C$_{1-6}$alkyl, C$_{2-6}$ alkenyl, C$_{2-6}$ alkynyl, C$_{1-3}$alkoxy, NR$_8$R$_9$, ureido, guanidino, NR$_8$COR$_{10}$, SR$_{10}$, CONR$_8$R$_9$, CO$_2$R$_{10}$, C$_{3-10}$ cycloalkyl, C$_{3-10}$cycloalkylidene, C$_{5-7}$cycloalkenyl, aryloxy, arylthio, aryl, heteroaryl or heterocycle; wherein each of C$_{1-6}$alkyl, C$_{2-6}$ alkenyl, C$_{2-6}$ alkynyl, C$_{3-10}$cycloalkyl, C$_{3-10}$cycloalkylidene, C$_{5-7}$cycloalkenyl, aryloxy, arylthio, aryl, heteroaryl or heterocycle is optionally substituted with one or more C$_{1-3}$alkyl, C$_{1-3}$alkoxy, halogen, CN, NO$_2$, amidino, guanidino, (CH$_2$)$_n$NR$_8$R$_9$, or O(CH$_2$)$_{2-4}$NR$_8$R$_9$; wherein one or more of the amino nitrogens in the ureido, amidino or guanidino groups in this paragraph may be optionally substituted with C$_{1-3}$alkyl, phenylC$_{0-3}$alkyl, C$_{1-3}$alkoxy or CO$_2$R$_{10}$;

or R$_5$ is selected from CO$_2$R$_{10}$, NR$_8$R$_9$, CONR$_8$R$_9$, aryl, heteroaryl, heterocycle, aryl-CO—, heteroaryl-CO— or heterocycle-CO—, wherein each aryl, heteroaryl or heterocycle is optionally substituted with one to three: C$_{1-3}$alkoxy, halogen, NO$_2$, CN, S(O)$_p$NR$_8$R$_9$, C$_{0-3}$alkylS(O)$_p$, NR$_8$R$_9$, (CH$_2$)$_n$CO$_2$R$_{10}$, (CH$_2$)$_n$CONR$_8$R$_9$, CO(CH$_2$)$_n$NR$_8$R$_9$, O(CH$_2$)$_{2-4}$NR$_8$R$_9$, ureido, guanidino, cycloalkyl, aryl, heteroaryl, heterocycle, cycloalkyl-Z—, aryl-Z—, heteroaryl-Z—, heterocycle-Z—, or C$_{1-3}$alkyl optionally substituted with phenyl or NR$_8$R$_9$, wherein Z is a bridging group selected from C$_{1-10}$ alkylene branched or unbranched, CO, S(O)$_p$, O, S, NH, CONH, NHCO, COO or OOC, and wherein each cycloalkyl, aryl, heteroaryl or heterocycle is optionally substituted with NO$_2$, C$_{1-3}$alkyl, C$_{1-3}$alkoxy, halogen, CO$_2$R$_{10}$, (CH$_2$)$_n$NR$_8$R$_9$, O(CH$_2$)$_{2-4}$NR$_8$R$_9$, ureido or guanidino, wherein one or more of the amino nitrogens in the ureido or guanidino groups in this paragraph may be optionally substituted with C$_{1-3}$alkyl, phenylC$_{0-3}$alkyl or C$_{1-3}$alkoxy; and wherein each alkyl, alkoxy and phenyl in this paragraph is optionally partially or fully halogenated;

or R$_5$ is a C$_{6-12}$ bridged- or spiro-bicyclic ring system, optionally having one or two double bonds in the ring system, and wherein up to 3 carbon atoms in the ring system may be replaced by heteroatoms selected from N, O and S; and wherein said ring system may be optionally substituted with C$_{1-3}$alkyl, C$_{1-3}$alkoxy, halogen, CO$_2$R$_{10}$, ureido, guanidino, amidino, (CH$_2$)$_n$NR$_8$R$_9$, or O(CH$_2$)$_{2-4}$NR$_8$R$_9$; wherein one or more of the amino nitrogens in the ureido, guanidino or amidino groups in this paragraph may be optionally substituted with C$_{1-3}$alkyl, phenylC$_{0-3}$alkyl or C$_{1-3}$alkoxy;

R$_6$ is selected from H, C$_{1-6}$alkyl branched or unbranched, C$_{2-6}$ alkenyl branched or unbranched, CO$_2$R$_{10}$, C$_{3-8}$cycloalkyl, C$_{3-8}$cycloalkenyl, aryl, arylC$_{1-3}$alkyl, heteroaryl and heterocyclyl; wherein said C$_{1-6}$alkyl, C$_{2-6}$alkenyl, C$_{3-8}$cycloalkyl, C$_{3-8}$cycloalkenyl, aryl, arylC$_{1-3}$alkyl, heteroaryl or heterocyclyl are optionally substituted with OH, C$_{1-3}$alkoxy, C$_{1-3}$acyloxy, CO$_2$R$_{10}$, NR$_{11}$R$_{12}$, O(CH$_2$)$_{2-4}$NR$_{11}$R$_{12}$, aryl, heteroaryl or heterocyclyl;

R$_7$ is H or C$_{1-6}$alkyl;

R$_8$ and R$_9$ are the same or different and are each independently selected from H, OH, CO$_2$R$_{10}$, C$_{1-10}$ acyl branched or unbranched, C$_{1-3}$alkoxy, C$_{1-6}$alkyl branched or unbranched, C$_{3-6}$alkenyl, C$_{3-8}$cycloalkyl, aryl, arylC$_{1-3}$alkyl, aroyl, heteroaryl or heterocycle; wherein said alkyl, cycloalkyl, aryl, arylC$_{1-3}$alkyl, aroyl, heteroaryl or heterocycle are optionally substituted with OH, C$_{1-3}$alkoxy, C$_{1-3}$acyloxy, CO$_2$R$_{10}$, NR$_{11}$R$_{12}$, O(CH$_2$)$_{2-4}$NR$_{11}$R$_{12}$, aryl or heteroaryl;

or R$_8$ and R$_9$ together form a 3–7 member alkylene chain completing a ring about the N atom to which they are attached; wherein said alkylene chain is optionally interrupted by O, S(O)$_p$, NCOR$_{10}$, NCO$_2$R$_{10}$, NR$_{11}$ or NC(=NR$_{11}$)NR$_{11}$R$_{12}$; and wherein said ring is optionally substituted by C$_{1-3}$ alkyl, C$_{1-3}$alkoxy, OH or —(CH$_2$)$_n$NR$_{11}$R$_{12}$;

R$_{10}$ is selected from H, C$_{1-6}$alkyl, C$_{3-8}$cycloalkyl, wherein each alkyl or cycloalkyl is optionally substituted with phenyl, OH, $C_{1-3}$alkoxy, $C_{1-3}$alkanoyloxy or $NR_1 R_{12}$, or $R_{10}$ is phenyl optionally substituted with one to three $C_{1-3}$alkyl, $C_{1-3}$alkoxy, halogen, $(CH_2)_m NR_8 R_9$, $(CH_2)_n CONR_8 R_9$ or $O(CH_2)_{2-4} NR_8 R_9$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2 O(CH_2)_2$;

m is 1–4;

n is 0–3;

and p is 0–2;

wherein one or more of the primary amine or secondary amine nitrogen atoms in any of the $R_4$, $R_5$, $R_6$ and $R_7$ substituent groups may optionally be protected by a protecting group.

One embodiment of the compounds of formula (XII) are those wherein:

R is H or $C_{1-3}$alkyl; and $R_5$ is selected from H, $C_{1-3}$alkyl branched or unbranched, $C_{3-8}$ cycloalkyl, $C_{5-7}$cycloalkenyl or $C_{2-4}$ alkenyl, each being optionally substituted with one or more OH, CN, $NR_8R_9$, $CONR_8R_9$, $C_{3-8}$ cycloalkyl, $C_{5-7}$cycloalkenyl, phenyl, heteroaryl or heterocycle; wherein each phenyl, heteroaryl or heterocycle is optionally substituted with one or more $C_{1-3}$alkyl, $C_{1-3}$alkoxy, halogen, CN, $NO_2$, amidino, guanidino, $(CH_2)_n NR_8R_9$, or $O(CH_2)_{2-4} NR_8R_9$; wherein one or more of the amino nitrogens in the amidino or guanidino groups in this paragraph may be optionally substituted with $C_{1-3}$alkyl, phenyl$C_{0-3}$alkyl, $C_{1-3}$alkoxy or $CO_2R_{10}$;

or $R_5$ is selected from $CO_2R_{10}$, $NR_8R_9$, $CONR_8R_9$, phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl, or indolyl-CO—, wherein each phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl or indolyl-CO— is optionally substituted with one to three:

halogen, $NO_2$, $S(O)_p NR_8R_9$, $CO_{0-3}$alkyl$S(O)_p$, $NR_8R_9$, $(CH_2)_n CO_2R_{10}$, ureido, guanidino, cycloalkyl, phenyl, heteroaryl, heterocycle, cycloalkyl-Z—, phenyl-Z—, heteroaryl-Z—, heterocycle-Z—, or $C_{1-3}$alkyl optionally substituted with phenyl or $NR_8R_9$, wherein Z is a bridging group selected from $C_{1-3}$ alkylene branched or unbranched, O, $S(O)_p$ or NH, and wherein each cycloalkyl, phenyl, heteroaryl or heterocycle is optionally substituted with $NO_2$, $C_{1-3}$alkyl, $C_{1-3}$alkoxy, $CO_2R_{10}$, $(CH_2)_n NR_8R_9$, $O(CH_2)_{2-4} NR_8R_9$ or guanidino, wherein one or more of the amino nitrogens in the guanidino group in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-7}$ bridged-bicyclic ring system, optionally having one or two double bonds in the ring system, and wherein up to 1 carbon atom in the ring system may be replaced by a nitrogen atom; and wherein said ring system may be optionally substituted with $C_{1-3}$alkyl, $C_{1-3}$alkoxy, halogen, $(CH_2)_n NR_8R_9$, or $O(CH_2)_{2-4} NR_8R_9$;

Yet another embodiment of the compounds of formula (XII) are those described immediately above, wherein:

$R_5$ is selected from $C_{2-4}$ alkenyl, $C_{3-8}$ cycloalkyl or $C_{5-7}$cycloalkenyl, each being optionally substituted with one or more OH, CN, $NR_8R_9$, $CONR_8R_9$ or phenyl; wherein phenyl is optionally substituted with one or more $C_{1-3}$alkyl, $C_{1-3}$alkoxy, halogen, amidino, guanidino, $(CH_2)_n NR_8R_9$, or $O(CH_2)_{2-4} NR_8R_9$; wherein one or more of the amino nitrogens in the amidino or guanidino groups in this paragraph may be optionally substituted with $C_{1-3}$alkyl, phenyl$C_{0-3}$alkyl or $C_{1-3}$alkoxy;

or $R_5$ is selected from phenyl, furyl, thienyl, oxazolyl, thiazolyl , pyridinyl, benzofuranyl, 1,2,5,6-tetrahydropyridinyl, pyrrolinyl, 1,2,3,3a,4,6a-hexahydro-cyclopenta[c]pyrrolyl or indolyl-CO—, wherein each phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c] pyrrolyl or indolyl-CO— is optionally substituted with one to two:

halogen, $NO_2$, $SO_2NR_8R_9$, $NR_8R_9$, $(CH_2)_n CO_2R_{10}$, ureido, cycloalkyl, phenyl, heteroaryl, heterocycle, cycloalkyl-Z—, heteroaryl-Z— or heterocycle-Z—, or $C_{1-3}$alkyl optionally substituted with $NR_8R_9$, wherein Z is a bridging group selected from $C_{1-3}$ alkylene branched or unbranched or $S(O)_p$, wherein each cycloalkyl, phenyl, heteroaryl or heterocycle is optionally substituted with $NO_2$, $C_{1-3}$alkyl, $CO_2R_{10}$, $NR_8R_9$ or guanidino, wherein one or more of the amino nitrogens in the guanidino group in this paragraph may be optionally substituted with $C_{1-3}$alkyl; and wherein each alkyl and phenyl in this paragraph is optionally partially or fully halogenated;

or $R_5$ is a 7-azabicyclo[2.2.1]heptane ring system, optionally having one or two double bonds in the ring system, wherein said ring system may be optionally substituted with $C_{1-3}$alkyl, $C_{1-3}$alkoxy, halogen, $(CH_2)_n NR_8R_9$, or $O(CH_2)_{2-4} NR_8R_9$;

Formula (XVIII)

In their broadest generic aspect, intermediate compounds of the formula (XVIII) are represented by the following formula:

XVIII wherein:

$Ar_1$ is an aromatic or nonaromatic carbocycle, heteroaryl or heterocycle; wherein said carbocycle, heteroaryl or heterocycle is optionally substituted by one or more $R_1$, $R_2$ and $R_3$;

R is H, $C_{1-3}$alkyl or cyclopropyl;

$R_1$ and $R_2$ are the same or different and are selected from H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, di-$(C_{1-3})$ alkylaminosulfonyl, $NR_8R_9$, aryl, aroyl, aryloxy, arylsulfonyl, heteroaryl and heteroaryloxy; wherein the abovementioned $R_1$ and $R_2$ are optionally partially or fully halogenated or optionally substituted with one to three groups independently selected from the group consisting of oxo, OH, $NR_8R_9$, $C_{1-6}$ branched or unbranched alkyl, $C_{3-7}$cycloalkyl, phenyl, naphthyl, heteroaryl, aminocarbonyl and mono- or di($C_{1-3}$) alkylaminocarbonyl;

$R_3$ is selected from the group consisting of H, halogen, OH, $(CH_2)_nNR_8R_9$, $(CH_2)_nCO_2R_{10}$, $C_{1-3}$alkyl optionally substituted with OH, $C_{1-3}$ alkoxy optionally halogenated and $C_{1-3}$ alkylthio;

$R_4$ is selected from H, $C_{1-6}$ alkyl branched or unbranched, saturated or unsaturated, and optionally substituted with phenyl, OH or $C_{1-3}$alkoxy, $C_{3-10}$-cycloalkyl, or $C_{5-8}$cycloalkenyl;

or $R_4$ is selected from $(CH_2)_mNR_8R_9$, $(CH_2)_mNR_8COR_{10}$, $(CH_2)_nCO_2R_{10}$, $(CH_2)_nCONR_8R_9$, phenyl, heteroaryl or heterocycle, each phenyl, heteroaryl or heterocycle being optionally substituted with $C_{1-3}$alkyl, $C_{1-3}$alkoxy, $(CH_2)_mNR_8R_9$, OH, $SO_3H$ or halogen;

$R_8$ and $R_9$ are the same or different and are each independently selected from H, OH, $CO_2R_{10}$, $C_{1-10}$ acyl branched or unbranched, $C_{1-3}$alkoxy, $C_{1-6}$alkyl branched or unbranched, $C_{3-6}$alkenyl, $C_{3-8}$cycloalkyl, aryl, aryl$C_{1-3}$alkyl, aroyl, heteroaryl or heterocycle; wherein said alkyl, cycloalkyl, aryl, aryl$C_{1-3}$alkyl, aroyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl;

or $R_8$ and $R_9$ together form a 3–7 member alkylene chain completing a ring about the N atom to which they are attached; wherein said alkylene chain is optionally interrupted by O, $S(O)_p$, $NCOR_{10}$, $NCO_2R_{10}$, $NR_{11}$ or $NC(=NR_{11})NR_{11}R_{12}$; and wherein said ring is optionally substituted by $C_{1-3}$ alkyl, $C_{1-3}$alkoxy, OH or —$(CH_2)_nNR_{11}R_{12}$;

$R_{10}$ is selected from H, $C_{1-6}$alkyl, $C_{3-8}$cycloalkyl, wherein each alkyl or cycloalkyl is optionally substituted with phenyl, OH, $C_{1-3}$alkoxy, $C_{1-3}$alkanoyloxy or $NR_{11}R_{12}$, or $R_{10}$ is phenyl optionally substituted with one to three $C_{1-3}$alkyl, $C_{1-3}$alkoxy, halogen, $(CH_2)_mNR_8R_9$, $(CH_2)_nCONR_8R_9$ or $O(CH_2)_{2-4}NR_8R_9$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$;

m is 1–4;

n is 0–3;

and p is 0–2;

wherein one or more of the primary amine or secondary amine nitrogen atoms in any of the $R_4$, $R_5$, $R_6$ and $R_7$ substituent groups may optionally be protected by a protecting group.

One embodiment of the compounds of formula (XVIII) are those wherein:

$Ar_1$ is a) a cycloalkyl group selected from cyclopropyl, cyclobutyl, cyclopentanyl, cyclohexanyl and cycloheptanyl;

b) a cycloalkenyl group selected from cyclopentenyl, cyclohexenyl, and cycloheptenyl;

c) an aromatic carbocycle selected from phenyl, naphthyl, indanyl, indenyl, dihydronaphthyl, tetrahydronaphthyl or fluorenyl, d) a heteroaryl selected from pyridyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl,or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or e) a heterocycle selected from: pyrrolinyl, pyrrolidinyl, pyrazolinyl, pyrazolidinyl, piperidinyl, morpholinyl, thiomorpholinyl, pyranyl, thiopyranyl, piperazinyl and indolinyl;

wherein each of the above $Ar_1$ are optionally substituted by one or more $R_1$, $R_2$ and $R_3$;

$R_1$ and $R_2$ are as defined in claim 1, and $R_3$ is hydrogen, halogen, methyl, methoxy, hydroxymethyl or OH; and $R_4$ is H, $C_{1-3}$alkyl branched or unbranched, saturated or unsaturated, and optionally substituted with OH; or $R_4$ is $(CH_2)_{2-3}NR_8R_9$, $(CH_2)_nCO_2R_{10}$ or $(CH_2)_nCONR_8R_9$;

$R_8$ and $R_9$ are the same or different and are each independently selected from H, OH, $C_{1-3}$alkyl branched or unbranched, $CO_2R_{10}$, $C_{3-8}$cycloalkyl, phenyl, benzyl, benzoyl, heteroaryl or heterocycle; wherein said alkyl, cycloalkyl, phenyl, benzyl, benzoyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl; or $R_8$ and $R_9$ together form a 4–6 member alkylene chain completing a ring about the N atom to which they are attached; wherein said alkylene chain is optionally interrupted by $NCO_2R_{10}$ or $NR_{11}$; and wherein said ring is optionally substituted by $C_{1-3}$ alkyl, $C_{1-3}$alkoxy, OH or —$(CH_2)_nNR_{11}R_{12}$;

$R_{10}$ is H or $C_{1-6}$alkyl optionally substituted with phenyl, OH, $C_{1-3}$alkoxy or $NR_{11}R_{12}$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$; and n is 0–3.

Yet another embodiment of the compounds of formula (XVIII) are those described immediately above, wherein:

$Ar_1$ is phenyl or pyridyl, each optionally substituted by one or more $R_1$, $R_2$ and $R_3$;

R is H or $C_{1-3}$alkyl;

$R_1$ and $R_2$ are the same or different and selected from: halogen, $C_{1-3}$ alkyl, wherein the $C_{1-3}$ alkyl is optionally partially or fully halogenated, $NO_2$ or $NR_8R_9$;

$R_3$ is H, halogen, methyl or methoxy;

$R_4$ is H, $C_{1-3}$alkyl branched or unbranched, saturated or unsaturated, and optionally substituted with OH; or $R_4$ is $(CH_2)_{2-3}NR_8R_9$ or $CO_2R_{10}$;

$R_8$ and $R_9$ are the same or different and are each independently selected from H, $C_{1-3}$alkyl branched or unbranched, $CO_2R_{10}$, phenyl, or benzoyl; wherein said alkyl, phenyl or benzoyl are optionally substituted with OH or $C_{1-3}$alkoxy;

or $R_8$ and $R_9$ together form a —$(CH_2)_2$—$N(CO_2R_{10})$—$(CH_2)_2$— group or a —$(CH_2)_2$—$N(R_{11})$—$(CH_2)_2$— group; and wherein said ring is optionally substituted by $C_{1-3}$ alkyl, $C_{1-3}$alkoxy, or OH;

$R_{10}$ is H or $C_{1-3}$alkyl optionally substituted with phenyl, OH, $C_{1-3}$alkoxy or $NR_{11}R_{12}$;

$R_{11}$ and $R_{12}$ are each independently selected from H and $C_{1-3}$ alkyl optionally substituted with $C_{1-3}$alkoxy or OH;

or $R_{11}$ and $R_{12}$ together form a chain completing a ring, said chain is $(CH_2)_{4-5}$ or $(CH_2)_2O(CH_2)_2$.

Formula (XIX)

In their broadest generic aspect, intermediate compounds of formula (XIX) are represented by the following formula:

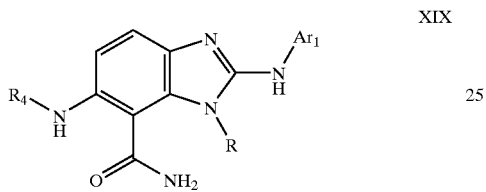

XIX wherein: $Ar_1$ is an aromatic or nonaromatic carbocycle, heteroaryl or heterocycle; wherein said carbocycle, heteroaryl or heterocycle is optionally substituted by one or more $R_1$, $R_2$ and $R_3$;

R is H, $C_{1-3}$alkyl or cyclopropyl $R_1$ and $R_2$ are the same or different and are selected from H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, di-($C_{1-3}$) alkylaminosulfonyl, $NR_8R_9$, aryl, aroyl, aryloxy, arylsulfonyl, heteroaryl and heteroaryloxy; wherein the abovementioned $R_1$ and $R_2$ are optionally partially or fully halogenated or optionally substituted with one to three groups independently selected from the group consisting of oxo, OH, $NR_8R_9$, $C_{1-6}$branched or unbranched alkyl, $C_{3-7}$cycloalkyl, phenyl, naphthyl, heteroaryl, aminocarbonyl and mono- or di($C_{1-3}$) alkylaminocarbonyl;

$R_3$ is selected from the group consisting of H, halogen, OH, $(CH_2)_nNR_8R_9$, $(CH_2)_nCO_2R_{10}$, $C_{1-3}$alkyl optionally substituted with OH, $C_{1-3}$ alkoxy optionally halogenated and $C_{1-3}$ alkylthio;

$R_4$ is selected from H, $C_{1-6}$ alkyl branched or unbranched, saturated or unsaturated, and optionally substituted with phenyl, OH or $C_{1-3}$alkoxy, $C_{3-10}$-cycloalkyl, or $C_{5-8}$cycloalkenyl;

or $R_4$ is selected from $(CH_2)_mNR_8R_9$, $(CH_2)_mNR_8COR_{10}$, $(CH_2)_nCO_2R_0$, $(CH_2)_nCONR_8R_9$ phenyl, heteroaryl or heterocycle, each phenyl, heteroaryl or heterocycle being optionally substituted with $C_{1-3}$alkyl, $C_{1-3}$alkoxy, $(CH_2)_mNR_8R_9$, OH, $SO_3H$ or halogen;

$R_8$ and $R_9$ are the same or different and are each independently selected from H, OH, $CO_2R_{10}$, $C_{1-10}$ acyl branched or unbranched, $C_{1-3}$alkoxy, $C_{1-6}$alkyl branched or unbranched, $C_{3-6}$alkenyl, $C_{3-8}$cycloalkyl, aryl, aryl$C_{1-3}$alkyl, aroyl, heteroaryl or heterocycle; wherein said alkyl, cycloalkyl, aryl, aryl$C_{1-3}$alkyl, aroyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl;

or $R_8$ and $R_9$ together form a 3–7 member alkylene chain completing a ring about the N atom to which they are attached; wherein said alkylene chain is optionally interrupted by O, $S(O)_p$, $NCOR_{10}$, $NCO_2R_{10}$, $NR_{11}$ or $NC(=NR_{11})NR_{11}R_{12}$; and wherein said ring is optionally substituted by $C_{1-3}$ alkyl, $C_{1-3}$alkoxy, OH or —$(CH_2)_nNR_{11}R_{12}$;

$R_{10}$ is selected from H, $C_{1-6}$alkyl, $C_{3-8}$cycloalkyl, wherein each alkyl or cycloalkyl is optionally substituted with phenyl, OH, $C_{1-3}$alkoxy, $C_{1-3}$alkanoyloxy or $NR_{11}R_{12}$, or $R_{10}$ is phenyl optionally substituted with one to three $C_{1-3}$alkyl, $C_{1-3}$alkoxy, halogen, $(CH_2)_mNR_8R_9$, $(CH_2)_nCON_8R_9$ or $O(CH_2)_{2-4}NR_8R_9$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$;

m is 1–4;

n is 0–3;

and p is 0–2;

wherein one or more of the primary amine or secondary amine nitrogen atoms in any of the $R_4$, $R_5$, $R_6$ and $R_7$ substituent groups may optionally be protected by a protecting group.

One embodiment of the compounds of formula (XIX) above is wherein:

$Ar_1$ is a) a cycloalkyl group selected from cyclopropyl, cyclobutyl, cyclopentanyl, cyclohexanyl and cycloheptanyl;

b) a cycloalkenyl group selected from cyclopentenyl, cyclohexenyl, and cycloheptenyl;

c) an aromatic carbocycle selected from phenyl, naphthyl, indanyl, indenyl, dihydronaphthyl, tetrahydronaphthyl or fluorenyl, d) a heteroaryl selected from pyridyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl, or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or e) a heterocycle selected from: pyrrolinyl, pyrrolidinyl, pyrazolinyl, pyrazolidinyl, piperidinyl, morpholinyl, thiomorpholinyl, pyranyl, thiopyranyl, piperazinyl and indolinyl;

wherein each of the above $Ar_1$ are optionally substituted by one or more $R_1$, $R_2$ and $R_3$;

$R_1$ and $R_2$ are as defined in claim 1, and $R_3$ is hydrogen, halogen, methyl, methoxy, hydroxymethyl or OH; and $R_4$ is H, $C_{1-3}$alkyl branched or unbranched, saturated or unsaturated, and optionally substituted with OH; or $R_4$ is $(CH_2)_{2-3}NR_8R_9$, $(CH_2)_nCO_2R_{10}$ or $(CH_2)_nCONR_8R_9$;

$R_8$ and $R_9$ are the same or different and are each independently selected from H, OH, $C_{1-3}$alkyl branched or unbranched, $CO_2R_{10}$, $C_{3-8}$cycloalkyl, phenyl, benzyl, benzoyl, heteroaryl or heterocycle; wherein said alkyl, cycloalkyl, phenyl, benzyl, benzoyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl;

or $R_8$ and $R_9$ together form a 4–6 member alkylene chain completing a ring about the N atom to which they are attached; wherein said alkylene chain is optionally interrupted by $NCO_2R_{10}$ or $NR_{11}$; and wherein said ring is optionally substituted by $C_{1-3}$ alkyl, $C_{1-3}$alkoxy, OH or —$(CH_2)_nNR_{11}R_{12}$;

$R_{10}$ is H or $C_{1-6}$alkyl optionally substituted with phenyl, OH, $C_{1-3}$alkoxy or $NR_{11}R_{12}$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$; and n is 0–3.

Yet another embodiment of the compounds of formula (XIX) are those described immediately above, wherein:

$Ar_1$ is phenyl or pyridyl, each optionally substituted by one or more $R_1$, $R_2$ and $R_3$;

R is H or $C_{1-3}$alkyl;

$R_1$ and $R_2$ are the same or different and selected from: halogen, $C_{1-3}$ alkyl, wherein the $C_{1-3}$ alkyl is optionally partially or fully halogenated, $NO_2$ or $NR_8R_9$;

$R_3$ is H, halogen, methyl or methoxy;

$R_4$ is H, $C_{1-3}$alkyl branched or unbranched, saturated or unsaturated, and optionally substituted with OH; or $R_4$ is $(CH_2)_{2-3}NR_8R_9$ or $CO_2R_{10}$;

$R_8$ and $R_9$ are the same or different and are each independently selected from H, $C_{1-3}$alkyl branched or unbranched, $CO_2R_{10}$, phenyl, or benzoyl; wherein said alkyl, phenyl or benzoyl are optionally substituted with OH or $C_{1-3}$alkoxy;

or $R_8$ and $R_9$ together form a —$(CH_2)_2$—$N(CO_2R_{10})$—$(CH_2)_2$— group or a —$(CH_2)_2$—$N(R_{11})$—$(CH_2)_2$— group; and wherein said ring is optionally substituted by $C_{1-3}$ alkyl, $C_{1-3}$alkoxy, or OH;

$R_{10}$ is H or $C_{1-3}$alkyl optionally substituted with phenyl, OH, $C_{1-3}$alkoxy or $NR_{11}R_{12}$;

$R_{11}$ and $R_{12}$ are each independently selected from H and $C_{1-3}$ alkyl optionally substituted with $C_{1-3}$alkoxy or OH;

or $R_{11}$ and $R_{12}$ together form a chain completing a ring, said chain is $(CH_2)_{4-5}$ or $(CH_2)_2O(CH_2)_2$.

In a further embodiment of the invention, there are provided the following compounds of the formula (I):

2-(2,6-Dichlorophenylamino)-1-methyl-1,8-dihydro-9H-imidazo[4,5-f]quinazoline-9-one;

2-(2,6-Dichlorophenylamino)-7-furan-2-yl-1-methyl-1,8-dihydro-9H-imidazo[4,5-f]quinazoline-9-one;

2-(2,6-Dichlorophenylamino)-1-methyl-7-phenyl-1,8-dihydro-9H-imidazo[4,5-f]quinazoline-9-one;

2-(2,6-Dichlorophenylamino)-1-methyl-7-(3-nitrophenyl)-1,8-dihydro-9H-imidazo[4,5-f]quinazoline-9-one;

7-(3-Aminophenyl)-2-(2,6-dichlorophenylamino)-1-methyl-1,8-dihydro-9H-imidazo[4,5-f]quinazoline-9-one;

1-{3-[2-(2,6-Dichlorophenylamino)-1-methyl-9-oxo-1,8,-dihydro-9H-imidazo[4,5-f]quinazolin-7-yl]-phenyl}-3-ethylurea;

2-(2,6-Dichlorophenylamino)-1-methyl-7-vinyl-1,8-dihydro-9H-imidazo[4,5-f]quinazoline-9-one;

2-(2,6-Dichlorophenylamino)-1-methyl-7-thiophen-2-yl-1,8-dihydro-9H-imidazo[4,5-f]quinazoline-9-one;

2-(2,6-Dichlorophenylamino)-1-methyl-7-[2-(3-nitrophenyl)-thiazol-4-yl]-1,8-dihydro-9H-imidazo[4,5-f]quinazoline-9-one;

2-(2,6-Dichlorophenylamino)-7-imidazol-2-yl-1-methyl-1,8-dihydro-9H-imidazo[4,5-f]quinazoline-9-one;

2-(2,6-Dichlorophenylamino)-1-methyl-7-(2-phenyloxazol-5-yl)-1,8-dihydro-9H-imidazo[4,5-f]quinazoline-9-one;

2-(2,6-Dichlorophenylamino)-1-methyl-9-oxo-1,8,-dihydro-9H-imidazo[4,5-f]quinazoline-7-carboxamide;

2-(2,6-Dichlorophenylamino)-1-methyl-7-(2-methylpropen-1-yl)-1,8-dihydro-9H-imidazo[4,5-f]quinazoline-9-one;

2-(2,6-Dichlorophenylamino)-1-methyl-7-pyridin-2-yl-1,8-dihydro-9H-imidazo[4,5-f]quinazoline-9-one;

2-(2,6-Dichlorophenylamino)-1-methyl-7-pyridin-3-yl-1,8-dihydro-9H-imidazo[4,5-f]quinazoline-9-one;

2-(2,6-Dichlorophenylamino)-1-methyl-1H-imidazo[4,5-f]quinazoline-7,9-6H,8H-dione;

4,5-f]quinazoline-9-one;

7-Cyclopent-1-enyl-2-(2,6-dichlorophenylamino)-1-methyl-1,8-dihydro-9H-imidazo[4,5-f]quinazoline-9-one;

7-[2-(3-Aminophenyl)-thiazol-4-yl]-2-(2,6-dichlorophenylamino)-1-methyl-1,8-dihydro-9H-imidazo[4,5-f]quinazoline-9-one;

Ethyl 2-(2,6-Dichlorophenylamino)-1-methyl-9-oxo-1,8,-dihydro-9H-imidazo[4,5-f]quinazoline-7-carboxylate;

7-Benzofuran-2-yl-2-(2,6-dichlorophenylamino)-1-methyl-1,8-dihydro-9H-imidazo[4,5-f]quinazoline-9-one;

2-(2,6-Dichlorophenylamino)-1-methyl-7-(1-methylprop-1-enyl)-1,8-dihydro-9H-imidazo[4,5-f]quinazoline-9-one;

2-(2,6-Dichlorophenylamino)-1-methyl-7-(2-methyloxazol-5-yl)-1,8-dihydro-9H-imidazo[4,5-f]quinazoline-9-one;

2-(2,6-Dichlorophenylamino)-7-(1H-indole-3-carbonyl)-1-methyl-1,8-dihydro-9H-imidazo[4,5-f]quinazoline-9-one;

2-(2,6-Dichlorophenylamino)-1-methyl-7-(3-piperazin-1-yl-cyclopent-1-enyl)-1,8-dihydro-9H-imidazo[4,5-f]quinazoline-9-one;

7-Cyclohex-1-enyl-2-(2,6-dichlorophenylamino)-1-methyl-1,8-dihydro-9H-imidazo[4,5-f]quinazoline-9-one;

2-(2,6-Dichlorophenylamino)-1-methyl-7-(1-methyl-1,2,5,6-tetrahydro-pyridin-3-yl)-1,8-dihydro-9H-imidazo[4,5-f]quinazoline-9-one;

2-(2,6-Dichlorophenylamino)-1-methyl-7-[5-(2-nitrophenyl)-furan-2-yl]-1,8-dihydro-9H-imidazo[4,5-f]quinazoline-9-one;

2-(2,6-Dichlorophenylamino)-7-furan-3-yl-1-methyl-1,8-dihydro-9H-imidazo[4,5-f]quinazoline-9-one;

7-(5-Bromofuran-2-yl)-2-(2,6-dichlorophenylamino)-1-methyl-1,8-dihydro-9H-imidazo[4,5-f]quinazoline-9-one;

2-(2,6-Dichlorophenylamino)-1-methyl-7-(3-methylfuran-2-yl)-1,8-dihydro-9H-imidazo[4,5-f]quinazoline-9-one;

7-Cyclopropyl-2-(2,6-dichlorophenylamino)-1-methyl-1,8-dihydro-9H-imidazo[4,5-f]quinazoline-9-one;

2-(2,6-Dichlorophenylamino)-1-methyl-7-[3-(4-methylpiperazine-1-sulfonyl)-phenyl]-1,8-dihydro-9H-imidazo[4,5-f]quinazoline-9-one;

4-{3-[2-(2,6-Dichlorophenylamino)-1-methyl-9-oxo-1,8,-dihydro-9H-imidazo[4,5-f]quinazolin-7-yl]-cyclopent-2-enyl}-piperazine-1-carboxylic acid tert-butyl ester;

2-(2,6-Dichlorophenylamino)-7-(3-hydroxycyclopent-1-enyl)-1-methyl-1,8-dihydro-9H-imidazo[4,5-f]quinazoline-9-one;

2-(2,6-Dichlorophenylamino)-1-methyl-7-[3-(piperazine-1-sulfonyl)-phenyl]-1,8-dihydro-9H-imidazo[4,5-f]quinazoline-9-one;

3-[2-(2,6-Dichlorophenylamino)-1-methyl-9-oxo-1,8,-dihydro-9H-imidazo[4,5-f]quinazolin-7-yl]-cyclopent-3-enecarbonitrile;

7-Amino-2-(2,6-dichlorophenylamino)-1-methyl-1,8-dihydro-9H-imidazo[4,5-f]quinazoline-9-one;

3-{2-[2-(2,6-Dichlorophenylamino)-1-methyl-9-oxo-1,8,-dihydro-9H-imidazo[4,5-f]quinazolin-7-yl]-propenyl}-benzonitrile;

3-[2-(2,6-Dichlorophenylamino)-1-methyl-9-oxo-1,8,-dihydro-9H-imidazo[4,5-f]quinazolin-7-yl]-cyclopent-3-enecarboxamide;

2-{4-[2-(2,6-Dichlorophenylamino)-1-methyl-9-oxo-1,8,-dihydro-9H-imidazo[4,5-f]quinazolin-7-yl]-thiazol-2-yl}-pyrrolidine-1-carboxylic acid benzyl ester;

2-(2,6-Dichlorophenylamino)-1-methyl-7-[1-methyl-2-(3-nitrophenyl)-vinyl]-1,8-dihydro-9H-imidazo[4,5-f]quinazoline-9-one;

3-{4-[2-(2,6-Dichlorophenylamino)-1-methyl-9-oxo-1,8,-dihydro-9H-imidazo[4,5-f]quinazolin-7-yl]-thiazol-2-ylmethyl}-piperidine-1-carboxylic acid benzyl ester;

7-[2-(2-Aminocyclohexyl)-thiazol-4-yl]-2-(2,6-dichlorophenylamino)-1-methyl-1,8-dihydro-9H-imidazo[4,5-f]quinazoline-9-one;

2-(2,6-Dichlorophenylamino)-1-methyl-7-(2-piperidin-3-ylmethyl-thiazol-4-yl)-1,8-dihydro-9H-imidazo[4,5-f]quinazoline-9-one;

2-(2,6-Dichlorophenylamino)-1-methyl-7-(2-methylthiazol-4-yl)-1,8-dihydro-9H-imidazo[4,5-f]quinazoline-9-one;

2-(2,6-Dichlorophenylamino)-1-methyl-7-(3-oxocyclopent-1-enyl)-1,8-dihydro-9H-imidazo[4,5-f]quinazoline-9-one;

3-[2-(2,6-Dichlorophenylamino)-1-methyl-9-oxo-1,8,-dihydro-9H-imidazo[4,5-f]quinazolin-7-yl]-2,5-dihydro-pyrrole-1-carboxylic acid tert-butyl ester;

7-[2-(3-Aminophenyl)-1-methylvinyl]-2-(2,6-dichlorophenylamino)-1-methyl-1,8-dihydro-9H-imidazo[4,5-f]quinazoline-9-one;

Acetic acid 2-(4-{3-[2-(2,6-Dichlorophenylamino)-1-methyl-9-oxo-1,8,-dihydro-9H-imidazo[4,5-f]quinazolin-7-yl]-benzenesulfonyl}-piperazin-1-yl)-2-oxoethyl ester;

2-(2,6-Dichlorophenylamino)-7-(2,5-dihydro-1H-pyrrol-3-yl)-1-methyl-1,8-dihydro-9H-imidazo[4,5-f]quinazoline-9-one;

7-[2-(3-Aminomethylphenyl)-1-methylvinyl]-2-(2,6-dichlorophenylamino)-1-methyl-1,8-dihydro-9H-imidazo[4,5-f]quinazoline-9-one;

4-{3-[2-(2,6-Dichlorophenylamino)-1-methyl-9-oxo-1,8,-dihydro-9H-imidazo[4,5-f]quinazolin-7-yl]-benzenesulfonyl}-piperazine-1-carboxamidine;

2-(2,6-Dichlorophenylamino)-7-{3-[4-(2-hydroxyacetyl)-piperazine-1-sulfonyl]-phenyl}1-methyl-1,8-dihydro-9H-imidazo[4,5-f]quinazoline-9-one;

3-{2-[2-(2,6-Dichlorophenylamino)-1-methyl-9-oxo-1,8,-dihydro-9H-imidazo[4,5-f]quinazolin-7-yl]-propenyl}-benzamidine;

7-(7-Azabicyclo[2.2.1]hepta-2,5-dien-2-yl)-2-(2,6-dichlorophenylamino)-1-methyl-1,8-dihydro-9H-imidazo[4,5-f]quinazoline-9-one;

5-[2-(2,6-Dichlorophenylamino)-1-methyl-9-oxo-1,8,-dihydro-9H-imidazo[4,5-f]quinazolin-7-yl]-3,3a,4,6a-tetrahydro-1H-cyclopenta[c]pyrrole-2-carboxylic acid tert-butyl ester;

2-(2,6-Dichlorophenylamino)-7-(1,2,3,3a,4,6a-hexahydro-cyclopenta[c]pyrrol-5-yl)-1-methyl-1,8-dihydro-9H-imidazo[4,5-f]quinazoline-9-one;

2-(2,6-Dichlorophenylamino)-1-methyl-7-(2-pyrrolidin-2yl-thiazol-4-yl)-1,8-dihydro-9H-imidazo[4,5-f]quinazoline-9-one;

7-[2-(3,5-Diaminophenyl)-1-methylvinyl]-2-(2,6-dichlorophenylamino)-1-methyl-1,8-dihydro-9H-imidazo[4,5-f]quinazoline-9-one; and 2-(2,6-Dichlorophenylamino)-1-methyl-7-[4-(piperazine-1-sulfonyl)-phenyl]-1,8-dihydro-9H-imidazo[4,5-f]quinazoline-9-one; and the pharmacuetically acceptable derivatives thereof.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, a compound which would have a 'dangling valency', or a 'carbanion' are not compounds contemplated by the invention.

All terms as used herein in this specification, unless otherwise stated, shall be understood in their ordinary meaning as known in the art. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched or unbranched unless otherwise specified. Other more specific definitions are as follows:

The term "halogen" as used in the present specification shall be understood to mean bromine, chlorine, fluorine or iodine.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Example "heteroaryl" radicals include, pyridyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl,or a fused heteroaryl such as cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene;

The term "heterocycle" refers to a stable 5–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached to the main structure by any atom of the cycle, which results in the creation of a stable structure. Example "heterocycle" radicals include pyrrolinyl, pyrrolidinyl, pyrazolinyl, pyrazolidinyl, 1,2,5,6-tetrahydropyridinyl, piperidinyl, morpholinyl, thiomorpholinyl, pyranyl, thiopyranyl, piperazinyl, indolinyl, and 1,2,3,3a,4,6a-hexahydro-cyclopenta[c]pyrrolyl.

As used herein and throughout this specification, the terms "nitrogen" and "sulfur" and their respective elements symbols include any oxidized form of nitrogen and sulfur and the quaternized form of any basic nitrogen.

The term "aryl" shall be understood to mean a 6–10 membered aromatic carbocycle, "aryl" includes, for example, phenyl and naphthyl; other terms comprising "aryl" will have the same definition for the aryl component, examples of these moieties include: arylalkyl, aryloxy or arylthio.

The term "carbocycle" shall be understood to mean a 3–10 membered aromatic or nonaromatic cyclic carbon chain. Examples of nonaromatic carbocycles include cycloalkyl groups such as cyclopropyl, cyclobutyl, cyclopentyl; cycloalkylidene groups such as cyclopentylidene, cyclohexylidene; and cycloalkenyl groups such as cyclopentenyl, cyclohexenyl and cycloheptenyl. Examples of aromatic carbocycles include the "aryl" compounds as described hereinabove.

The "$C_{6-12}$ bridged- or spiro-bicyclic ring system, optionally having one or two double bonds in the ring system, and wherein up to 3 carbon atoms in the ring system may be replaced by heteroatoms selected from N, O and S" in the $R_5$ definition shall be understood to mean any ring system containing 6 to 12 carbon atoms and having at least one bridged-type or spiro-type fusion within the ring system, wherein up to 3 of the aforementioned carbon atoms may optionally be replaced by a heteroatom independently selected from N, O and S. An example is a $C_{6-10}$-, preferably, $C_{6-7}$- bridged-bicyclic ring system, optionally having one or two double bonds in the system, wherein up to 2, preferably up to 1, carbon atoms in the ring system are replaced by a nitrogen atom. An example of such a ring system is 7-azabicyclo[2.2.1]hept-2,5-diene. Other examples within the broad definition include norbornenyl, tropanyl, 1-azabicyclo[2.2.2]oct-2-enyl, 7-azabicyclo[3.2.1]oct-6-enyl, spiro[4.5]dec-1-enyl, and spiro[4.4]non-1-enyl.

The term "acyl" shall be understood to mean an R—(C=O)— moiety wherein R is an alkyl. Examples of R can be a $C_{1-10}$alkyl, saturated or unsaturated, branched or unbranched, or R can be "aryl" as defined hereinabove. An example when R is an aryl is the benzoyl group or $C_6H_5$—CO. "Acyloxy" shall be understood to mean an R—$CO_2$—group wherein R is as defined in this paragraph.

As indicated above, one or more of the primary amine or secondary amine nitrogen atoms in any of the $R_4$, $R_5$, $R_6$ and $R_7$ substituent groups may optionally be protected by a protecting group. Suitable protecting groups for this purpose, for example, are those disclosed in T. W. Greene and P. G. M. Wuts, "Protective Groups in Organic Synthesis", Wiley, New York, 1990. Examples of suitable protecting groups for this purpose include benzyloxycarbonyl, tert-butyloxycarbonyl, allyloxycarbonyl, acetyl and trifluoroacetyl. The invention includes pharmaceutically acceptable derivatives of compounds of the invention. A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not them selves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal ( e.g., magnesium), ammonium and N—($C_1$–$C_4$ alkyl)$_4^+$ salts.

In addition, the compounds of this invention include prodrugs of compounds of the invention. Prodrugs include t hose compounds that, upon simple chemical transformation, are modified to produce a compound of the invention. Simple chemical transformations include hydrolysis, oxidation and reduction, enzymatically, metabolically or otherwise. Specifically, when a prodrug of this invention is administered to a patient, the prodrug may be transformed into a compound of the invention, thereby imparting the desired pharmacological effect.

General Synthetic Methods

The compounds of the invention may be prepared by the methods described below. In each of the schemes below, the groups $R_4$, $R_5$, $R_6$, $R_7$, $R_9$ and $Ar_1$ are as defined above for general formula I except as noted. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. Intermediates and products may be purified by chromatography on silica gel and/or recrystallization. Starting materials and reagents are either commercially available or may be prepared by one skilled in the art using methods described in the chemical literature.

Compounds of formula (I) in which Het is the dione shown in formula (Ia) (Scheme 1) may be prepared as illustrated in Scheme 1 and described below (Method A).

Scheme 1 (Method A)

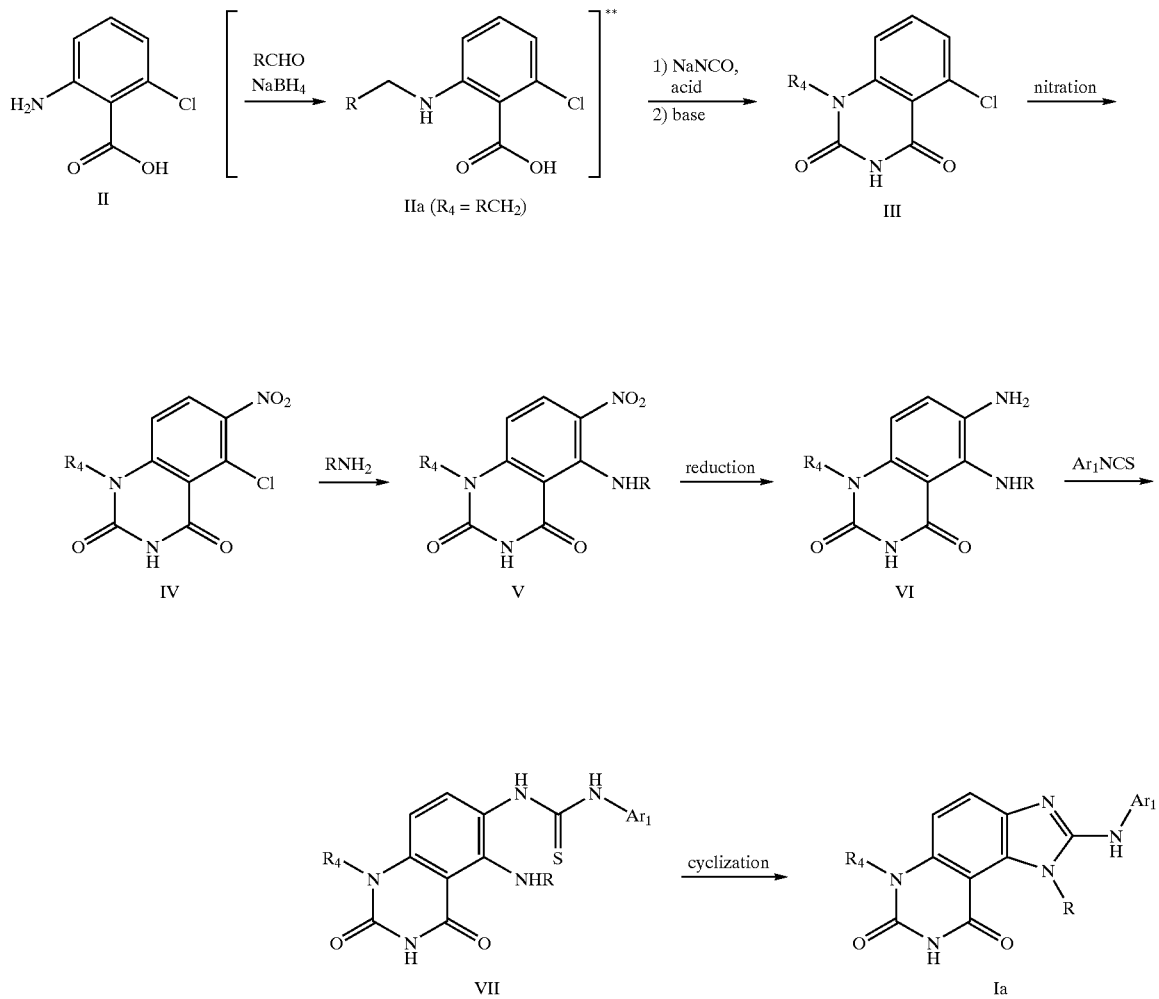

**preliminary step II → IIa for when $R_4$ is not H

6-Chloroanthranilic acid (II) is reacted with sodium cyanate in the presence of a suitable acid, such as acetic acid, followed by a suitable base such as sodium hydroxide. Following an acidic work-up, the quinazolinedione III is isolated. In cases where $R_4$ is not H, one may react II ($R_4$=H) with an appropriate aldehyde (RCHO) in the presence of a suitable reducing agent, such as sodium borohydride to provide IIa ($R_4$=$RCH_2$).

Intermediate III is then subjected to nitration conditions, for example treatment with nitric acid in the presence of sulfuric acid to provide IV. Intermediate IV is then treated with excess amine $RNH_2$ (R=H, $C_{1-3}$ alkyl or cyclopropyl) in a suitable solvent, such as n-butanol, preferably in a sealed vessel with heating at about 50 to 150° C., to provide V.

Reduction of V, for example by treatment with hydrogen preferably at 10–60 psi in the presence of a suitable catalyst such as 10% Pd/c, provides VI. Treatment of VI with the desired isothiocyanate ($Ar_1NCS$), in a suitable solvent such as DMF provides thiourea (VII). Cyclization of VII may be accomplished by treatment with a suitable coupling reagent, such as dicyclohexylcarbodiimide or mercury oxide in a suitable solvent such as THF or DMF to provide the desired compound Ia.

Compounds of formula (I) in which Het is substituted with $R_5$ as shown in formula (Ib) (Scheme 2) may be prepared as illustrated in Scheme 2 and described below (Method B).

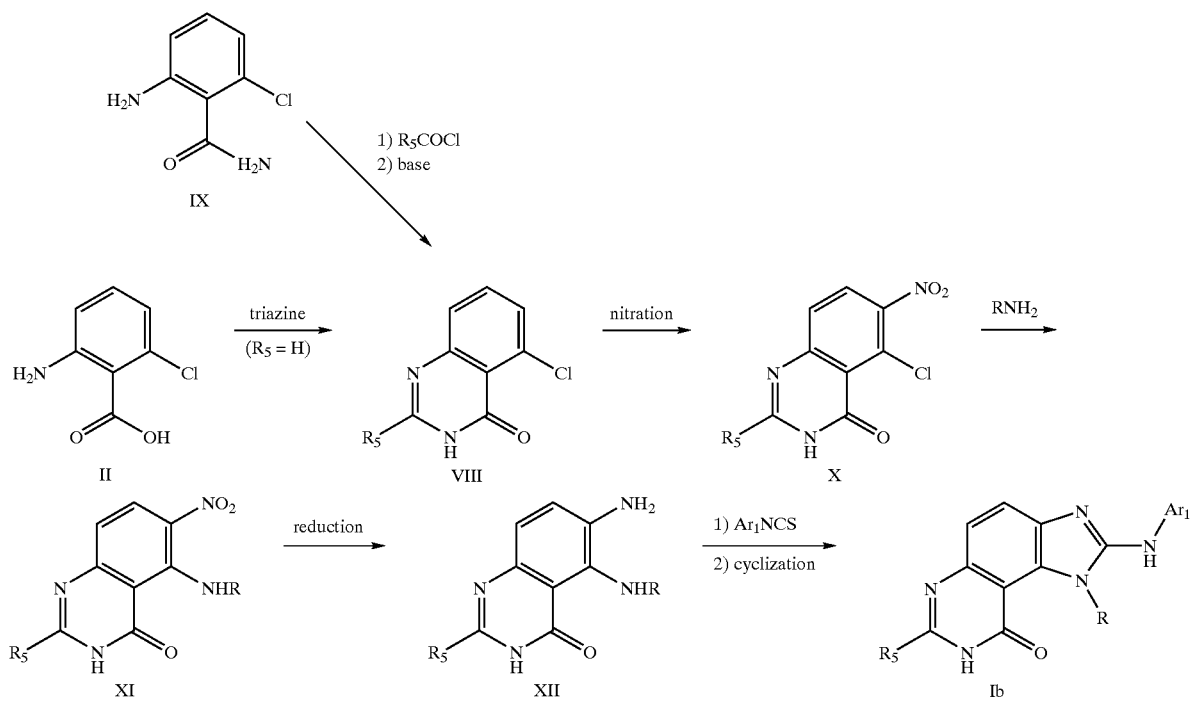

In cases where $R_5$ is H, one may treat 6-chloroanthranilic acid (II) with triazine in a suitable solvent, such as EtOH, in the presence of a suitable base such as piperidine, preferably while heating at about the reflux temperature of the solvent to provide the quinazolinone VIII ($R_5$=H). to obtain compounds where $R_5$ is not H, one may react the amide IX with an acid chloride $R_5$ COCl, in a suitable solvent, such as THF, in the presence of a suitable base, such as triethylamine to provide an intermediate amide which is cyclized to VIII by treatment with a suitable base, for example sodium methoxide in methanol, preferably at reflux temperature. Intermediate VIII may then be converted to Ib by the same general procedure described in Method A for a converting III to Ia.

The preparation of benzimidazole intermediates, which may be used in alternate procedures to prepare compounds of formula (I) is illustrated in Scheme 3 and described below (Method C):

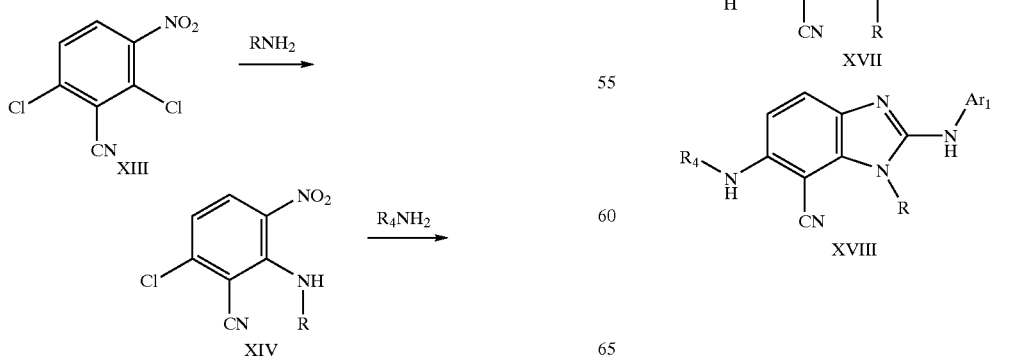

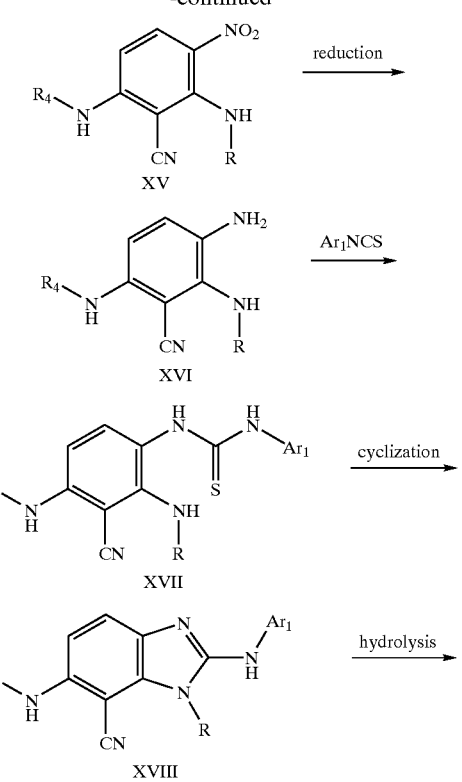

-continued

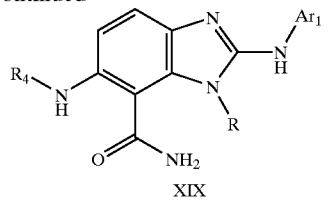
XIX 2,6-Dichloro-3-nitrobenzonitrile (XIII) is treated with the desired amine RNH$_2$ (R=H, C$_{1-3}$ alkyl or cyclopropyl) in a suitable solvent such as THF or EtOAc to provide XIV. This intermediate is then treated with R$_4$NH$_2$ in a suitable solvent such as EtOH, preferably in a sealed vessel while heating at about 50–110° C. to provide XV. Reduction to XVI, formation of thiourea XVII and cyclization to benzimidazole XVIII may be carried out as described for the conversion of V to Ia in Method A. Hydrolysis of the nitrile, for example, by treatment with concentrated H$_2$SO$_4$ at about 100° C., provides XIX.

Method D (Scheme 4) illustrates how one may prepare compounds of formula (Ib) from intermediate XVIII (R$_4$=H).

Scheme 4 (Method D)

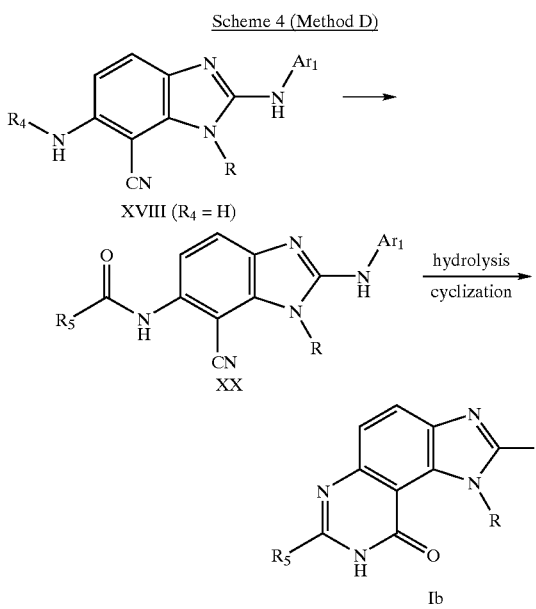

Treatment of XVIII (R$_4$=H) with an acid halide R$_5$COX (where X is a halogen) or acid anhydride (R$_5$CO)$_2$O or with an acid R$_5$CO$_2$H and a coupling reagent such as dicyclohexylcarbodiimide or 1-[3-(dimethylamino)propyl]-3-ethylcarbodiimide, in a suitable solvent, such as THF or DMF, in the presence of a suitable base such as triethylamine or 4-(dimethylamino)pyridine provides amide XX.

Hydrolysis of the nitrile, followed by cyclization to Ib may be achieved, for example, by treatment of XX with a suitable base, such as aqueous sodium hydroxide, and an oxidant such as hydrogen peroxide or sodium perborate in a suitable solvent such as dioxane.

Intermediate XIX (R$_4$=H) may be used to prepare compounds of formula (Ib) as outlined in Scheme 5 (Method E):

Scheme 5 (Method E)

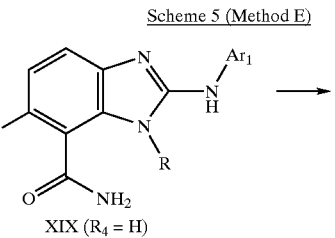

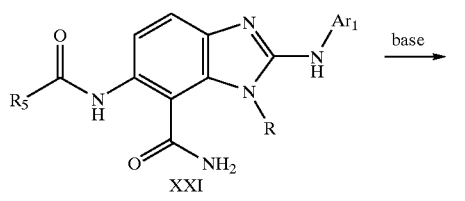

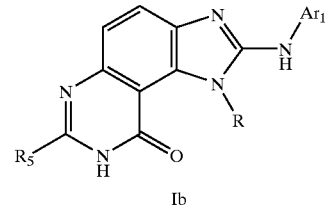
Ib

Formation of XXI may be accomplished as described above for conversion of XVIII to XX. Intermediate XXI may then by cyclized by treatment with a suitable base such as sodium methoxide or potassium t-butoxide in a suitable solvent such as MeOH or THF, respectively, at about reflux temperature to provide Ib.

Intermediate XIX may also be used to prepare compounds of formula (Ia) as illustrated in Scheme 6 (Method F).

Scheme 6 (Method F)

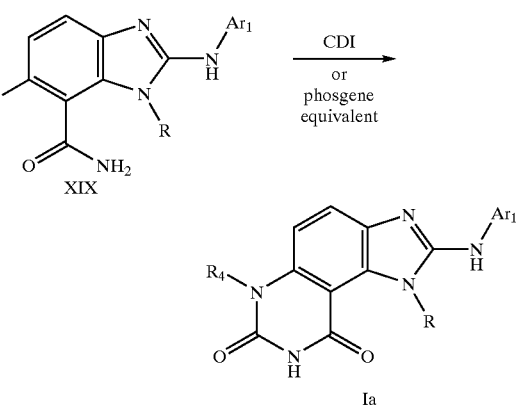

Treatment of XIX with carbonyldiimidazole (CDI) or a phosgene equivalent in a suitable solvent such as THF provides Ia.

Compounds of formula (I) in which Het is partially saturated may be prepared from intermediate XIX, as illustrated in Scheme 7 (Method G).

Scheme 7 (Method G)

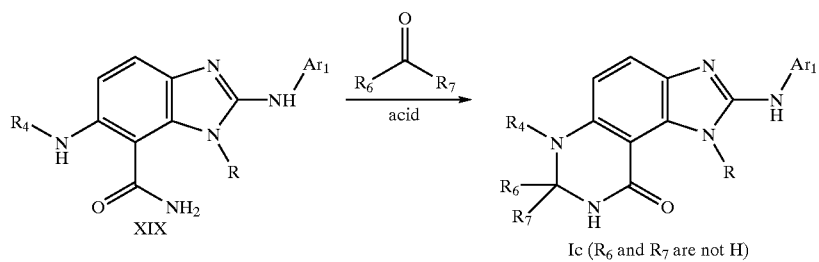

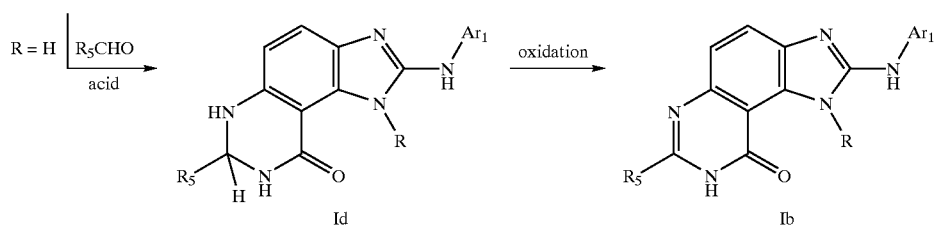

Treatment of XIX with a ketone ($R_6C(O)R_7$, where $R_6$ and $R_7$ are not H) in the presence of a catalytic amount of an acid such as p-TsOH, in a suitable solvent such as THF provides Ic ($R_6$ and $R_7$ are not H). When $R_4$=H, the use of an aldehyde ($R_5CHO$) instead of a ketone provides Id. This compound may be oxidized to Ib by treatment with a suitable oxidizing agent such as $MnO_2$ or dichlorodicyanobenzoquinone.

Compounds of formula (Ib) where $R_5$=$NHR_9$, represented by formula (Ib') below, may be prepared from intermediate XIX (where $R_4$=H) by Method H as illustrated in Scheme 8.

Scheme 8 (Method H)

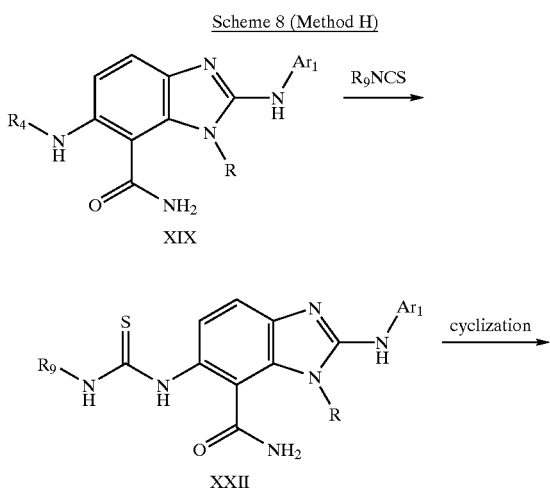

-continued

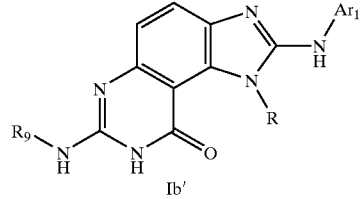

Reaction of XIX with an isothiocyanate in a suitable solvent such as DMF or THF provides thiourea XXII. Cyclization or XXII may be accomplished by the addition of a suitable condensing agent such as mercury oxide to produce the desired product of formula (Ib').

Scheme 9 (Method I) illustrates a procedure by which compounds of formula (I) with X=S may be prepared. Intermediate XXV may be prepared from XXIII by reaction with an acid chloride ($R_5C(O)Cl$) to form an intermediate amide, followed by cyclization by treating with a suitable base such as sodium methoxide. Alternatively, if $R_5$=H one may react XXIV with triazine in a suitable solvent such as EtOH, in the presence of a suitable base such as piperidine to produce XXV ($R_5$=H). Reduction of the nitro group to give XXVI and formation of thiourea XXVII may be accomplished by procedures described in the above Methods. Cyclization of XXVII to give I (X=S) may be achieved by treatment with bromine in a suitable solvent such as $CHCl_3$.

Scheme 9 (Method I)

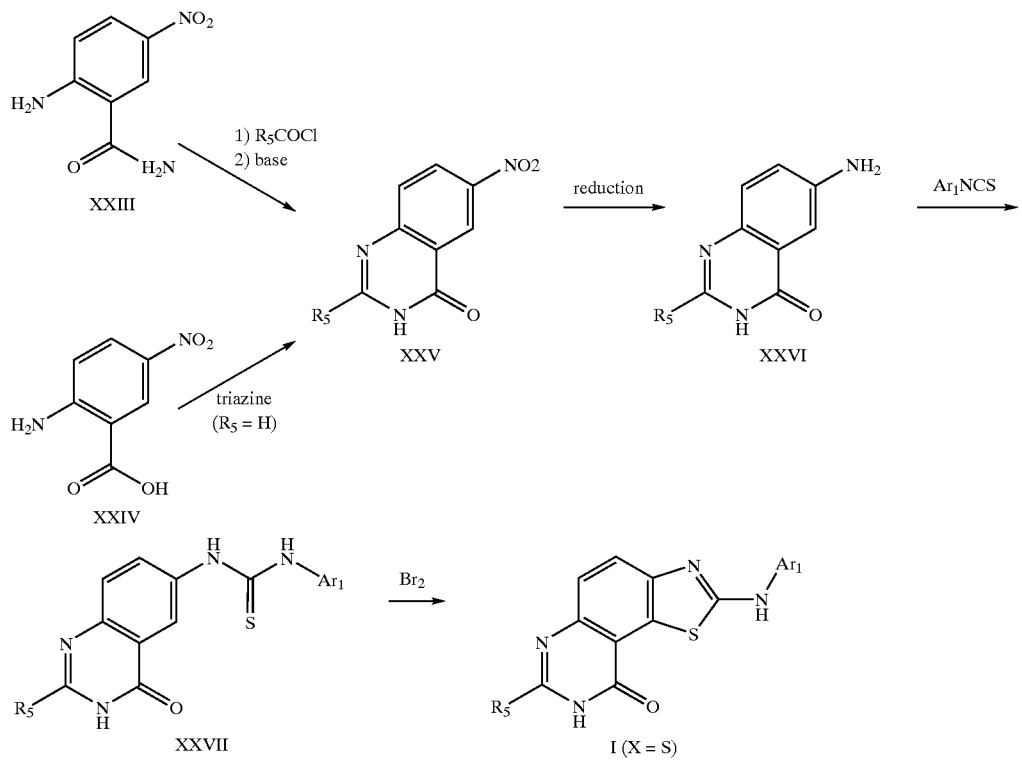

Several of these transformations are also exemplified below.

Methods of Therapeutic Use

The compounds of the invention are useful in inhibiting the activity of src-family kinases and PDGFR kinase. In doing so, the compounds are effective in blocking disease processes mediated by these kinases. For example, by inhibiting p56 lck, the compounds block downstream signaling events following T cell activation by antigen. Activation of antigen-specific T cells is necessary for the induction and progression of diseases, including autoimmune diseases, allergic diseases and transplant rejection (J. H. Hanke et al., *Inflamm. Res.*, 1995, 44, 357). Therefore the compounds of the invention are useful for treating such diseases. These include but are not limited to rheumatoid arthritis, multiple sclerosis, Guillain-Barre syndrome, Crohn's disease, ulcerative colitis, psoriasis, graft versus host disease, systemic lupus erythematosus, insulin-dependent diabetes mellitus and asthma.

In view of their inhibitory effect on src-family kinases and PDGFR kinase, the compound of the invention are useful in treating cancer. For example, the compounds of the invention are useful in treating src-dependent tumors, such as in mammary carcinoma, colon carcinoma, melanoma and sarcoma, and are also useful in treating PDGF-dependent tumors, such as ovarian cancer, prostate cancer and glioblastoma. In view of their inhibitory effect on src kinase, the compounds of the invention are also useful in treating conditions involving cerebral ischemia, for example, in reducing brain damage following a stroke.

By inhibiting p60src, compounds of the invention may also be useful in treating osteoporosis, Paget's disease, bone inflammation and joint inflammation. By inhibiting PDGFR kinase, compounds of the invention may also be useful in treating fibrotic diseases, restenosis and atherosclerosis. By inhibiting lyn kinase, the compounds of the invention may also be useful in enhancing or potentiating the effectiveness of radiation therapy.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, rectally, topically or by inhalation. The preferred modes of administration are oral and intravenous. Compositions comprising the compounds of the invention for each of the aforementioned routes of administration will be apparent to the skilled artisan. For example, one embodiment of the invention provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition.

Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of formula(I) may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

SYNTHETIC EXAMPLES

Example 1

Synthesis of 2-(2,6-Dichlorophenylamino)-1H-imidazo[4,5-f]quinazoline-7,9(6H,8H)-dione

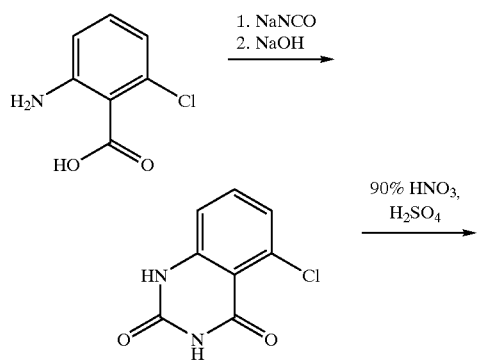

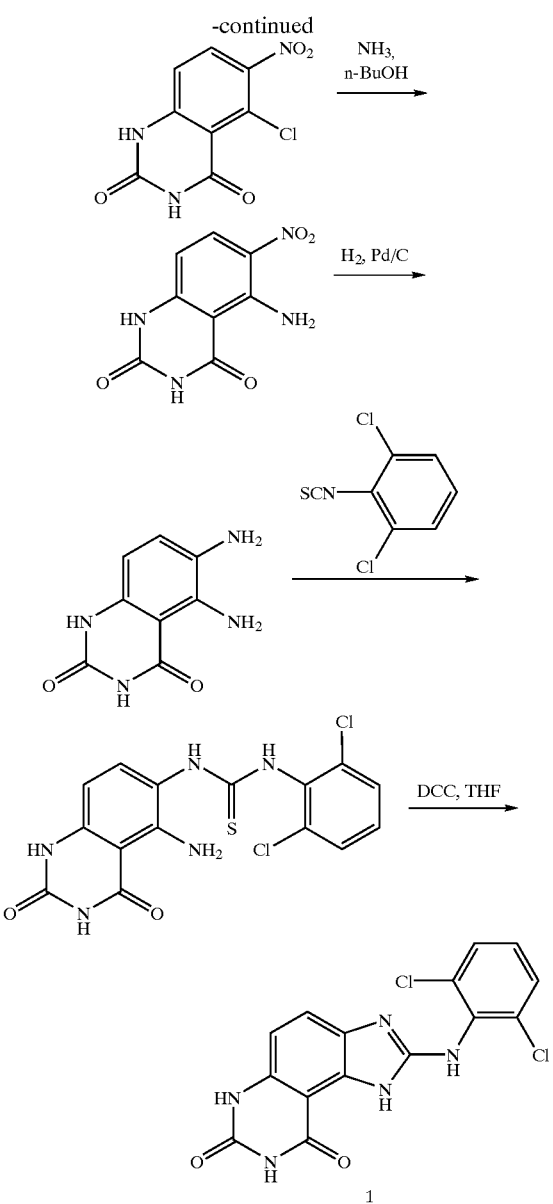

To a solution of 6-chloroanthranilic acid (1.72 g, 10 mmol) and NaOH (0.40 g, 10 mmol) in water (15 mL) was added sodium cyanate (0.72 g, 11 mmol), followed by acetic acid (0.66 g, 11 mmol). The solution was stirred for 9 h, and then acidified with conc. HCl. The precipitate was filtered off and washed with water. The wet solid was added to a solution of NaOH (8.0 g, 200 mmol) in water (60 mL) and stirred for 20 h. The precipitate was filtered off and suspended in water (80 mL), then heated to boiling and acidified with 50% $H_2SO_4$. The cooled mixture was filtered, the solid washed well with water and dried to give 5-chloroquinazolin-2,4-dione (1.42 g, 72%).

A solution of the above quinazolinedione (0.98 g, 5.0 mmol) in conc. $H_2SO_4$ (5 mL) was cooled to −10° C., and 90% $HNO_3$ (0.35 g, 5.0 mmol) was added with stirring. Stirring continued for 1 h at −10° C., and 1.5 h at room temperature. The mixture was poured onto ice, filtered, washed with water and dried to give 5-chloro-6-nitroquinazolin-2,4-dione, along with some of the 8-nitro isomer (1.3 g, 94%).

Butanol (10 mL) was saturated with ammonia and placed in a sealed tube with the above compound (1.0 g, 4.1 mmol). The tube was heated to 125° C. for 3 h, then cooled. The solid was collected, washed with water, then ether, and dried to give 5-amino-6-nitroquinazolin-2,4-dione (0.82 g, 89%).

A suspension of the above amine (450 mg, 2.0 mmol) in DMF (15 mL) was hydrogenated over 10% Pd/C (60 mg) at 50 psi for 20 h. The catalyst was removed by filtration and the solvent removed to give 5,6-diaminoquinazolin-2,4-dione (369 mg, 95%) as a dark solid.

A mixture of the above diamine (342 mg, 1.78 mmol) and 2,6-dichlorophenylisothiocyanate (400 mg, 1.96 mmol) in DMF was stirred for 17 h. The solvent was removed and the residue triturated with EtOAc to give the thiourea. A portion of the thiourea (200 mg, 0.51 mmol) was dissolved in DMF (2 mL) and a solution of dicyclohexylcarbodiimide (125 mg, 0.61 mmol) in THF (4 mL) was added. The mixture was heated to 80° C. under reflux for 7 h, and the solvent removed. The residue was dissolved in CH$_2$Cl$_2$/THF/TFA (150:50:1) and filtered though a plug of silica. The filtrate was evaporated, the residue triturated twice with THF, and the supernatant pipetted off. The solid was suspended in MeOH, neutralized with NH$_4$OH, and the product collected by centrifugation to give the title compound, 1 (89 mg). Mp>300° C.

Example 2

Synthesis of 2-(2,6-Dichlorophenylamino)-6-methyl-1H-imidazo[4,5-f]quinazoline-7,9(6H,8H)-dione

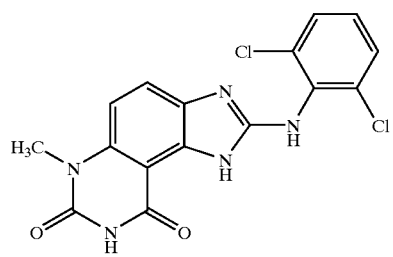

2

Sodium (3.35 g, 146 mmol) was slowly added to stirred MeOH (45 mL). Upon completion of gas evolution, 6-chloroanthranilic acid (5 g, 29 mmol) was added forming a suspension. This mixture was added to a separate flask containing a suspension of paraformaldehyde (1.22 g, 43.5 mmol) in MeOH (35 mL), and the resulting solution was stirred for 5 h at room temperature. Sodium borohydride (1.1 g, 29 mmol) was added and the mixture refluxed for 3 h. The cooled mixture was hydrolyzed with 1M potassium hydroxide then neutralized to pH 3 using 2 M HCl. The precipitate was filtered to yield 2-chloro-6-methylamdino benzoic acid (2.2 g, 41%).

2-Chloro-6-methylamino benzoic acid was converted to 5-amino-1-methyl-6-nitroquinazolin-2,4-dione by the three step procedure described in Example 1.

A suspension of 5-amino-1-methyl-6-nitroquinazolin-2,4-dione (400 mg, 1.64 mmol) in MeOH (70 mL) was hydrogenated over 10% Pd/C (150 mg) in a Parr shaker at 50 psi until uptake ceased. The catalyst was removed by filtration and the filtrate concentrated to yield 5,6-diamino-1-methylquinazolin-2,4-dione (350 mg, 99% crude).

A solution of the above diamine (350 mg, 1.69 mmol) and 2,6-dichlorophenylisothiocyanate (3.81 mg, 1.88 mmol) in DMF (15 mL) was stirred under nitrogen for 72 hr. The solvent was evaporated and the residue triturated with ethyl acetate to yield the thiourea (430 mg, 62%). A portion of the thiourea (300 mg, 0.73 mmol) was dissolved in DMF (3 mL) and a solution of dicyclohexylcarbodiimide (166 mg, 0.73 mmol) in THF (6 mL) was added. The mixture was stirred at 80° C. for 4 h. The solvent was removed, and the residue crystallized twice from MeOH to yield the title compound, 2 (65 mg, 24%). Mp>300° C.

Example 3

Synthesis of 2-(2,6-Dichlorophenylamino)-1,8-dihydro-9H-imidazo[4,5-f]quinazoline-9-one

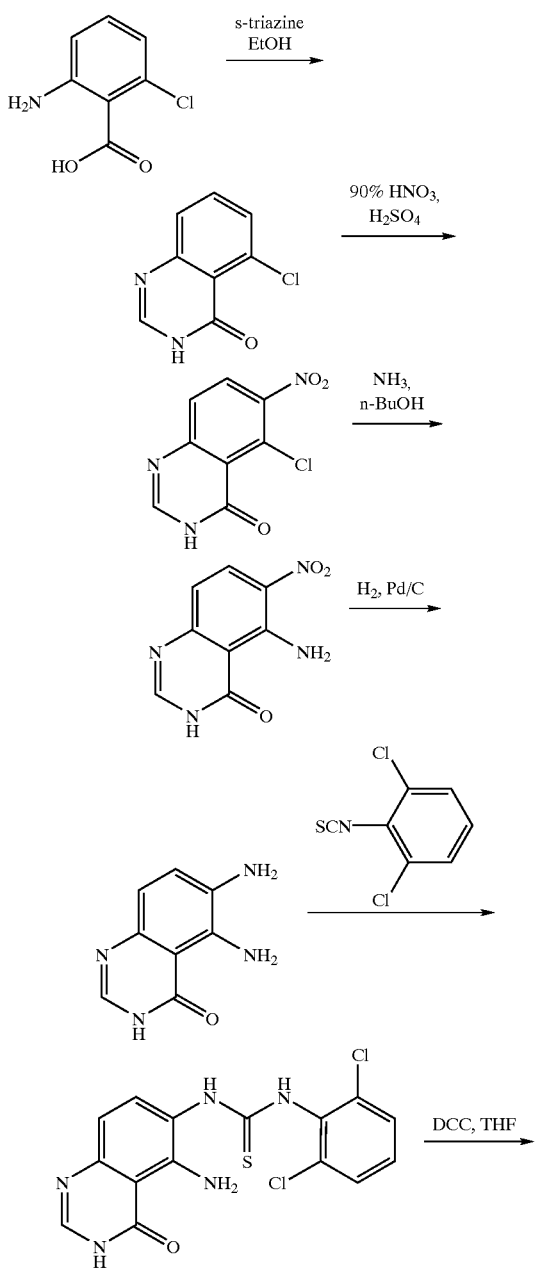

45

-continued

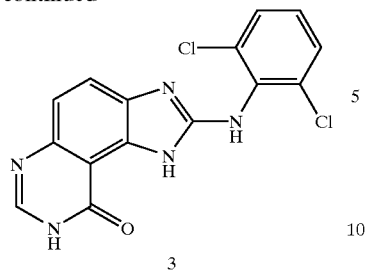

3

A solution of 6-chloro anthranilic acid (2.12 g, 12.3 mmol) and triazine (1.0 g, 12.3 mmol) in EtOH (40 mL) containing piperidine (3 drops) was heated under reflux with stirring for 8 h. On cooling crystals formed, which were filtered to yield 5-chloroquinazolin-4-one (1.55 g, 70%).

A solution of the above quinazolinone (1.26 g, 7.0 mmol) in conc. $H_2SO_4$ (7 mL) was cooled to −20° C., and 90% $HNO_3$ (0.49 g, 7.0 mmol) was added with stirring. Stirring continued for 1 h at −20° C., and 2 h at room temperature. The mixture was poured onto ice, filtered, washed with water and dried to give 5-chloro-6-nitroquinazolin-4-one, along with the 8-nitro isomer in a 4:1 ratio. Three recrystallizations from EtOH gave the product as a 6:1 ratio of isomers (0.85 g).

Butanol (20 mL) was saturated with ammonia and placed in a sealed tube with the above compound (800 mg, 3.6 mmol). The tube was heated to 125° C. for 14 h, then cooled. The solid was collected, washed with EtOH and water, and dried to give 5-amino-6-nitroquinazolin-4-one (569 mg, 78%).

A suspension of the above amine (250 mg, 1.21 mmol) in MeOH (50 mL) was hydrogenated over 10% Pd/C (50 mg) at 50 psi for 5 h. The catalyst was removed by filtration and the filtrate concentrated to yield 5,6-diaminoquinazolin-4-one (210 mg, 98% crude).

A solution of the above diamine (205 mg, 1.19 mmol) and 2,6-dichlorophenylisothiocyanate (272 mg, 1.3 mmol) in DMF (3 mL) was stirred under nitrogen for 18 h. The solvent was evaporated and the residue triturated with ethyl acetate to yield the thiourea (350 mg, 77%). The thiourea was dissolved in DMF (4 mL) and a solution of dicyclohexylcarbodiimide (228 mg, 1.1 mmol) in THF (8 mL) was added. The mixture was stirred at 80° C. for 8 h and the solvent evaporated. The residue was purified by column chromatography in $CH_2Cl_2$/MeOH 98:2–90:10. Pure fractions were combined, evaporated, and the residue recrystallized from MeOH to give the title compound, 3 (87 mg). mp 230–235° C.

46

Example 4

Synthesis of 2-(2,6-Dichlorophenylamino)-1-methyl-1,8-dihydro-9H-imidazo[4,5-f]quinazoline-9-one

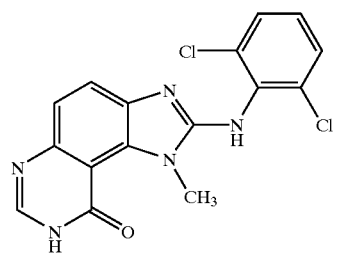

4

5-Chloro-6-nitroquinazolin-4-one, from Example 3 (0.26 g, 1.15 mmol) was suspended in MeOH (3 mL) at −20° C. Methylamine gas was passed into the mixture for a few minutes, resulting in a clear solution. The solution was stirred at room temperature for 5 h and evaporated to give 5-methylamino-6-nitroquinazolin-4-one in quantitative yield. The above amine (350 mg, 1.6 mmol) was hydrogenated over platinum oxide (30 mg) in MeOH (200 mL) at 60 psi for 4 h. The mixture was filtered through diatomaceous earth and the solvent evaporated, to give 6-amino-5-methylaminoquinazolin-4-one, which was immediately suspended in EtOAc (20 mL) and THF (10 mL). A solution of 2,6-dichlorophenylisothiocyanate (340 mg, 1.67 mmol) in EtOAc (5 mL) was added, and the mixture stirred for 16 h. The reaction mixture was concentrated to half the volume, filtered, and the solid washed with EtOAc to yield the thiourea (400 mg, 64% over 2 steps.)

A solution of the above thiourea (295 mg, 0.75 mmol) and dicyclohexylcarbodiimide (160 mg, 0.78 mmol) in THF (12 mL) and DMF (10 mL) was heated to 70° C. with stirring for 48 h. The mixture was poured into ice water (50 mL) and filtered. The filtrate was extracted with EtOAc and evaporated. The residue was combined with the filtered solid, triturated with chloroform, and the supernatant decanted. The solid was dissolved in boiling MeOH (100 mL), filtered hot, concentrated to 60 mL, and water (10 mL) added slowly. The crystals were collected to give the title compound, 4 (110 mg, 41%). Mp>300° C.

Example 5

Synthesis of 2-(2,6-Dichlorophenylamino)-1-ethyl-1,8-dihydro-9H-imidazo [4,5-f]quinazoline-9-one This compound was synthesized in by the method of Example 4. Mp>300 ° C.

Examples 6 and 7

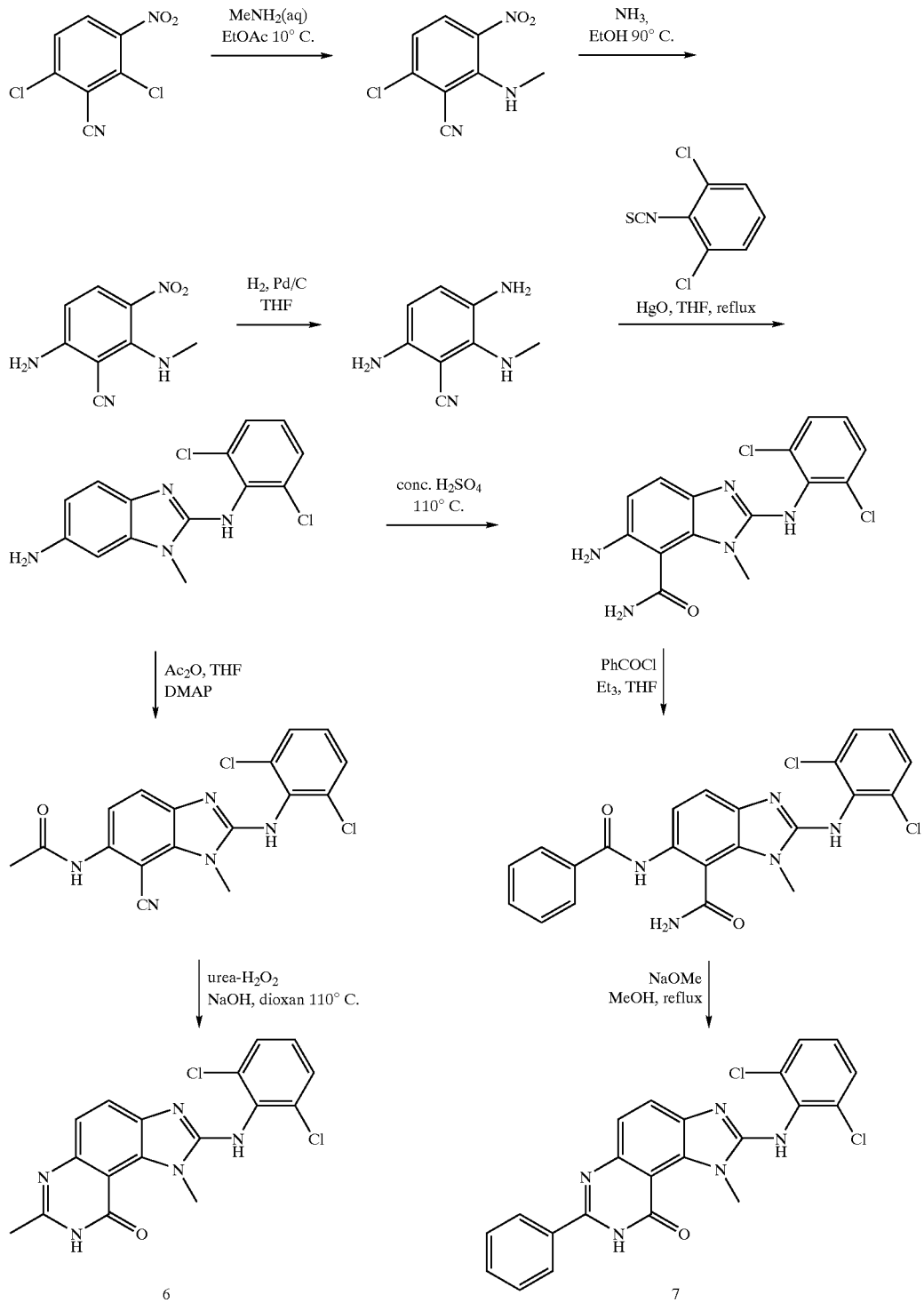

Example 6

Synthesis of 2-(2,6-Dichlorophenylamino)-1,7-dimethyl-1,8-dihydro-9H-imidazo[4,5-f]quinazoline-9-one A solution of 2,6-dichloro-3-nitrobenzonitrile (98.7 g, 0.455 mol) in EtOAc (910 mL) was cooled to 5° C. 40% Aqueous methylamine (79.5 mL, 1.14 mol) was added with vigorous mechanical stirring, keeping the temperature at 10–15° C. After addition was complete, stirring was continued for 3 h at the same temperature. More methylamine (16 mL, 0.23 mol) was added, and the mixture stirred for a further 1.5 h at room temperature. Water (300 mL) was added, followed by hexane (450 mL). The mixture was stirred for 15 min, filtered, and the solid washed with water and MeOH, to give 6-chloro-2-methylamino-3-nitrobenzonitrile (80.3 g, 83%), mp 167–170° C.

A suspension of the above amine (30.0 g, 142 mmol) in a 5.3 M solution of ammonia in ethanol (200 mL) was heated in a sealed stainless steel reaction vessel (600 mL capacity) at 90° C. for 24 h. The reaction vessel was cooled to room temperature, then to 0° C., and opened. The product was filtered, washed with ethanol (30 mL) and dried to give 6-amino-2-methylamino-3-nitro-benzonitrile (25.94 g, 95%) as a yellow solid.

A solution of the above diamine (5.0 g, 26 mmol) in THF (150 mL) was hydrogenated over 10% Pd/C (1.0 g) at 50 psi for 4 h. The reaction mixture was filtered through a pad of diatomaceous earth and rinsed with THF (50 mL). The filtrate was not concentrated but used crude as a THF solution.

To the above triamine solution was added 2,6-dichlorophenylisothiocyanate (5.3 g, 26 mmol) and the solution was stirred at room temperature for 0.5 hr. TLC indicated complete formation of the thiourea intermediate. Mercury (II) oxide (6.2 g, 29 mmol) was then added, and the mixture was heated to reflux for 2 h. TLC showed conversion to the benzimidazole. The reaction mixture was cooled to room temperature, activated carbon (about 1 g) was added, and stirred at 50° C. for 2 h. The mixture was filtered through a pad of diatomaceous earth and rinsed with EtOAc until the filtrate was colorless. The combined filtrates were concentrated to obtain a pink solid, which was triturated with EtOAc/hexane (1:4). The light grey color solid was filtered and dried to give 5-amino-3-methyl-2-(2,6-dichlorophenylamino)-3H-benzimidazole-4-carbonitrile (7.42 g). The mother liquor was concentrated and triturated again to provide a second crop (0.15 g), combined yield 87%, MS (EI+): MH+=331.

To the above amino nitrile (60 mg, 0.18 mmol) in THF (1 mL) was added acetic anhydride (74 mg, 0.72 mmol) and DMAP (1 crystal), and the solution stirred for 22 h. MeOH (0.5 mL) was added, and stirring continued for 1 h. The solution was partitioned between EtOAc and dilute $NH_4OH$, and the residue from the organic layer purified by flash chromatography, eluting with $CH_2Cl_2$/THF 95:5, to give recovered amino nitrile (18 mg) and 5-acetamido-3-methyl-2-(2,6-dichlorophenylamino)-3H-benzimidazole-4-carbonitrile (47 mg).

A suspension of the above acetamide (30 mg, 0.08 mmol) in dioxan (1 mL) and 0.2M NaOH (1 mL) was heated to 110° C. Urea-hydrogen peroxide complex (15 mg, 0.16 mmol) was added with stirring. Further 30 mg portions of urea-hydrogen peroxide were added at 2.5 h, 3.5 h and 21 h. After heating for 25 h, the mixture was cooled and partitioned between THF and water. The residue from the organic layer was purified on a flash column, eluting with $CH_2Cl_2$/MeOH 98:2, to give the title compound, 6 (7 mg, 23%), mp 305–310° C.(dec), MS (ES) 374, 376 (MH+).

Example 7

Synthesis of 2-(2,6-Dichlorophenylamino)-1-methyl-7-phenyl-1,8-dihydro-9H-imidazo[4,5-f]quinazoline-9-one A mixture of 5-amino-3-methyl-2-(2,6-dichlorophenylamino)-3H-benzimidazole-4-carbonitrile (Example 6) (1 g, 3 mmol) and conc. $H_2SO_4$ (8 mL) was warmed to 100–110° C. for 1 h and monitored by TLC for the disappearance of starting material. The mixture was cooled and poured onto a mixture of crushed ice, sodium carbonate, and ether. The precipitate was filtered, washed with water, dissolved in MeOH-methylene chloride, treated with carbon (decolorizing charcoal), dried ($MgSO_4$), filtered, and concentrated in vacuo. The aqueous filtrate was washed with EtOAc (3×30 mL). The combined organic layers were washed with brine (25 mL), which was then extracted with EtOAc (20 mL). The combined organic layers were dried ($MgSO_4$), filtered, and concentrated to yield 190 mg of a crude product. This was combined with the solid product and triturated with ether-methylene chloride to afford 5-amino-2-(2,6-dichlorophenylamino)-3-methyl-3H-benzoimidazole-4-carboxylic acid amide (700 mg, 66%). The filtrate was chromatographed on silica gel to afford an additional 128 mg (12%) of product.

The above amino amide (50 mg, 0.15 mmol) was added to a solution of benzoyl chloride (32 mg, 0.23 mmol) in THF (1 mL). Triethylamine (0.03 mL, 0.23 mmol) was added and the mixture stirred for 1 h. TLC showed conversion to the benzamide. The solvent was evaporated and the residue dissolved in MeOH (1 mL). Sodium methoxide in MeOH (25%, 0.2 mL) was added and the solution heated to reflux for 45 min. The cooled mixture was partitioned between 1M $NH_4Cl$ and $CH_2Cl_2$. The residue from the organic layer was stirred and refluxed with MeOH (2 mL) for 1 h, cooled, filtered and washed with MeOH to yield the title compound, 7 (52 mg, 79%) Mp>300° C. MS (ES+) 436,438 (MH+).

Example 8

Synthesis of 2-(2,6-Dichlorophenylamino)-1-methyl-7-furan-3-yl-1,8-dihydro-9H-imidazo[4,5-f]quinazoline-9-one

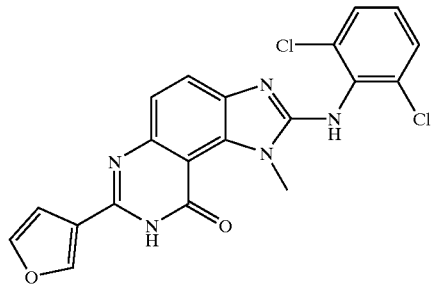

8

Furan-3-carboxylic acid (20 mg, 0.18 mmol), hydroxy-benzotriazole (24 mg, 0.18 mmol) and 1-[3-(dimethylamino)propyl]-3-ethylcarbodiimide hydrochloride (35 mg, 0.18 mmol) were stirred together in DMF (1 mL) for 15 min. 5-Amino-2-(2,6-dichlorophenylamino)-3-methyl-3H-benzoimidazole-4-carboxylic acid amide (Example 7)(50 mg, 0.15 mmol) was added, and stirring continued for 24 h. The solution was diluted with EtOAc and washed in turn with aqueous $Na_2CO_3$, water and brine. The organic layer was evaporated and the residue dissolved in MeOH (2 mL). Sodium methoxide in MeOH (25%, 0.1 mL) was added and the solution heated to reflux for 45 min. The cooled solution was partitioned between water and $CH_2Cl_2$. The organic layer was evaporated and the crude product stirred with MeOH (1 mL) for 1 h. The solid was filtered, washed with a few drops of MeOH and dried to yield the title compound, 8 (14 mg, 22%). mp>300° C. MS (ES) 428, 426 (MH+).

Example 9

Synthesis of 7-Allylamino-2-(2,6-dichlorophenylamino)-1-methyl-1,8-dihydro-9H-imidazo[4,5-f]quinazoline-9-one

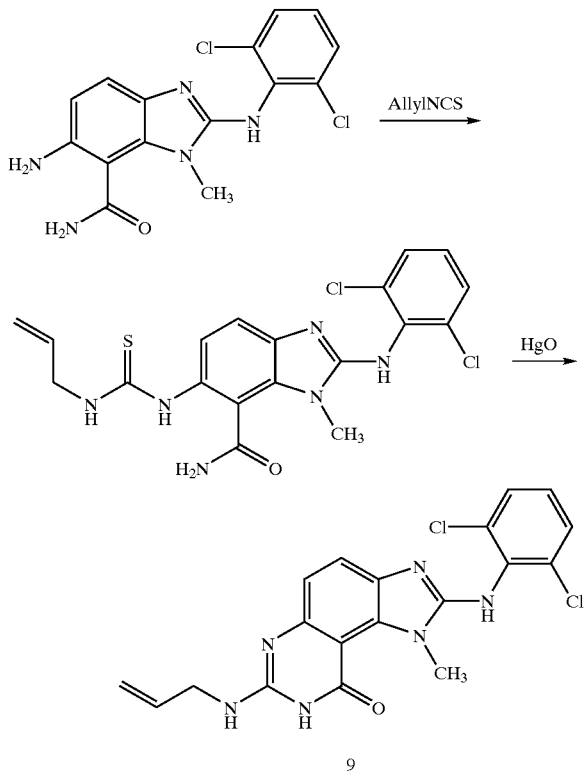

A mixture of 100 mg (0.286 mmol) of 5-amino-2-(2,6-dichlorophenylamino)-3-methyl-3H-benzimidazole-4-carboxylic acid amide (Example 7) and 114 mg (1.15 mmol) of allyl isothiocyanate in DMF was warmed at 45° C. for 48 h. The reaction was diluted with 30 mL of brine and extracted with four 15 mL portions of EtOAc. The combined organic layers were washed with five 15 mL portions of brine, dried (MgSO$_4$), filtered and concentrated in vacuo. The residue was adsorbed onto silica gel and chromatographed on silica gel (MeOH-methylene chloride, first 2:98, then 4:96, then 5:95) to afford 66 mg (51%) of 2-(2,6-dichlorophenylamino)-3-methyl-5-(3-allyl-thioureido)-3H-benzimidazole-4-carboxylic acid amide.

A mixture of 66 mg (0.15 mmol) of the above amide and 300 mg (1.38 mmol) of mercury (II) oxide in THF was warmed at reflux for 18 h. The reaction was cooled to room temperature and filtered through diatomaceous earth. The filtrate was adsorbed onto silica gel and chromatographed over silica gel (methylene chloride, then MeOH-methylene chloride, first 1:99, then 2:98, then 3:97) to afford an off white solid which was triturated with methylene chloride-MeOH to afford 17 mg (27%) of the title compound 9, mp 255–260° C.

Example 10

Synthesis of N-[2-(2,6-Dichlorophenylamino)-1-methyl-9-oxo-1,8,-dihydro-9H-imidazo[4,5-f]quinazolin-7-yl]-benzamide

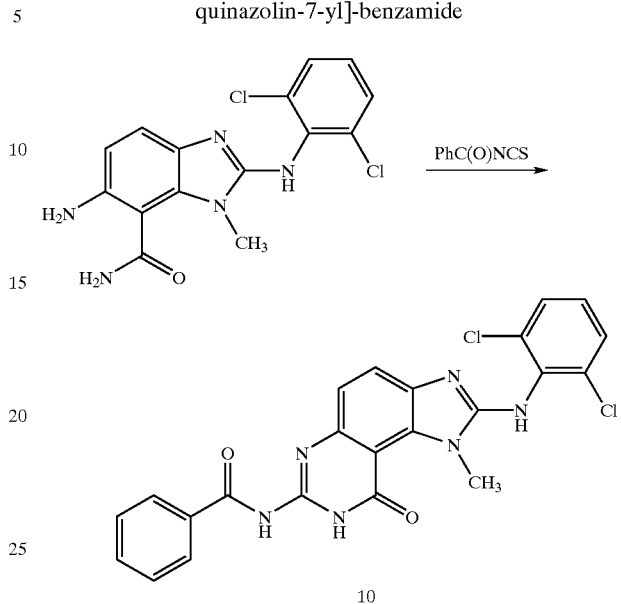

To a solution of 128 mg (0.36 mmol) of 5-amino-2-(2,6-dichlorophenylamino)-3-methyl-3H-benzimidazole-4-carboxylic acid amide (Example 7) in 10 mL of THF was added 72 mg (0.45 mmol) of benzoyl isothiocyanate. The reaction was warmed at reflux and after 5 min, thin-layer chromatography indicated a new product. 95 mg (0.44 mmol) of mercury (II) oxide was added and refluxing continued for 24 h. The reaction was cooled and filtered through diatomaceous earth washing the filter cake with EtOAc. The crude residue was adsorbed onto silica gel and chromatographed over silica gel (MeOH-methylene chloride, first 1:99, then 2:98, then 3:97). The material from the column was triturated with ether-dichloromethane to afford 64 mg (36%) of the title compound 10, mp, 185–190° C.

Example 11

Synthesis of 7-Amino-2-(2,6-dichlorophenylamino)-1-methyl-1,8-dihydro-9H-imidazo[4,5-f]quinazolin-9-one

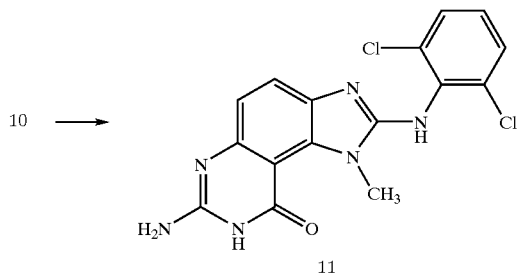

A mixture of 130 mg (0.27 mmol) 10 and 500 mg (3.62 mmol) of potassium carbonate in MeOH was stirred for 18 h. The mixture was then diluted with brine and extracted with EtOAc to afford 12 mg of product. Additional material was obtained as an insoluble solid from the extraction layers. The combined materials were dissolved in 1N aqueous HCl, diluted with THF, made basic with solid/saturated aqueous sodium bicarbonate and extracted with EtOAc to afford 40 mg (40%) of product. Trituration with ether gave 30 mg (30%) of title compound 11, mp>305° C.

Example 12

Synthesis of 2-(2,6-Dichlorophenylamino)-1-methyl-7-(1-methyl-2-phenyl-vinyl)-1,6,7,8-tetrahydro-9H-imidazo[4,5-f]quinazolin-9-one

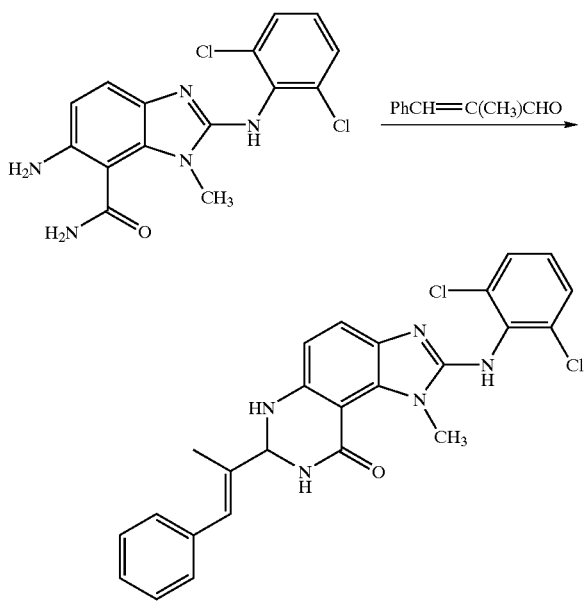

A mixture of 110 mg (0.315 mmol) of 5-amino-2-(2,6-dichlorophenylamino)-3-methyl-3H-benzimidazole-4-carboxylic acid amide, 184 mg (1.26 mmol) of α-methyl-trans-cinnamaldehyde and 60 mg (0.31 mmol) of p-toluenesulfonic acid in 10 mL of THF were stirred at RT for 18 h. The reaction was made basic with saturated aqueous sodium bicarbonate and extracted with EtOAc. The combined organic layers were washed with saturated aqueous sodium bicarbonate, brine, dried (MgSO₄), filtered and evaporated in vacuo. The crude residue was chromatographed on silica gel to afford 102 mg (68%) of title compound 12.

Example 13

Synthesis of 2-(2,6-Dichlorophenylamino)-1-methyl-7-(1-methyl-2-phenyl-vinyl)-1,8-dihydro-9H-imidazo[4,5-f]quinazoline-9-one

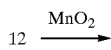

-continued

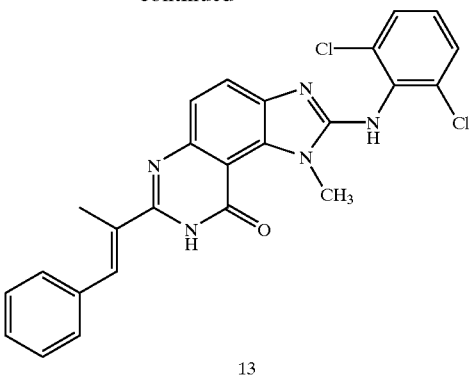

A mixture of 102 mg (0.213 mmol) 12 and 300 mg (3.45 mmol) of manganese dioxide was stirred in 15 mL of THF for 45 min. The reaction was filtered through diatomaceous earth and evaporated in vacuo. The crude residue was evaporated onto silica gel and chromatographed over silica gel (methylene chloride, then MeOH-methylene chloride first 1:99 then 2:98). The material from the column was triturated with MeOH-methylene chloride to afford 70 mg (69%) of title compound 13, mp>305° C.

Example 14

Synthesis of 2-(2,6-Dichlorophenylamino)-1-methyl-1H-imidazo[4,5-f]quinazoline-7,9(6H,8H)-dione

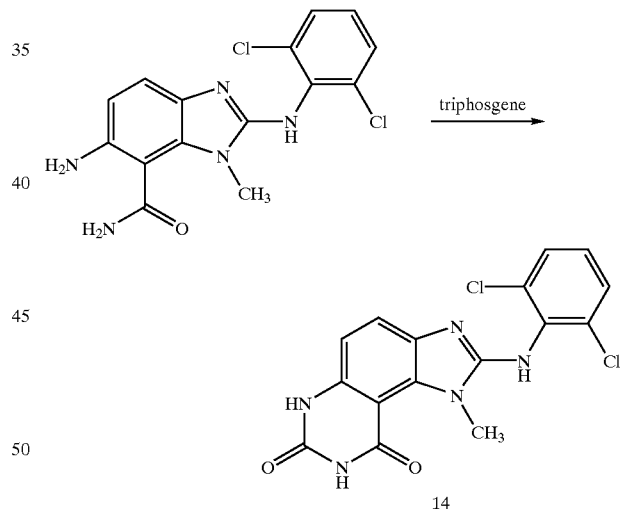

To a solution of 80 mg (0.229 mmol) of 5-amino-2-(2,6-dichlorophenylamino)-3-methyl-3H-benzimidazole-4-carboxylic acid amide (Example 7) in 8 mL THF cooled to 0° C. was added 67 mg (0.23 mmol) of triphosgene. After stirring 30 min, the reaction was diluted with saturated aqueous sodium bicarbonate and water, and the THF was evaporated in vacuo. The resulting suspension was filtered and the solid dried by pulling vacuum through the filter cake. The crude product was absorbed onto silica gel and chromatographed over silica gel (MeOH-methylene chloride first 1:99 then 2:98 then 3:97 then 4:96) to afford a solid which was triturated with methylene chloride to afford 20 mg (23%) of the title compound 14, mp>300° C.

Example 15

Synthesis of 2-(2,6-Dichlorophenylamino)-1,7-dimethyl-1,6,7,8-tetrahydro-9H-imidazo[4,5-f]quinazolin-9-one

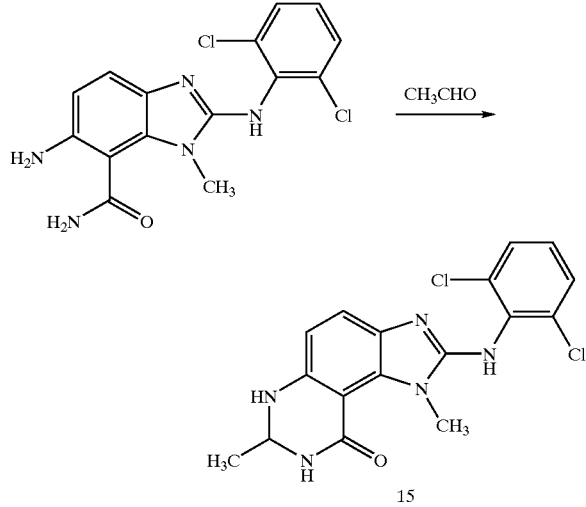

15

A mixture of 30 mg (0.086 mmol) of of 5-amino-2-(2,6-dichlorophenylamino)-3-methyl-3H-benzimidazole-4-carboxylic acid amide (Example 7) and 1 mL (18 mmol) of acetaldehyde was stirred under an argon atmosphere while chilled in an ice-water bath for 0.5 h, then warmed to room temperature. p-Toluenesulfonic acid was added, (catalytic) and after stirring for 1 h, 2 mL of MeOH was added. After 2 h the reaction was poured into a mixture of saturated aqueous sodium bicarbonate and EtOAc. The aqueous layer was extracted with EtOAc, the combined organic layers were extracted with saturated aqueous sodium bicarbonate, brine, dried (MgSO₄), treated with activated carbon, filtered, and concentrated in vacuo. The residue was chromatographed over silica gel, followed by elution on a TLC plate to yield 11 mg (34%) of title compound 15, mp 200–203° C.

Example 16

Synthesis of 2-(2,6-Dichlorophenylamino)-1,7,7-trimethyl-1,6,7,8-tetrahydro-9H-imidazo[4,5-f]quinazolin-9-one

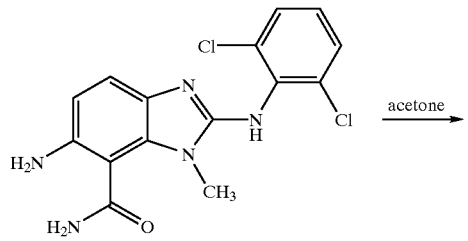

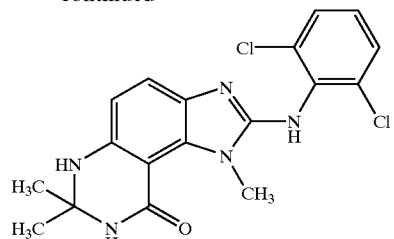

16

A mixture of 38 mg (0.11 mmol) of 5-amino-2-(2,6-dichlorophenylamino)-3-methyl-3H-benzimidazole-4-carboxylic acid amide (Example 7), 3 mg (0.02 mmol) p-toluenesulfonic acid, and 2 mL (27 mmol) of acetone was stirred at room temperature for 1 h, then heated to reflux for 1.5 h. The reaction was cooled and poured into a mixture of saturated aqueous sodium bicarbonate and EtOAc. The aqueous phase was extracted with EtOAc, the combined organics were extracted with saturated aqueous sodium bicarbonate, brine, dried (MgSO₄), treated with activated carbon, filtered, and concentrated in vacuo to afford 26 mg of an orange solid. The crude product was chromatographed over silica gel to afford 20 mg (47%) of title compound 17, mp 238–239° C.

Example 17

Synthesis of 2-(2,6-Dichlorophenylamino)-1,7-dimethyl-9-oxo-6,7,8,9-tetrahydro-1H-imidazo[4,5f]quinazoline-7-carboxylic Acid Ethyl Ester

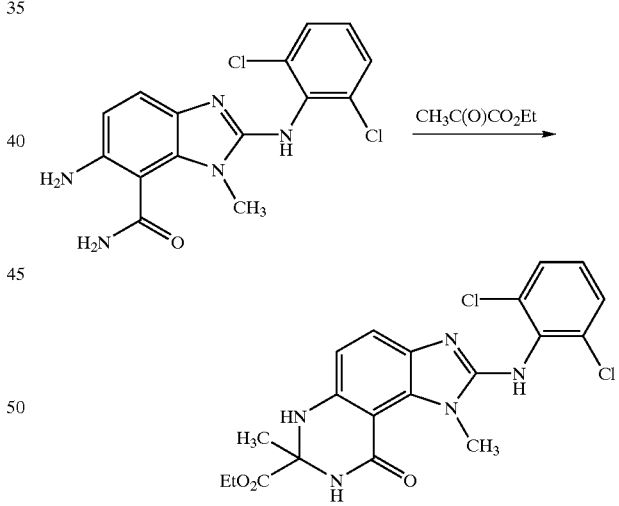

17

A mixture of 100 mg (0.29 mmol) of 5-amino-2-(2,6-dichlorophenylamino)-3-methyl-3H-benzimidazole-4-carboxylic acid amide (Example 7), 332 mg (2.9 mmol) of ethyl pyruvate, and a catalytic amount of p-toluenesulfonic acid in 2 mL of dichloromethane was heated in a sealed tube to 85° C. for 2 h, then 0.5 mL EtOH was added, and heating continued for 15 min. The reaction was cooled and stirred at room temperature for 1 h. The reaction was concentrated in vacuo, and the residue was suspended in dilute aqueous sodium hydroxide, filtered, washed with water and dried by pulling vacuum through the filter cake. The crude product was purified on a TLC plate, and recrystallized from EtOAc to afford 17.6 mg (13.5%) of title compound 17, mp 245–247° C.

ADDITIONAL EXAMPLES

The following additional compounds (Ex. Nos. 18 to 104) in the following Table were prepared by methods analogous to those described above.

| Ex. No. | Structure | M.P. (° C.) |
| --- | --- | --- |
| 18 | 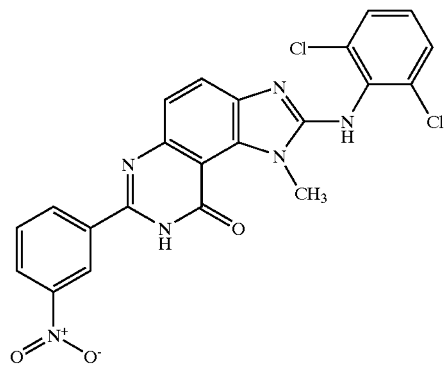 | >300 |
| 19 | 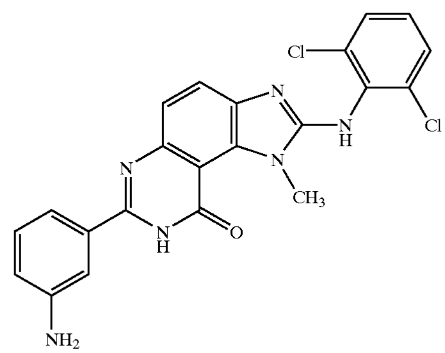 | 200 (dec) |
| 20 | 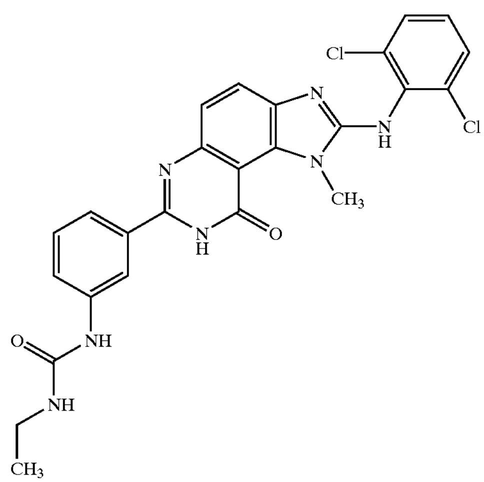 | 251 (dec) |
| 21 | 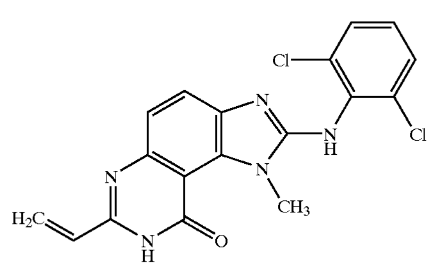 | 278–284 (dec) |

| Ex. No. | Structure | M.P. (° C.) |
| --- | --- | --- |
| 22 | 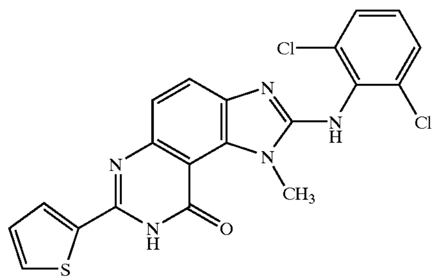 | >300 |
| 23 | 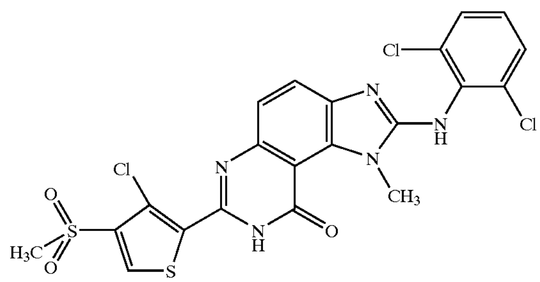 | 280 |
| 24 | 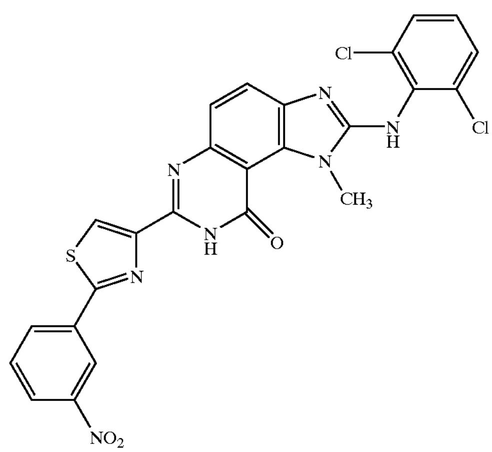 | >300 |
| 25 | 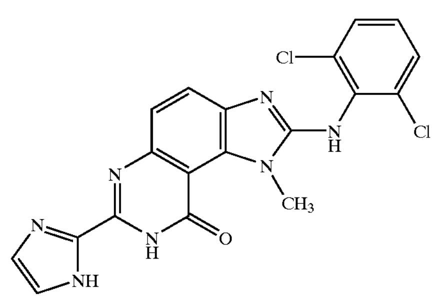 | >300 |

-continued

| Ex. No. | Structure | M.P. (° C.) |
|---|---|---|
| 26 | 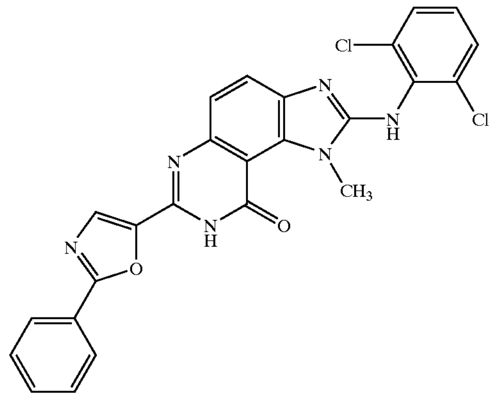 | >290 |
| 27 | 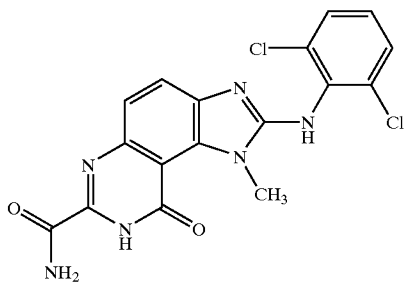 | >300 |
| 28 | 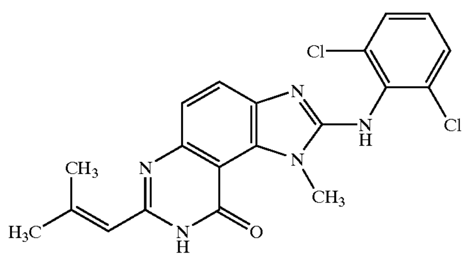 | >300 |
| 29 | 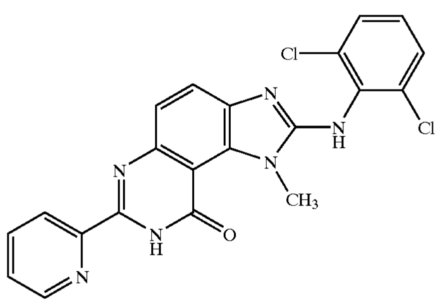 | >300 |
| 30 | 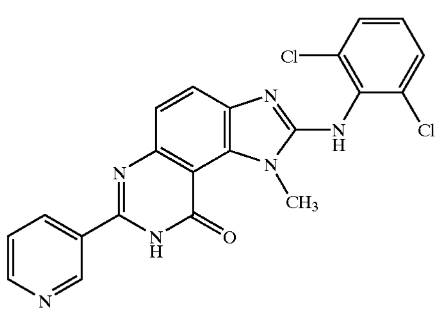 | >300 |

-continued

| Ex. No. | Structure | M.P. (° C.) |
| --- | --- | --- |
| 31 | 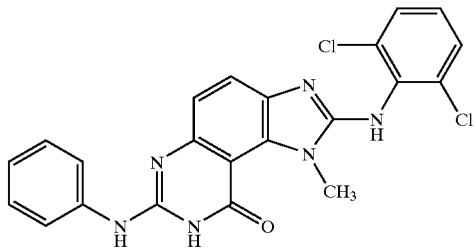 | 185–192 |
| 32 | 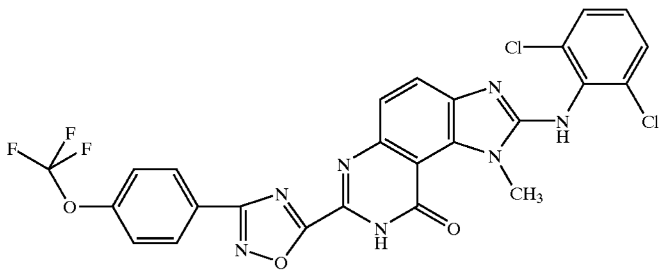 | >300 |
| 33 | 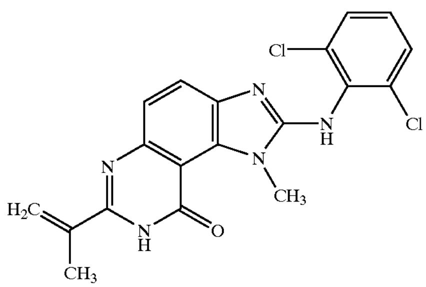 | >300 |
| 34 | 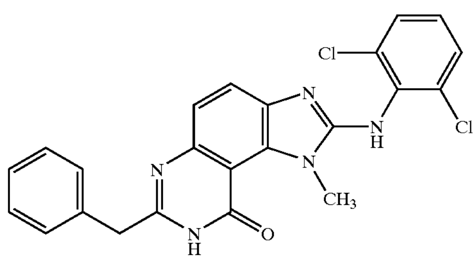 | >250 (dec) |
| 35 | 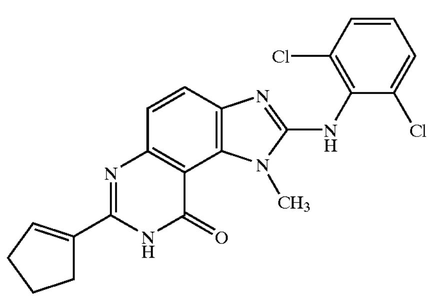 | 295 (dec) |

-continued

| Ex. No. | Structure | M.P. (° C.) |
| --- | --- | --- |
| 36 | 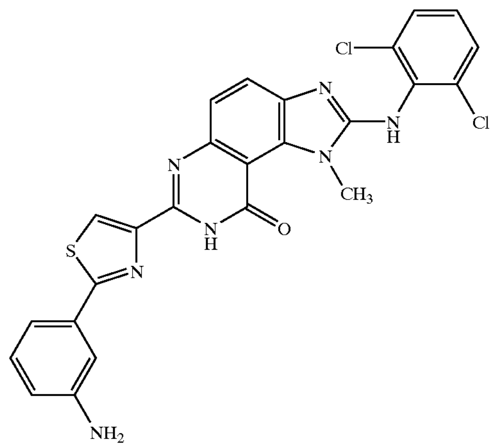 | 240 (dec) |
| 37 | 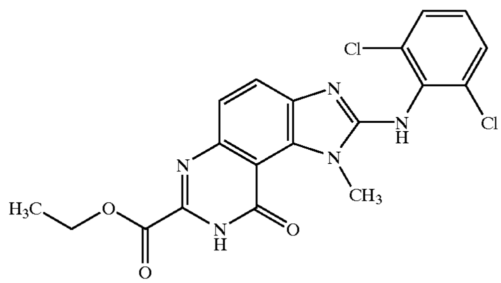 | 275–277 |
| 38 | 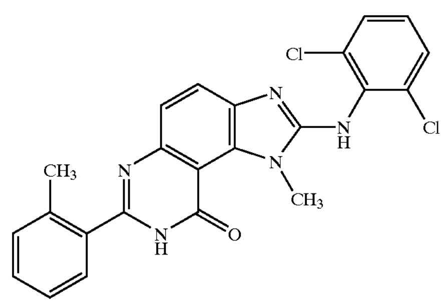 | >300 |
| 39 | 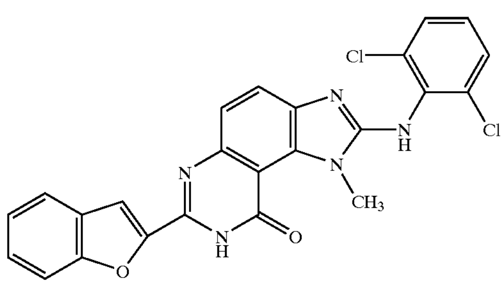 | >300 |
| 40 | 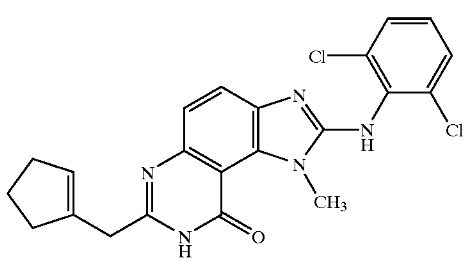 | 258 (dec) |

-continued

| Ex. No. | Structure | M.P. (° C.) |
| --- | --- | --- |
| 41 | 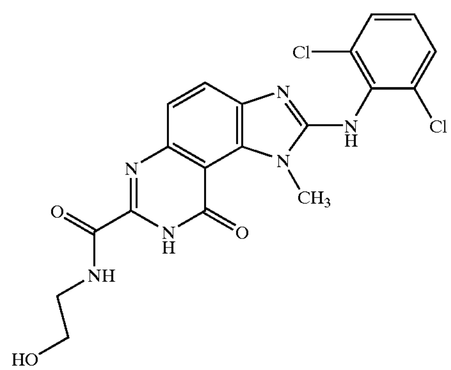 | 265–268 |
| 42 | 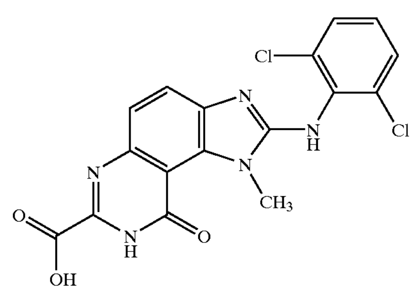 | >300 |
| 43 | 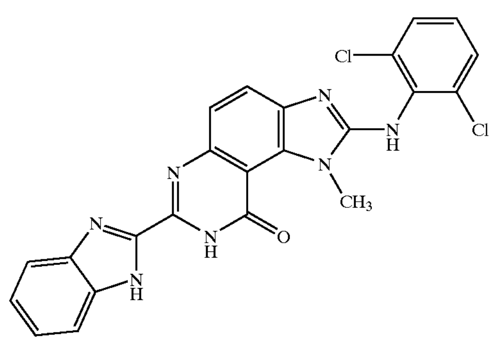 | >300 |
| 44 | 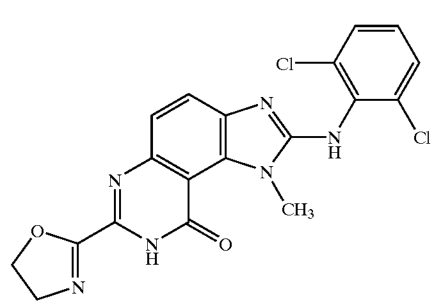 | |

| Ex. No. | Structure | M.P. (° C.) |
|---|---|---|
| 45 | 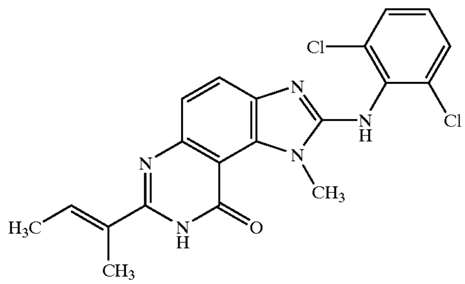 | 278 (dec) |
| 46 | 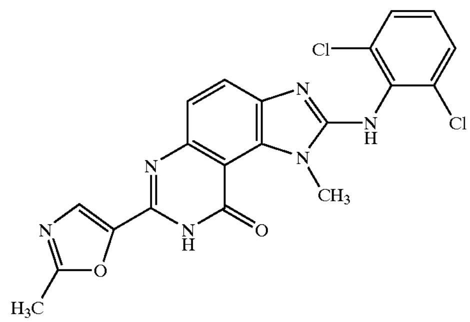 | >300 |
| 47 | 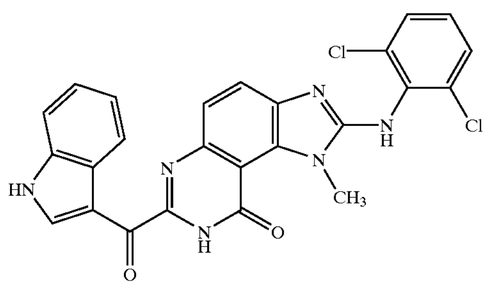 | >300 |
| 48 | 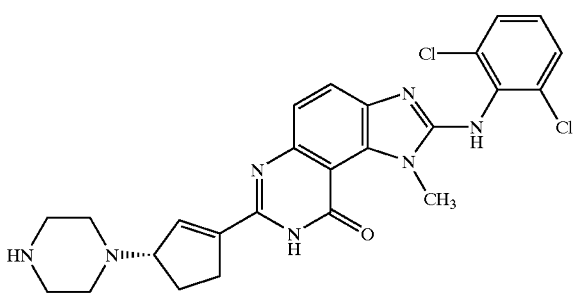 | 173–174 |
| 49 | 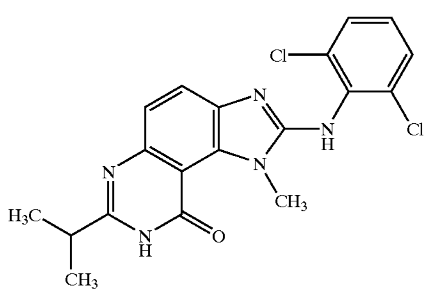 | 279 (dec) |

-continued

| Ex. No. | Structure | M.P. (° C.) |
|---|---|---|
| 50 | 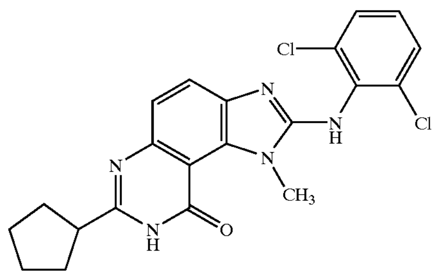 | 283–284 |
| 51 | 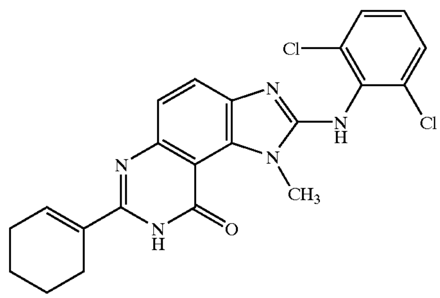 | |
| 52 | 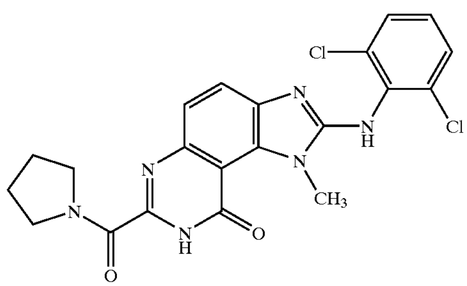 | 295 (dec) |
| 53 | 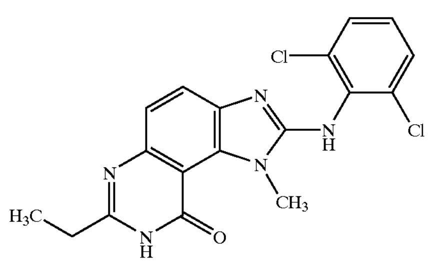 | >300 |
| 54 | 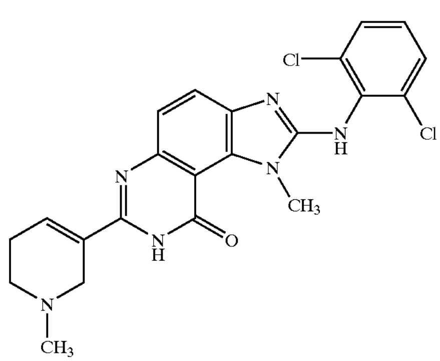 | 255 |

-continued

| Ex. No. | Structure | M.P. (° C.) |
| --- | --- | --- |
| 55 | 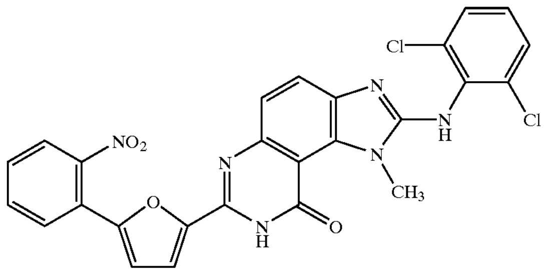 | 289–292 |
| 56 | 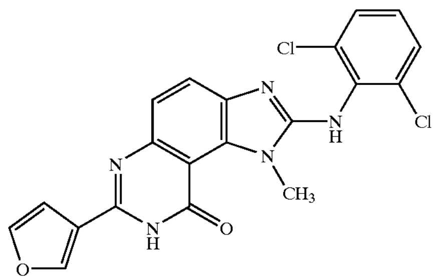 | >300 |
| 57 | 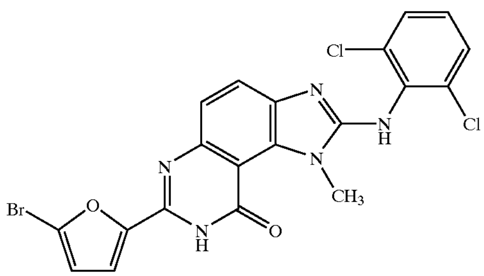 | 280–283 |
| 58 | 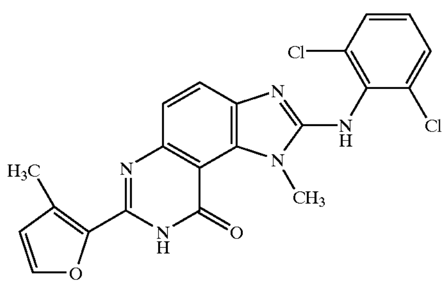 | 304–310 (dec) |
| 59 | 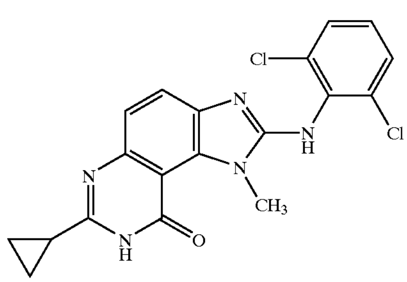 | >300 |

-continued

| Ex. No. | Structure | M.P. (° C.) |
| --- | --- | --- |
| 60 | 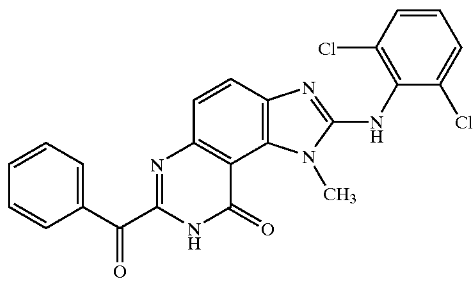 | 280 (dec) |
| 61 | 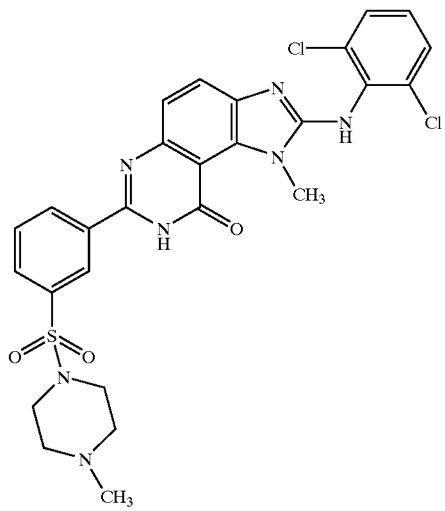 | 215 (dec) |
| 62 | 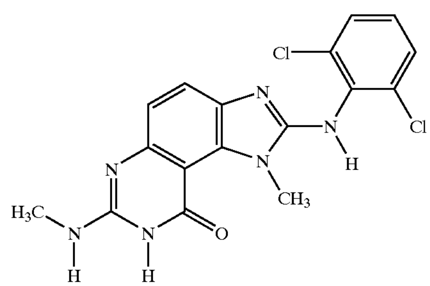 | 198–204 |
| 63 | 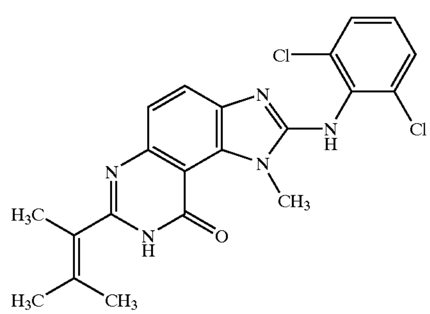 | >300 |

-continued

| Ex. No. | Structure | M.P. (° C.) |
|---|---|---|
| 64 | 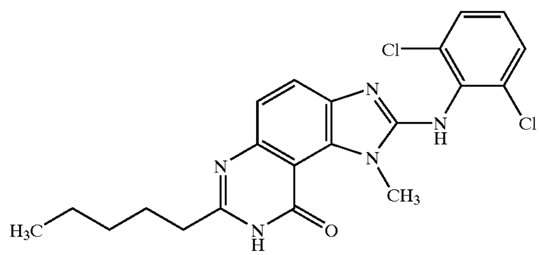 | 257–260 |
| 65 | 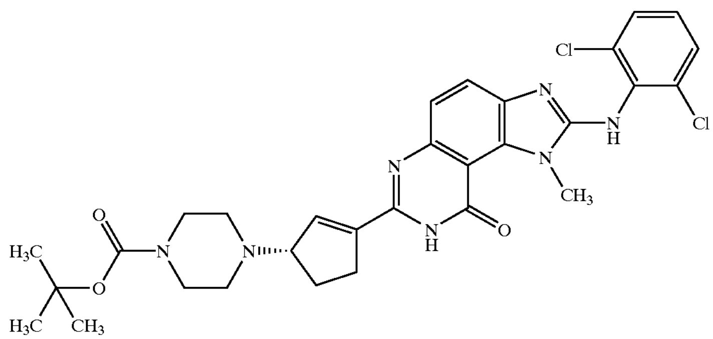 | 168–170 |
| 66 | 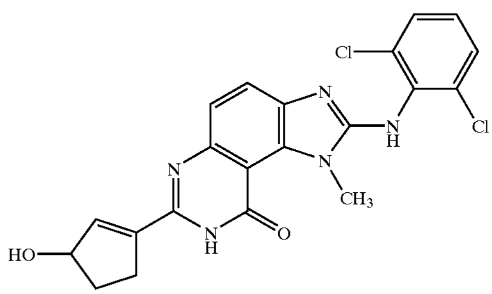 | 285 |
| 67 | 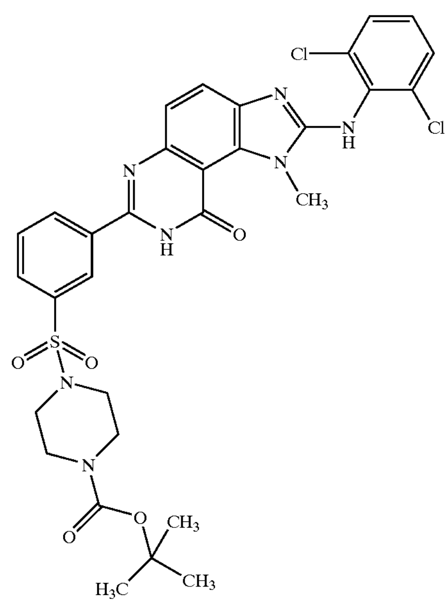 | 189 |

-continued

| Ex. No. | Structure | M.P. (° C.) |
|---|---|---|
| 68 | 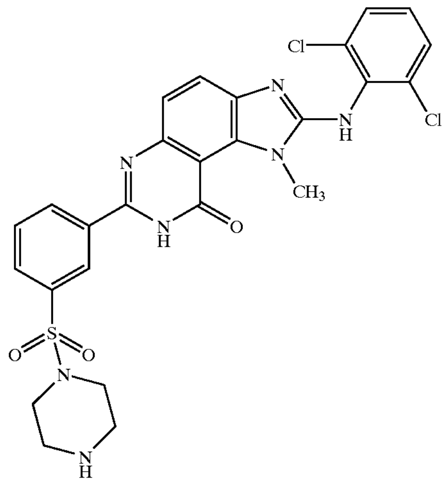 | 210 |
| 69 | 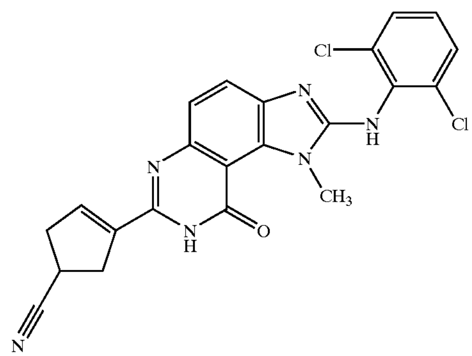 | >295 (dec) |
| 70 | 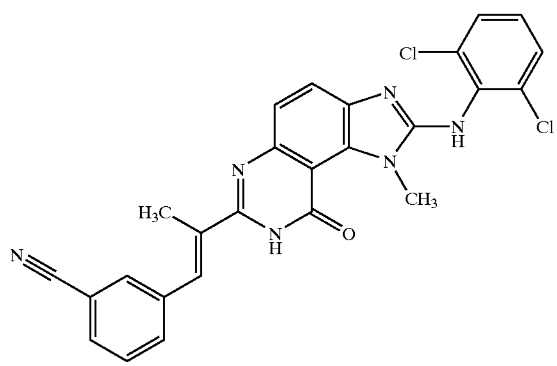 | 288–290 |
| 71 | 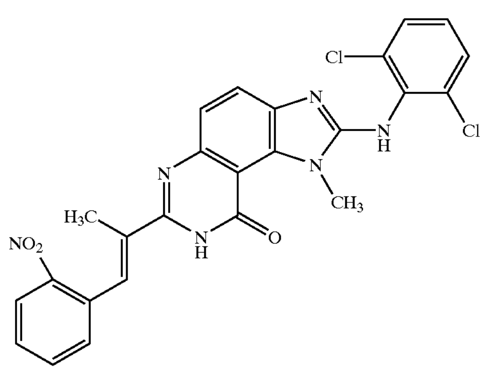 | 290–292 |

-continued

| Ex. No. | Structure | M.P. (° C.) |
|---|---|---|
| 72 | 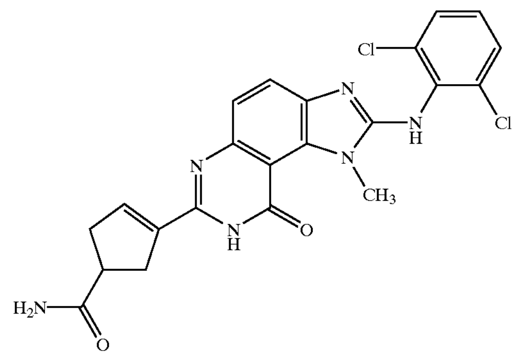 | >215 (dec) |
| 73 | 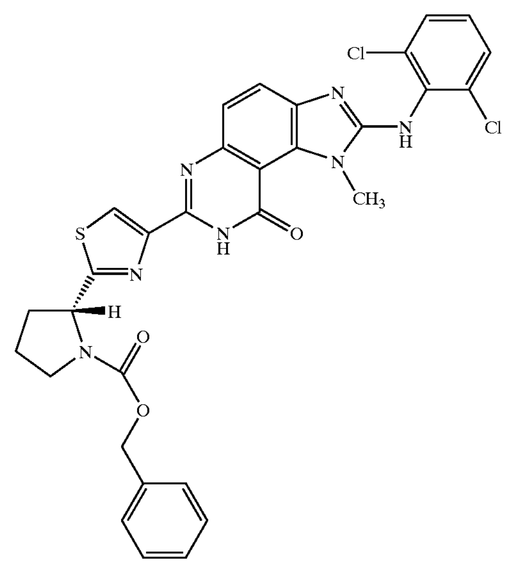 | 209 |
| 74 | 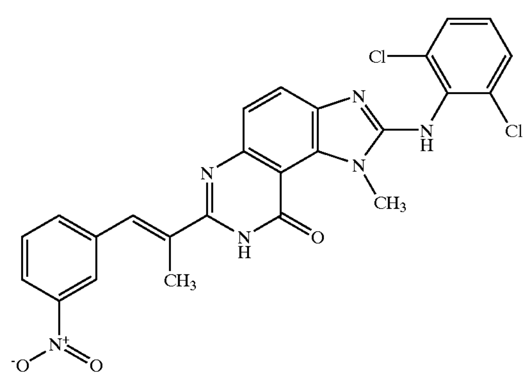 | 254–256 |

-continued

| Ex. No. | Structure | M.P. (° C.) |
|---|---|---|
| 75 | 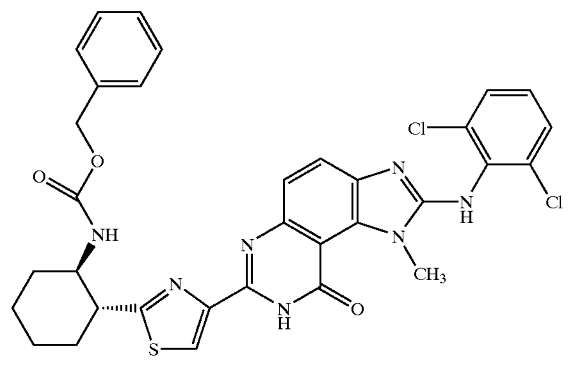 | 163–169 |
| 76 | 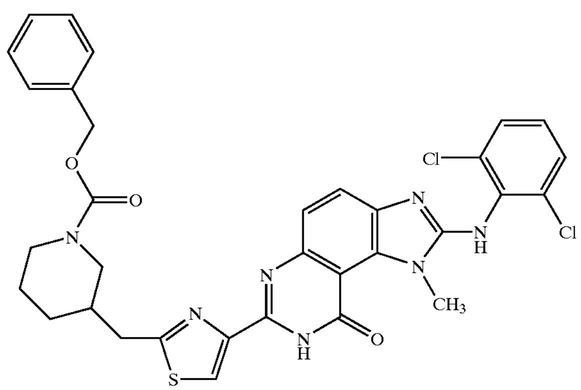 | 155–160 |
| 77 | 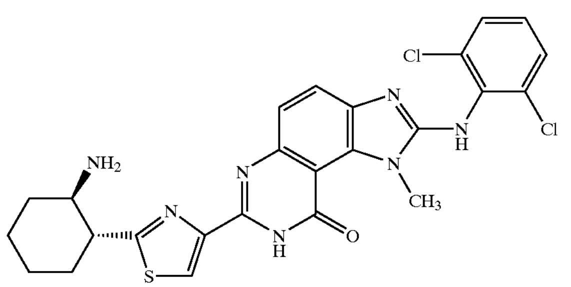 | 295–300 (dec) |
| 78 | 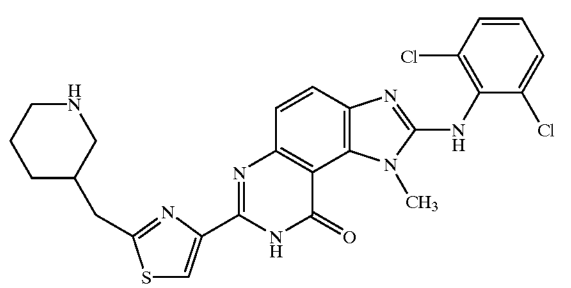 | 161–166 |

| Ex. No. | Structure | M.P. (° C.) |
|---|---|---|
| 79 | 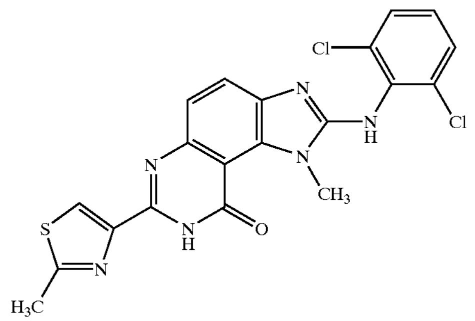 | 295 (dec) |
| 80 | 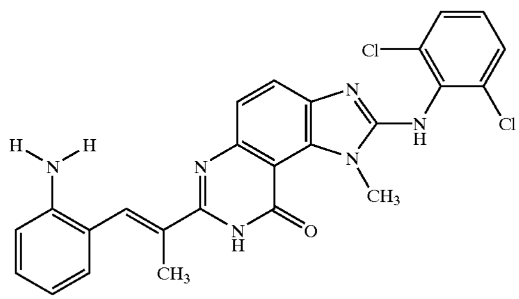 | 310–313 |
| 81 | 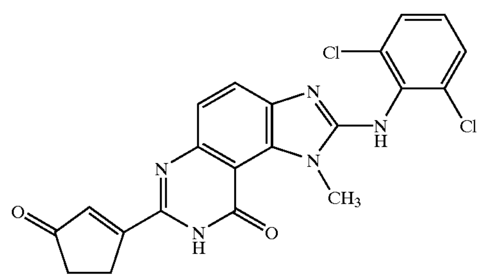 | >300 |
| 82 | 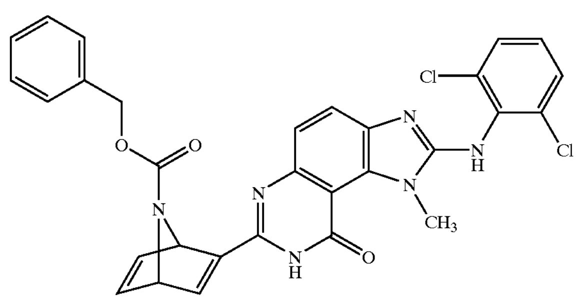 | >275 (dec) |
| 83 | 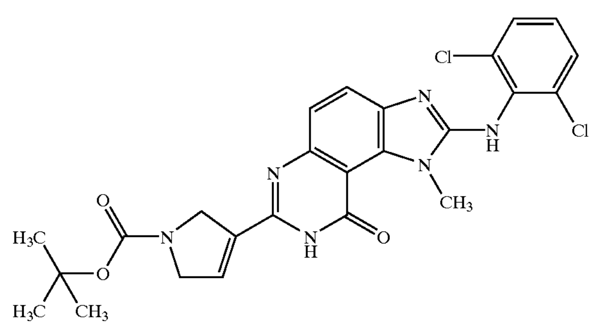 | 206–208 |

-continued
| Ex. No. | Structure | M.P. (° C.) |
| --- | --- | --- |
| 84 | 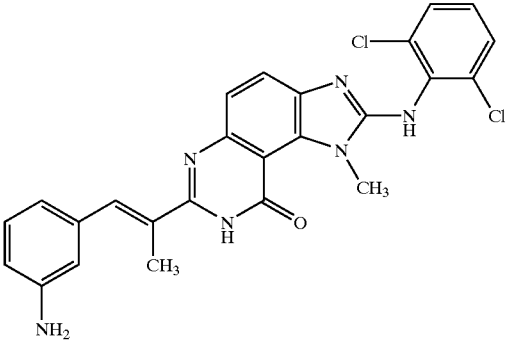 | >300 (dec) |
| 85 | 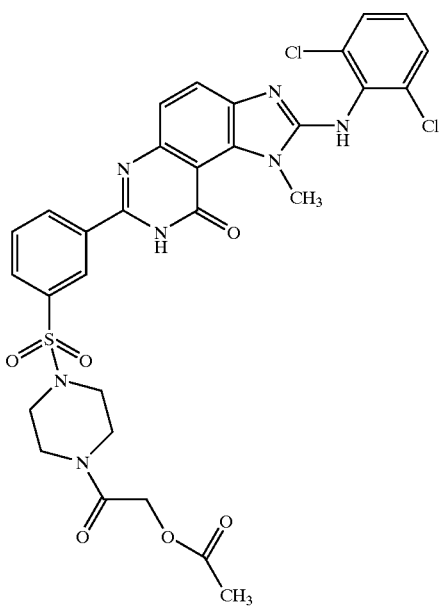 | 246 (dec) |
| 86 | 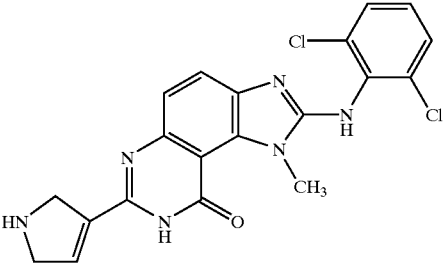 | 240–241 (dec) |

-continued

| Ex. No. | Structure | M.P. (° C.) |
|---|---|---|
| 87 | 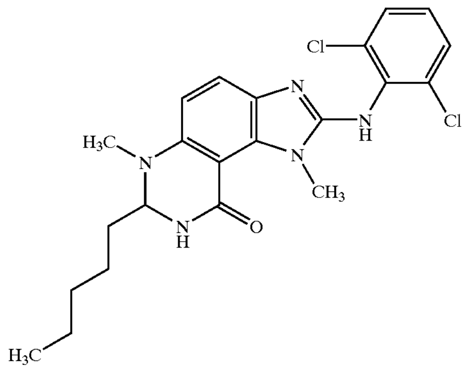 | 126–128 |
| 88 | 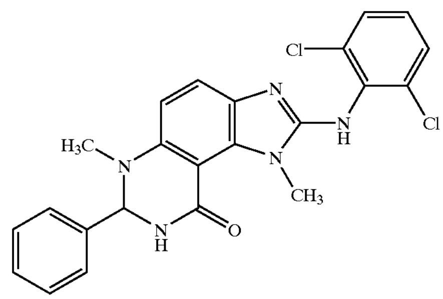 | 228–230 |
| 89 | 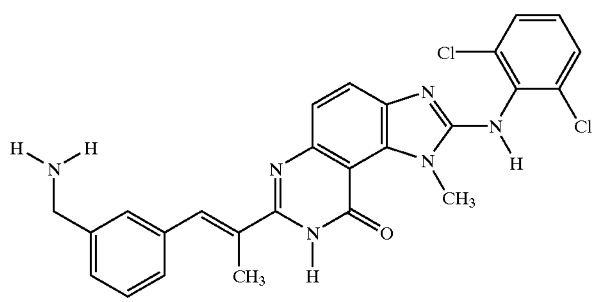 | 197–205 |
| 90 | 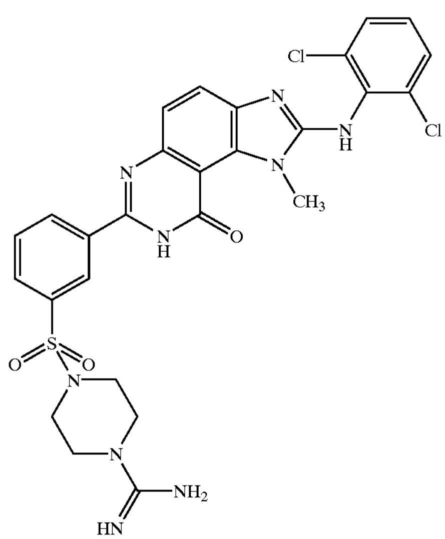 | 215 |

-continued

| Ex. No. | Structure | M.P. (° C.) |
|---|---|---|
| 91 | 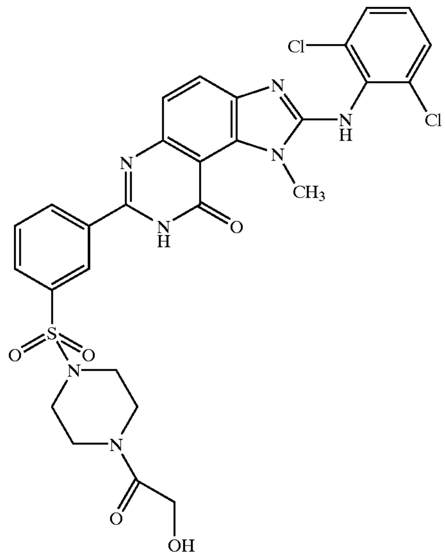 | >300 |
| 92 | 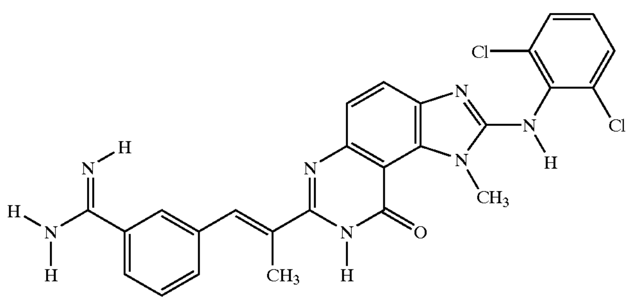 | >300 |
| 93 | 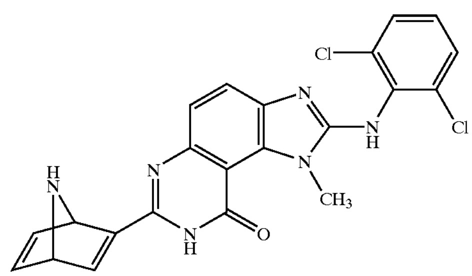 | >300 |
| 94 | 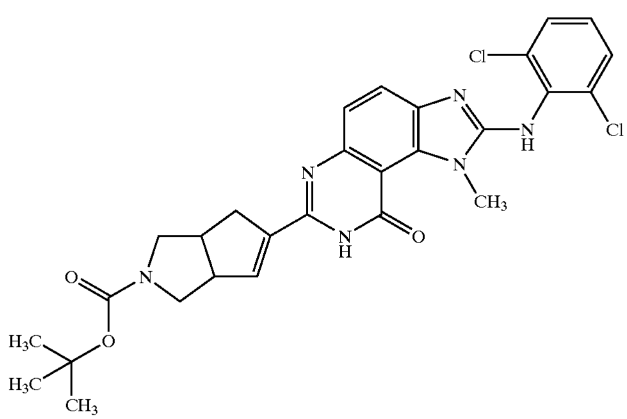 | 210–215 |

-continued

| Ex. No. | Structure | M.P. (° C.) |
|---|---|---|
| 95 | 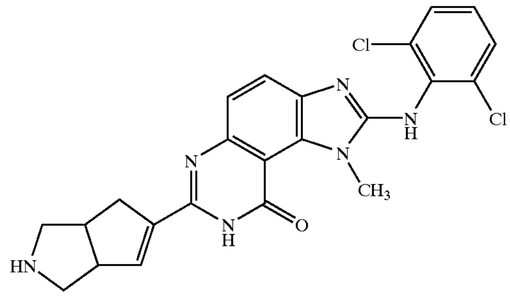 | 265 (dec) |
| 96 | 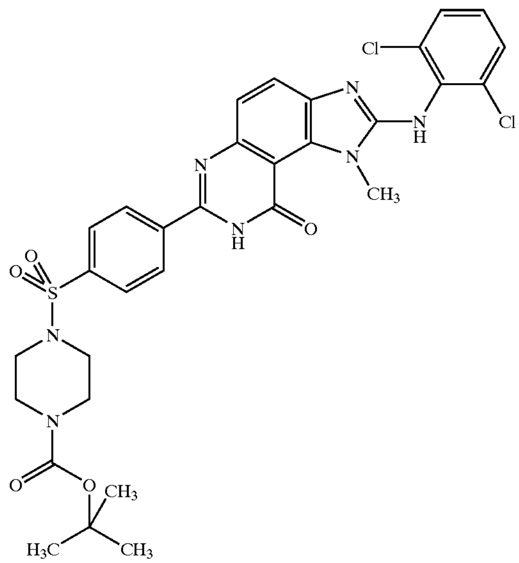 | 190 |
| 97 | 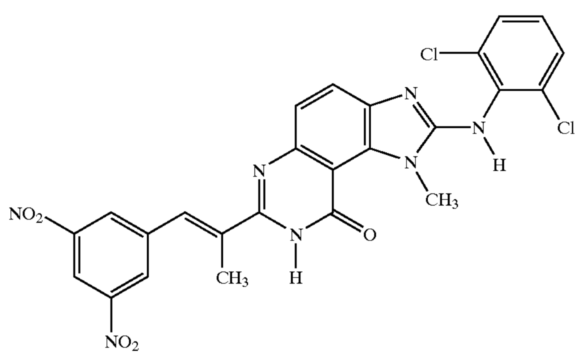 | 315–317 (dec) |
| 98 | 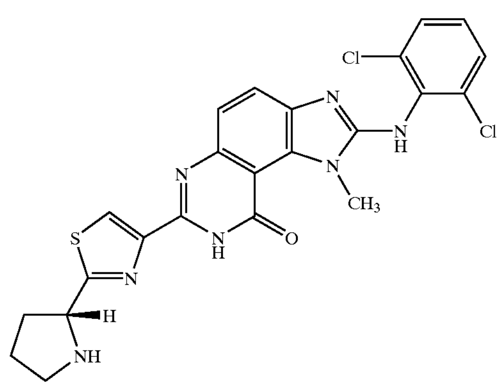 | 290 (dec) |

-continued

| Ex. No. | Structure | M.P. (° C.) |
|---|---|---|
| 99 | 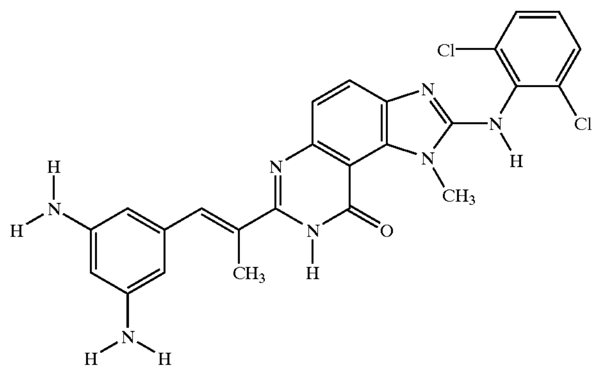 | 195–200 (dec) |
| 100 | 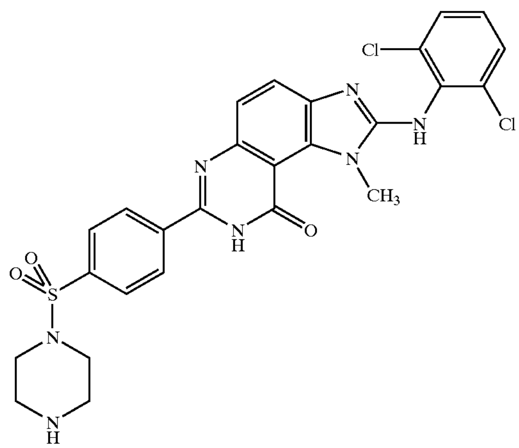 | 246 |
| 101 | 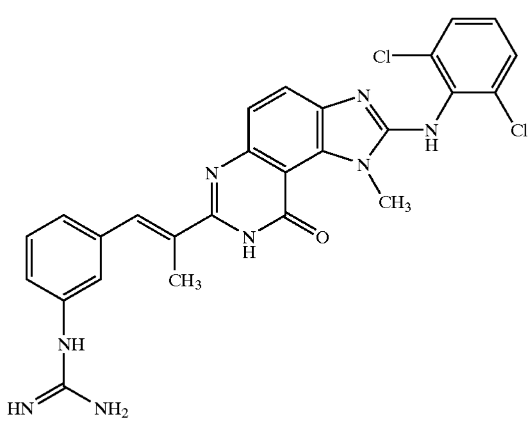 | 170 (dec) |
| 102 | 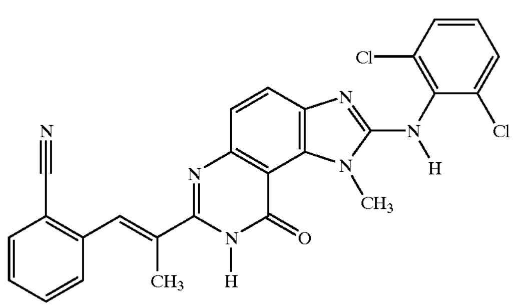 | 284–288 |

-continued

| Ex. No. | Structure | M.P. (° C.) |
|---|---|---|
| 103 | 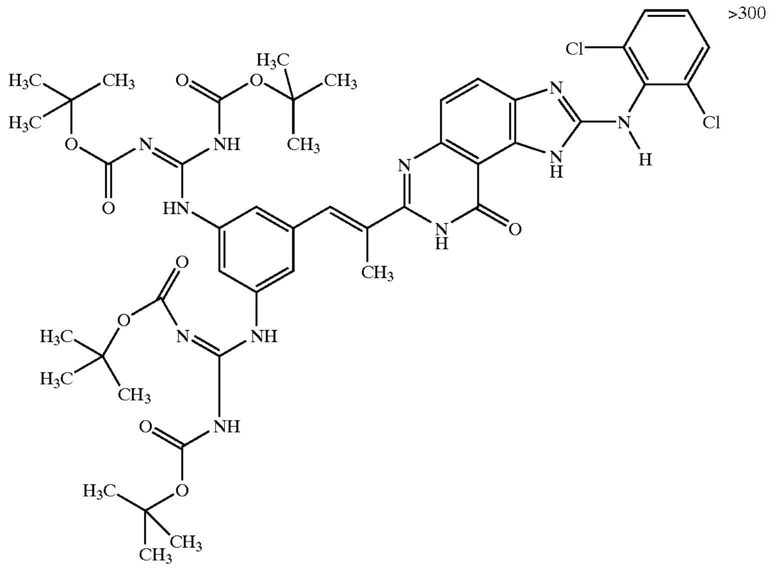 | >300 |
| 104 | 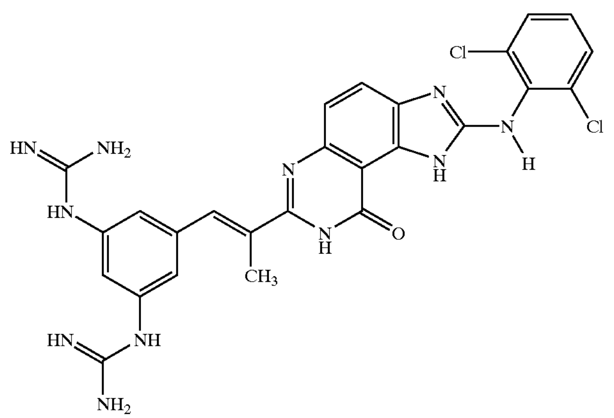 | |

Assessment of Biological Properties
Tyrosine Kinase Inhibition Assay

The inhibition of tyrosine kinases by the compounds of the invention was measured with the following assay.

Kinase Reaction Buffer 50 mM Hepes, pH 7.5, 50 mM KCl, 25 mM $MgCl_2$, 5 mM $MnCl_2$, 100 μM, $Na_3VO_4$, 0.01% CHAPS, 1 mM DTT, and 50 mg/mL BSA, Adenosine 5'-Triphosphate (ATP) solution at 100 mM, pH 7.5 -γ33P-ATP, 2000 Ci/mmol at 10 μCi/μl, -Poly(L-glutamic acid-L-tyrosine, 4:1) or $(E4Y)_n$ at 10 mg/mL in water. Assay: Test compounds, obtained routinely at 5 mg/mL in 100% DMSO were diluted appropriately into complete Kinase assay buffer with 10% DMSO, 10 μl of the 6× compound solution was distributed into each assay well, the final compound concentration for $IC_{50}$ determinations ranged from 200 to 1 μg/mL. [γ33P]-ATP label was prepared as a 10 Ci/mmol working solution in complete Kinase assay buffer. Protein kinase was initiated by adding 10 to 50 ηg of diluted enzyme stock.

Plates were incubated at 30° C. for 30 min. During the incubation period, the MultiScreen harvest plates were pre-wetted with 10% TCA/5% Ppi. 150 μl of TCA/PPi was added to all MultiScreen plate wells after pre-wetting. The kinase reaction was stopped via replica transfer of the polypropylene reaction wells into the MultiScreen plates. The plates were incubated at room temperature for 5 min then vacuum harvested and washed with 200 μl TCA/PPi 3–4 times per well, then 100 μl of cocktail per well was added.

Experimental data consisted of eight (8) compound doses in duplicate with ten (10) enzyme control reaction wells (so-called totals) and six (6) background wells. The results are presented as Percent Inhibition (Mean with S.D.) over the full compound dose range. $IC_{50}$ potency estimates are determined using a floating inhibition maximum (Imax).

All compounds in the synthetic examples and Tables above were evaluated in the tyrosine kinase assay above using p56 lck and were found to have $IC_{50}$'s less than 10 μM.

Representative compounds from the examples above were evaluated in the tyrosine kinase assay above using p60 src and were found to have $IC_{50}$'s less than 10 μM.

Representative compounds from the examples above were evaluated in the tyrosine kinase assay above using PDGFR kinase and were found to have $IC_{50}$'s less than 10 μM.

Inhibition of IL-2 Production

Inactivation of T cells resulting from inhibition of the tyrosine kinase p56 lck can be measured by inhibition of IL-2 production in Jurkat cells. 96-well flat bottom plates were coated with anti-CD3, clone UCHT1, (Immunotech cat. # 1304) at 4 μg/ml in Phosphate Buffered Saline (PBS), 100 μl/well. The solution was prepared by taking 200 μl of 200 μg/ml anti-CD3 stock/ 10 ml PBS. The plate was then incubated at 37° C. for 2 h. Jurkat cells were pelleted and counted. The cells were resuspended at $2.5 \times 10^6$ cells/ml in RPMI, 10% FBS (complete media). Test compounds were diluted from a 5 mg/ml DMSO stock directly into complete media.

10 μl of 20× compound/well was added to a separate plate, followed by 100 μl of cell suspension in triplicate and this plate was preincubated at 37° C. for 30 min. The 96-well plate containing anti-CD3 was aspirated, and the cells and compound transferred to this plate. 100 μl of PMA (Phorbol 12-Myristate 13-Acetate, Sigma cat.#P-8139) at 20 ng/ml was added, and the plate was incubated overnight at 37° C. (PMA stock at 1 mg/ml in ethanol, dilute 10 μl/ml in complete media, then 20 μl/10 mls. in complete media. 100 μl/well=10 ng/ml. final concentration). The next day, the plate was centrifuged at 1500 rpm for 5 min. at room temperature and the supernatants were removed. The supernatants were tested using R&D Systems Quantikine Human IL-2 Kit (cat.#2050). Samples were diluted 1:5 in RPMI1640, and 100 μl/well used in the ELISA. The optical density of each well was determined using a microplate reader set to 450 nm. $EC_{50}$ values were determined using Origin (non-linear regression) or SAS by plotting absorbance vs. concentration of compound.

Representatives from the synthetic examples and the Tables above were screened in this assay and had $IC_{50}$'s below 10 μM.

We claim:

1. A compound of the following formula (I):

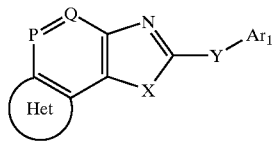

wherein:

Ar$_1$ is an aromatic or nonaromatic carbocycle, heteroaryl or heterocycle; wherein said carbocycle, heteroaryl or heterocycle is optionally substituted by one or more $R_1$, $R_2$ and $R_3$;

X is NH, N—$C_{1-3}$alkyl, N-cyclopropyl, S or O;

Y is $NR_{13}$;

$R_1$ and $R_2$ are the same or different and are selected from H, halogen, CN, NO$_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, di-($C_{1-3}$) alkylaminosulfonyl, NR$_8$R$_9$, aryl, aroyl, aryloxy, arylsulfonyl, heteroaryl and heteroaryloxy; wherein the abovementioned $R_1$ and $R_2$ are optionally partially or fully halogenated or optionally substituted with one to three groups independently selected from the group consisting of oxo, OH, NR$_8$R$_9$, $C_{1-6}$ branched or unbranched alkyl, $C_{3-7}$cycloalkyl, phenyl, naphthyl, heteroaryl, aminocarbonyl and mono- or di($C_{1-3}$) alkylaminocarbonyl;

$R_3$ is selected from the group consisting of H, halogen, OH, (CH$_2$)$_n$NR$_8$R$_9$, (CH$_2$)$_n$CO$_2$R$_{10}$, $C_{1-3}$alkyl optionally substituted with OH, $C_{1-3}$ alkoxy optionally halogenated and $C_{1-3}$ alkylthio;

Het represents a fused heterocyclic ring having a formula A, B or C:

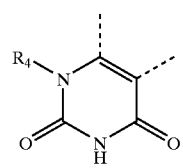

A

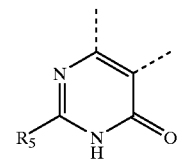

B

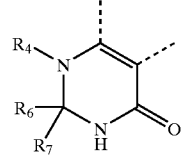

C $R_4$ is selected from H, $C_{1-6}$ alkyl branched or unbranched, saturated or unsaturated, and optionally substituted with phenyl, OH or $C_{1-3}$alkoxy, $C_{3-10}$-cycloalkyl, or $C_{5-8}$cycloalkenyl; or $R_4$ is selected from (CH$_2$)$_m$NR$_8$R$_9$, (CH$_2$)$_m$NR$_8$COR$_{10}$, (CH$_2$)$_n$CO$_2$R$_{10}$, (CH$_2$)$_n$CONR$_8$R$_9$, phenyl, heteroaryl or heterocycle, each phenyl, heteroaryl or heterocycle being optionally substituted with $C_{1-3}$alkyl, $C_{1-3}$alkoxy, (CH$_2$)$_m$NR$_8$R$_9$, OH, SO$_3$H or halogen;

$R_5$ is selected from H, $C_{1-10}$alkyl branched or unbranched, $C_{3-10}$ cycloalkyl, $C_{5-7}$cycloalkenyl, $C_{2-6}$ alkenyl, $C_{2-6}$ alkynyl, $C_{1-6}$acyl, each being optionally substituted with one or more halogen, OH, oxo, CN, $C_{1-6}$alkyl, $C_{2-6}$ alkenyl, $C_{2-6}$ alkynyl, $C_{1-3}$alkoxy, NR$_8$R$_9$, ureido guanidino, NR$_8$COR$_{10}$, SR$_{10}$, CONR$_8$R$_9$, CO$_2$R$_{10}$, $C_{3-10}$ cycloalkyl, $C_{3-10}$cycloalkylidene, $C_{5-7}$cycloalkenyl, aryloxy, arylthio, aryl, heteroaryl or heterocycle; wherein each of $C_{1-6}$alkyl, $C_{2-6}$ alkenyl, $C_{2-6}$ alkynyl, $C_{3-10}$cycloalkyl, $C_{3-10}$cycloalkylidene, $C_{5-7}$cycloalkenyl, aryloxy, arylthio, aryl, heteroaryl or heterocycle is optionally substituted with one or more $C_{1-3}$alkyl, $C_{1-3}$alkoxy, halogen, CN, NO$_2$, amidino, guanidino, (CH$_2$)$_n$NR$_8$R$_9$, or O(CH$_2$)$_{2-4}$NR$_8$R$_9$; wherein one or more of the amino nitrogens in the ureido, amidino or guanidino groups in this paragraph may be optionally substituted with $C_{1-3}$alkyl, phenylC$_{0-3}$alkyl, $C_{1-3}$alkoxy or CO$_2$R$_{10}$;

or $R_5$ is selected from CO$_2$R$_{10}$, NR$_8$R$_9$, CONR$_8$R$_9$, aryl, heteroaryl, heterocycle, aryl-CO—, heteroaryl-CO— or heterocycle-CO—, wherein each aryl, heteroaryl or heterocycle is optionally substituted with one to three:

$C_{1-3}$alkoxy, halogen, NO$_2$, CN, S(O)$_p$NR$_8$R$_9$, CO$_{0-3}$alkylS(O)$_p$, NR$_8$R$_9$, (CH$_2$)$_n$CO$_2$R$_{10}$, (CH$_2$)$_n$CONR$_8$R$_9$, CO(CH$_2$)$_n$NR$_8$R$_9$, O(CH$_2$)$_{2-4}$NR$_8$R$_9$, ureido, guanidino, cycloalkyl, aryl, heteroaryl, heterocycle, cycloalkyl-Z—, aryl-Z—, heteroaryl-Z—, heterocycle-Z—, or $C_{1-3}$alkyl optionally substituted with phenyl or NR$_8$R$_9$, wherein Z is a bridging group selected from $C_{1-10}$ alkylene branched or unbranched, CO, $S(O)_p$, O, S, NH, CONH, NHCO, COO or OOC, and wherein each cycloalkyl, aryl, heteroaryl or heterocycle is optionally substituted with $NO_2$, $C_{1-3}$alkyl, $C_{1-3}$alkoxy, halogen, $CO_2R_{10}$, $(CH_2)_nNR_8R_9$, $O(CH_2)_{2-4}NR_8R_9$, ureido or guanidino, wherein one or more of the amino nitrogens in the ureido or guanidino groups in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-12}$ bridged- or spiro-bicyclic ring system, optionally having one or two double bonds in the ring system, and wherein up to 3 carbon atoms in the ring system may be replaced by heteroatoms selected from N, O and S; and wherein said ring system may be optionally substituted with $C_{1-3}$alkyl, $C_{1-3}$alkoxy, halogen, $CO_2R_{10}$, ureido, guanidino, amidino, $(CH_2)_nNR_8R_9$, or $O(CH_2)_{2-4}NR_8R_9$; wherein one or more of the amino nitrogens in the ureido, guanidino or amidino groups in this paragraph may be optionally substituted with $C_{1-3}$alkyl, phenyl$C_{0-3}$alkyl or $C_{1-3}$alkoxy;

$R_6$ is selected from H, $C_{1-6}$alkyl branched or unbranched, $C_{2-6}$ alkenyl branched or unbranched, $CO_2R_{10}$, $C_{3-8}$cycloalkyl, $C_{3-8}$cycloalkenyl, aryl, aryl$C_{1-3}$alkyl, heteroaryl and heterocyclyl; wherein said $C_{1-6}$alkyl, $C_{2-6}$alkenyl, $C_{3-8}$cycloalkyl, $C_{3-8}$cycloalkenyl, aryl, aryl$C_{1-3}$alkyl, heteroaryl or heterocyclyl are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl, heteroaryl or heterocyclyl;

$R_7$ is H or $C_{1-6}$alkyl;

$R_8$ and $R_9$ are the same or different and are each independently selected from H, OH, $CO_2R_{10}$, $C_{1-10}$ acyl branched or unbranched, $C_{1-3}$alkoxy, $C_{1-6}$alkyl branched or unbranched, $C_{3-6}$alkenyl, $C_{3-8}$cycloalkyl, aryl, aryl$C_{1-3}$alkyl, aroyl, heteroaryl or heterocycle; wherein said alkyl, cycloalkyl, aryl, aryl$C_{1-3}$alkyl, aroyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl;

or $R_8$ and $R_9$ together form a 3–7 member alkylene chain completing a ring about the N atom to which they are attached; wherein said alkylene chain is optionally interrupted by O, $S(O)_p$, $NCOR_{10}$, $NCO_2R_{10}$, $NR_{11}$ or $NC(=NR_{11})NR_{11}R_{12}$; and wherein said ring is optionally substituted by $C_{1-3}$ alkyl, $C_{1-3}$alkoxy, OH or $-(CH_2)_nNR_{11}R_{12}$;

$R_{10}$ is selected from H, $C_{1-6}$alkyl, $C_{3-8}$cycloalkyl, wherein each alkyl or cycloalkyl is optionally substituted with phenyl, OH, $C_{1-3}$alkoxy, $C_{1-3}$alkanoyloxy or $NR_{11}R_{12}$, or $R_{10}$ is phenyl optionally substituted with one to three $C_{1-3}$alkyl, $C_{1-3}$alkoxy, halogen, $(CH_2)_mNR_8R_9$, $(CH_2)_nCONR_8R_9$ or $O(CH_2)_{2-4}NR_8R_9$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$;

$R_{13}$ is H or $C_{1-3}$alkyl;

P and Q are each CH;

m is 1–4;

n is 0–3;

and p is 0–2;

wherein one or more of the primary amine or secondary amine nitrogen atoms in any of the $R_4$, $R_5$, $R_6$ and $R_7$ substituent groups may optionally be protected by a protecting group;

or a pharmaceutically acceptable derivative thereof.

2. A compound according to claim 1 wherein:

$Ar_1$ is
a) a cycloalkyl group selected from cyclopropyl, cyclobutyl, cyclopentanyl, cyclohexanyl and cycloheptanyl;
b) a cycloalkenyl group selected from cyclopentenyl, cyclohexenyl, and cycloheptenyl;
c) an aromatic carbocycle selected from phenyl, naphthyl, indanyl, indenyl, dihydronaphthyl, tetrahydronaphthyl or fluorenyl,
d) a heteroaryl selected from pyridyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl, or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or
e) a heterocycle selected from: pyrrolinyl, pyrrolidinyl, pyrazolinyl, pyrazolidinyl, piperidinyl, morpholinyl, thiomorpholinyl, pyranyl, thiopyranyl, piperazinyl and indolinyl;

wherein each of the above $Ar_1$ are optionally substituted by one or more $R_1$, $R_2$ and $R_3$;

$R_1$ and $R_2$ are as defined in claim 1, and $R_3$ is H, halogen, methyl, methoxy, hydroxymethyl or OH;

$R_4$ is H, $C_{1-3}$alkyl branched or unbranched, saturated or unsaturated, and optionally substituted with OH; or $R_4$ is $(CH_2)_{2-3}NR_8R_9$, $(CH_2)_nCO_2R_{10}$ or $(CH_2)_nCONR_8R_9$;

$R_5$ is selected from H, $C_{1-10}$alkyl branched or unbranched, $C_{3-10}$ cycloalkyl, $C_{5-7}$cycloalkenyl, $C_{2-6}$ alkenyl, $C_{2-6}$ alkynyl, $C_{1-6}$acyl, each being optionally substituted with one or more halogen, OH, oxo, CN, $C_{1-6}$alkyl, $C_{2-6}$ alkenyl, $C_{2-6}$ alkynyl, $C_{1-3}$alkoxy, $NR_8R_9$, ureido, guanidino, $NR_8COR_{10}$, $SR_{10}$, $CONR_8R_9$, $CO_2R_{10}$, $C_{3-10}$ cycloalkyl, $C_{3-10}$cycloalkylidene, $C_{5-7}$cycloalkenyl, aryloxy, arylthio, aryl, heteroaryl or heterocycle; wherein each of $C_{1-6}$alkyl, $C_{2-6}$ alkenyl, $C_{2-6}$ alkynyl, $C_{3-10}$cycloalkyl, $C_{3-10}$cycloalkylidene, $C_{5-7}$cycloalkenyl, aryloxy, arylthio, aryl, heteroaryl or heterocycle is optionally substituted with one or more $C_{1-3}$alkyl, $C_{1-3}$alkoxy, halogen, CN, $NO_2$, amidino, guanidino, $(CH_2)_nNR_8R_9$, or $O(CH_2)_{2-4}NR_8R_9$; wherein one or more of the amino nitrogens in the ureido, amidino or guanidino groups in this paragraph may be optionally substituted with $C_{1-3}$alkyl, phenyl$C_{0-3}$alkyl, $C_{1-3}$alkoxy or $CO_2R_{10}$;

or $R_5$ is selected from $CO_2R_{10}$, $NR_8R_9$, $CONR_8R_9$, aryl, heteroaryl, heterocycle, aryl-CO—, heteroaryl-CO— or heterocycle-CO—, wherein each aryl, heteroaryl or heterocycle is optionally substituted with one to three: $C_{1-3}$alkoxy, halogen, $NO_2$, CN, $S(O)_pNR_8R_9$, $C_{0-3}$alkylS$(O)_p$, $NR_8R_9$, $(CH_2)_nCO_2R_{10}$, $(CH_2)_nCONR_8R_9$, $CO(CH_2)_nNR_8R_9$, $O(CH_2)_{2-4}NR_8R_9$, ureido, guanidino, cycloalkyl, aryl, heteroaryl, heterocycle, cycloalkyl-Z—, aryl-Z—, heteroaryl-Z—, heterocycle-Z—, or $C_{1-3}$alkyl optionally substituted with phenyl or $NR_8R_9$, wherein Z is a bridging group selected from $C_{1-10}$ alkylene branched or unbranched, CO, $S(O)_p$, O, S, NH, CONH, NHCO, COO or OOC, and wherein each cycloalkyl, aryl, heteroaryl or heterocycle is optionally substituted with $NO_2$, $C_{1-3}$alkyl, $C_{1-3}$alkoxy, halogen, $CO_2R_{10}$, $(CH_2)_nNR_8R_9$, $O(CH_2)_{2-4}NR_8R_9$, ureido or guanidino, wherein one or more of the amino nitrogens in the ureido or guanidino groups in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-12}$ bridged- or spiro-bicyclic ring system, optionally having one or two double bonds in the ring system, and wherein up to 3 carbon atoms in the ring system may be replaced by heteroatoms selected from N, O and S; and wherein said ring system may be optionally substituted with $C_{1-3}$alkyl, $C_{1-3}$alkoxy, halogen, $CO_2R_{10}$, ureido, guanidino, amidino, $(CH_2)_nNR_8R_9$, or $O(CH_2)_{2-4}NR_8R_9$; wherein one or more of the amino nitrogens in the ureido, guanidino or amidino groups in this paragraph may be optionally substituted with $C_{1-3}$alkyl, phenyl$C_{0-3}$alkyl or $C_{1-3}$alkoxy;

$R_6$ is selected from H, $C_{1-6}$alkyl branched or unbranched, $C_{2-6}$ alkenyl branched or unbranched, or $CO_2R_{10}$; wherein said $C_{1-6}$alkyl or $C_{1-6}$ alkenyl are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl, heteroaryl or heterocyclyl;

$R_7$ is H or $C_{1-6}$alkyl;

$R_8$ and $R_9$ are the same or different and are each independently selected from H, OH, $C_{1-3}$alkyl branched or unbranched, $CO_2R_{10}$, $C_{3-8}$cycloalkyl, phenyl, benzyl, benzoyl, heteroaryl or heterocycle; wherein said alkyl, cycloalkyl, phenyl, benzyl, benzoyl, heteroaryl or heterocycle are optionally substituted with OH, $C_{1-3}$alkoxy, $C_{1-3}$acyloxy, $CO_2R_{10}$, $NR_{11}R_{12}$, $O(CH_2)_{2-4}NR_{11}R_{12}$, aryl or heteroaryl;

or $R_8$ and $R_9$ together form a 3–7 member alkylene chain completing a ring about the N atom to which they are attached; wherein said alkylene chain is optionally interrupted by O, $S(O)_p$, $NCOR_{10}$, $NCO_2R_{10}$, $NR_{11}$ or $NC(=NR_{11})NR_{11}R_{12}$; and wherein said ring is optionally substituted by $C_{1-3}$ alkyl, $C_{1-3}$alkoxy, OH or —$(CH_2)_nNR_{11}R_{12}$;

$R_{10}$ is H or $C_{1-6}$alkyl optionally substituted with phenyl, OH, $C_{1-3}$alkoxy, $C_{1-3}$alkanoyloxy or $NR_{11}R_{12}$;

$R_{11}$ and $R_{12}$ are each independently selected from H and $C_{1-6}$ alkyl optionally substituted with $C_{1-3}$alkoxy, OH or phenyl;

or $R_{11}$ and $R_{12}$ together form a chain completing a ring, said chain is $(CH_2)_{4-5}$ or $(CH_2)_2O(CH_2)_2$;

and $R_{13}$ is H.

3. A compound according to claim 2 wherein:

$Ar_1$ is phenyl or pyridyl, each optionally substituted by one or more $R_1$, $R_2$ and $R_3$;

X is NH or N—$C_{1-3}$alkyl;

Y is NH;

$R_1$ and $R_2$ are the same or different and selected from: halogen, $C_{1-3}$ alkyl, wherein the $C_{1-3}$ alkyl is optionally partially or fully halogenated, $NO_2$ or $NR_8R_9$;

$R_3$ is H, halogen, methyl or methoxy;

$R_4$ is H, $C_{1-3}$alkyl branched or unbranched, saturated or unsaturated, and optionally substituted with OH; or $R_4$ is $(CH_2)_{2-3}NR_8R_9$ or $CO_2R_{10}$;

$R_5$ is selected from H, $C_{1-3}$alkyl branched or unbranched, $C_{3-8}$ cycloalkyl, $C_{5-7}$cycloalkenyl or $C_{2-4}$ alkenyl, each being optionally substituted with one or more OH, CN, $NR_8R_9$, $CONR_8R_9$, $C_{3-8}$ cycloalkyl, $C_{5-7}$cycloalkenyl, phenyl, heteroaryl or heterocycle; wherein each phenyl, heteroaryl or heterocycle is optionally substituted with one or more $C_{1-3}$alkyl, $C_{1-3}$alkoxy, halogen, CN, $NO_2$, amidino, guanidino, $(CH_2)_nNR_8R_9$, or $O(CH_2)_{2-4}NR_8R_9$; wherein one or more of the amino nitrogens in the amidino or guanidino groups in this paragraph may be optionally substituted with $C_{1-3}$alkyl, phenyl$C_{0-3}$alkyl, $C_{1-3}$alkoxy or $CO_2R_{10}$;

or $R_5$ is selected from $CO_2R_{10}$, $NR_8R_9$, $CONR_8R_9$, phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl, or indolyl-CO—, wherein each phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl or indolyl-CO— is optionally substituted with one to three:

halogen, $NO_2$, $S(O)_pNR_8R_9$, $C_{0-3}$alkylS$(O)_p$, $NR_8R_9$, $(CH_2)_nCO_2R_{10}$, ureido, guanidino, cycloalkyl, phenyl, heteroaryl, heterocycle, cycloalkyl-Z—, phenyl-Z—, heteroaryl-Z—, heterocycle-Z—, or $C_{1-3}$alkyl optionally substituted with phenyl or $NR_8R_9$, wherein Z is a bridging group selected from $C_{1-3}$ alkylene branched or unbranched, O, $S(O)_p$ or NH, and wherein each cycloalkyl, phenyl, heteroaryl or heterocycle is optionally substituted with $NO_2$, $C_{1-3}$alkyl, $C_{1-3}$alkoxy, $CO_2R_{10}$, $(CH_2)_nNR_8R_9$, $O(CH_2)_{2-4}NR_8R_9$ or guanidino, wherein one or more of the amino nitrogens in the guanidino group in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-7}$ bridged-bicyclic ring system, optionally having one or two double bonds in the ring system, and wherein up to 1 carbon atom in the ring system may be replaced by a nitrogen atom; and wherein said ring system may be optionally substituted with $C_{1-3}$alkyl, $C_{1-3}$alkoxy, halogen, $(CH_2)_nNR_8R_9$, or $O(CH_2)_{2-4}NR_8R_9$;

$R_6$ is selected from H, $C_{1-6}$alkyl branched or unbranched or $CO_2R_{10}$;

$R_7$ is H or $C_{1-6}$alkyl;

$R_8$ and $R_9$ are the same or different and are each independently selected from H, $C_{1-3}$alkyl branched or unbranched, $CO_2R_{10}$, phenyl, or benzoyl; wherein said alkyl, phenyl or benzoyl are optionally substituted with OH or $C_{1-3}$alkoxy;

or $R_8$ and $R_9$ together form a —$(CH_2)_2$—$N(CO_2R_{10})$—$(CH_2)_2$— group, a —$(CH_2)_2$—$N(COR_{10})$—$(CH_2)$ 2— group, a —(CH$_2$)$_2$—N(R$_{11}$)—(CH$_2$)$_2$— group or a —(CH$_2$)$_2$—N(C(=NR$_{11}$)NR$_{11}$R$_{12}$)—(CH$_2$)$_2$— group; and wherein said ring is optionally substituted by C$_{1-3}$ alkyl, C$_{1-3}$alkoxy, or OH;

R$_{10}$ is H or C$_{1-6}$alkyl optionally substituted with phenyl, OH, C$_{1-3}$alkoxy, C$_{1-3}$alkanoyloxy or NR$_{11}$R$_{12}$;

R$_{11}$ and R$_{12}$ are each independently selected from H and C$_{1-3}$ alkyl optionally substituted with C$_{1-3}$alkoxy or OH;

or R$_{11}$ and R$_{12}$ together form a chain completing a ring, said chain is (CH$_2$)$_{4-5}$ or (CH$_2$)$_2$O(CH$_2$)$_2$.

4. A compound according to claim 3 wherein:

Ar$_1$ is phenyl;

R$_1$ and R$_2$ are the same or different and selected from: halogen, methyl optionally partially or fully halogenated, NO$_2$ and NH$_2$;

R$_3$ is H, chloro, fluoro, bromo or methoxy;

R$_5$ is selected from C$_{2-4}$ alkenyl, C$_{3-8}$ cycloalkyl or C$_{5-7}$cycloalkenyl, each being optionally substituted with one or more OH, CN, NR$_8$R$_9$, CONR$_8$R$_9$ or phenyl; wherein phenyl is optionally substituted with one or more C$_{1-3}$alkyl, C$_{1-3}$alkoxy, halogen, amidino, guanidino, (CH$_2$)$_n$NR$_8$R$_9$, or O(CH$_2$)$_{2-4}$NR$_8$R$_9$; wherein one or more of the amino nitrogens in the amidino or guanidino groups in this paragraph may be optionally substituted with C$_{1-3}$alkyl, phenylC$_{0-3}$alkyl or C$_{1-3}$alkoxy;

or R$_5$ is selected from phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c]pyrrolyl or indolyl-CO—, wherein each phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c]pyrrolyl or indolyl-CO— is optionally substituted with one to two:

halogen, NO$_2$, SO$_2$NR$_8$R$_9$, NR$_8$R$_9$, (CH$_2$)$_n$CO$_2$R$_{10}$, ureido, cycloalkyl, phenyl, heteroaryl, heterocycle, cycloalkyl-Z—, heteroaryl-Z— or heterocycle-Z—, or C$_{1-3}$alkyl optionally substituted with NR$_8$R$_9$, wherein Z is a bridging group selected from C$_{1-3}$ alkylene branched or unbranched or S(O)$_p$, wherein each cycloalkyl, phenyl, heteroaryl or heterocycle is optionally substituted with NO$_2$, C$_{1-3}$alkyl, CO$_2$R$_{10}$, NR$_8$R$_9$ or guanidino, wherein one or more of the amino nitrogens in the guanidino group in this paragraph may be optionally substituted with C$_{1-3}$alkyl; and wherein each alkyl and phenyl in this paragraph is optionally partially or fully halogenated;

or R$_5$ is a 7-azabicyclo[2.2.1]heptane ring system, optionally having one or two double bonds in the ring system, wherein said ring system may be optionally substituted with C$_{1-3}$alkyl, C$_{1-3}$alkoxy, halogen, (CH$_2$)$_n$NR$_8$R$_9$, or O(CH$_2$)$_{2-4}$NR$_8$R$_9$;

R$_6$ is selected from H or C$_{1-3}$alkyl branched or unbranched;

R$_7$ is H or C$_{1-3}$alkyl;

R$_8$ and R$_9$ are the same or different and are each independently selected from H or C$_{1-3}$alkyl branched or unbranched; wherein said alkyl is optionally substituted with OH or C$_{1-3}$alkoxy;

or R$_8$ and R$_9$ together form a —(CH$_2$)$_2$—N(CO$_2$R$_{10}$)—(CH$_2$)$_2$—, a —(CH$_2$)$_2$—N(COR$_{10}$)—(CH$_2$)$_2$— group, a —(CH$_2$)$_2$—N(R$_{11}$)—(CH$_2$)$_2$— group or a —(CH$_2$)$_2$—N(C(=NR$_{11}$)NR$_{11}$R$_{12}$)—(CH$_2$)$_2$— group; and wherein said ring is optionally substituted by C$_{1-3}$ alkyl, C$_{1-3}$alkoxy, or OH;

R$_{10}$ is H or C$_{1-3}$alkyl optionally substituted with phenyl, OH or C$_{1-3}$alkanoyloxy; and R$_{11}$ is selected from H and C$_{1-3}$ alkyl.

5. A compound according to any of claims 1, 2, 3 or 4, wherein the Het represents a fused ring having formula B:

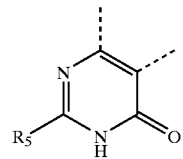

B wherein R$_5$ is as defined in claims 1, 2, 3 or 4.

6. A compound according to claim 1, represented by the following formula (I'):

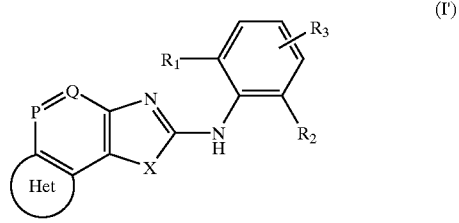

(I')

wherein R$_1$, R$_2$, R$_3$, X, P, Q and Het are as defined in claim 1;

or a pharmaceutically acceptable derivative thereof.

7. A compound according to claim 6 wherein:

X is NH or N—C$_{1-3}$alkyl;

R$_1$ and R$_2$ are the same or different and selected from: halogen, C$_{1-3}$ alkyl, wherein the C$_{1-3}$ alkyl is optionally partially or fully halogenated, NO$_2$ or NR$_8$R$_9$;

R$_3$ is H, halogen, methyl or methoxy;

R$_4$ is H, C$_{1-3}$alkyl branched or unbranched, saturated or unsaturated, and optionally substituted with OH; or R$_4$ is (CH$_2$)$_{2-3}$NR$_8$R$_9$ or CO$_2$R$_{10}$;

R$_5$ is selected from H, C$_{1-3}$alkyl branched or unbranched, C$_{3-8}$ cycloalkyl, C$_{5-7}$cycloalkenyl or C$_{2-4}$ alkenyl, each being optionally substituted with one or more OH, CN, NR$_8$R$_9$, CONR$_8$R$_9$, C$_{3-8}$ cycloalkyl, C$_{5-7}$cycloalkenyl, phenyl, heteroaryl or heterocycle; wherein each phenyl, heteroaryl or heterocycle is optionally substituted with one or more C$_{1-3}$alkyl, C$_{1-3}$alkoxy, halogen, CN, NO$_2$, amidino, guanidino, (CH$_2$)$_n$NR$_8$R$_9$, or O(CH$_2$)$_{2-4}$NR$_8$R$_9$; wherein one or more of the amino nitrogens in the amidino or guanidino groups in this paragraph may be optionally substituted with C$_{1-3}$alkyl, phenylC$_{0-3}$alkyl, C$_{1-3}$alkoxy or CO$_2$R$_{10}$;

or R$_5$ is selected from CO$_2$R$_{10}$, NR$_8$R$_9$, CONR$_8$R$_9$, phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c]pyrrolyl, benzoyl, or indolyl-CO—, wherein each phenyl, furyl, thienyl, oxazolyl, thiazolyl, imidazolyl, pyridinyl, benzofuranyl, benzimidazolyl, 1,2,5,6-tetrahydro-pyridinyl, pyrrolinyl, 1,2,3,3a,4,6a-hexahydro-cyclopenta[c] pyrrolyl, benzoyl or indolyl-CO— is optionally substituted with one to three:

halogen, NO$_2$, S(O)$_p$NR$_8$R$_9$, CO$_3$alkylS(O)$_p$, NR$_8$R$_9$, (CH$_2$)$_n$CO$_2$R$_{10}$, ureido, guanidino, cycloalkyl, phenyl, heteroaryl, heterocycle, cycloalkyl-Z—, phenyl-Z—, heteroaryl-Z—, heterocycle-Z—, or $C_{1-3}$alkyl optionally substituted with phenyl or $NR_8R_9$, wherein Z is a bridging group selected from $C_{1-3}$ alkylene branched or unbranched, O, S(O)$_p$ or NH, and wherein each cycloalkyl, phenyl, heteroaryl or heterocycle is optionally substituted with $NO_2$, $C_{1-3}$alkyl, $C_{1-3}$alkoxy, $CO_2R_{10}$, $(CH_2)_nNR_8R_9$, $O(CH_2)_{2-4}NR_8R_9$ or guanidino, wherein one or more of the amino nitrogens in the guanidino group in this paragraph may be optionally substituted with $C_{1-3}$alkyl, phenyl$C_{0-3}$alkyl or $C_{1-3}$alkoxy; and wherein each alkyl, alkoxy and phenyl in this paragraph is optionally partially or fully halogenated;

or $R_5$ is a $C_{6-7}$ bridged-bicyclic ring system, optionally having one or two double bonds in the ring system, and wherein up to 1 carbon atom in the ring system may be replaced by a nitrogen atom; and wherein said ring system may be optionally substituted with $C_{1-3}$alkyl, $C_{1-3}$alkoxy, halogen, $(CH_2)_nNR_8R_9$, or $O(CH_2)_{2-4}NR_8R_9$;

$R_6$ is selected from H, $C_{1-6}$alkyl branched or unbranched or $CO_2R_{10}$;

$R_7$ is H or $C_{1-6}$alkyl;

$R_8$ and $R_9$ are the same or different and are each independently selected from H, $C_{1-3}$alkyl branched or unbranched, $CO_2R_{10}$, phenyl, or benzoyl; wherein said alkyl, phenyl or benzoyl are optionally substituted with OH or $C_{1-3}$alkoxy;

or $R_9$ and $R_9$ together form a —(CH$_2$)$_2$—N(CO$_2$R$_{10}$)—(CH$_2$)$_2$— group, a —(CH$_2$)$_2$—N(COR$_{10}$)—(CH$_2$)$_2$— group, a —(CH$_2$)$_2$—N(R$_{11}$)—(CH$_2$)$_2$— group or a —(CH$_2$)$_2$—N(C(=NR$_{11}$)NR$_{11}$R$_{12}$)—(Cl$_2$)$_2$— group; and wherein said ring is optionally substituted by $C_{1-3}$ alkyl, $C_{1-3}$alkoxy, or OH;

$R_{10}$ is H or $C_{1-6}$alkyl optionally substituted with phenyl, OH, $C_{1-3}$alkoxy, $C_{1-3}$alkanoyloxy or $NR_{11}R_{12}$; and $R_{11}$ and $R_{12}$ are each independently selected from H and $C_{1-3}$ alkyl optionally substituted with $C_{1-3}$alkoxy or OH;

or $R_{11}$ and $R_{12}$ together form a chain completing a ring, said chain is $(CH_2)_{4-5}$ or $(CH_2)_2O(CH_2)_2$.

8. A compound according to claim 7, wherein $R_1$ and $R_2$ are the same or different and selected from: halogen, methyl optionally partially or fully halogenated, $NO_2$ and $NH_2$;

$R_3$ is H, chloro, fluoro, bromo or methoxy;

$R_5$ is selected from $C_{2-4}$ alkenyl, $C_{3-8}$ cycloalkyl or $C_{5-7}$cycloalkenyl, each being optionally substituted with one or more OH, CN, $NR_8R_9$, $CONR_8R_9$ or phenyl; wherein phenyl is optionally substituted with one or more $C_{1-3}$alkyl, $C_{1-3}$alkoxy, halogen, amidino, guanidino, $(CH_2)_nNR_8R_9$, or $O(CH_2)_{2-4}NR_8R_9$; wherein one or more of the amino nitrogens in the amidino or guanidino groups in this paragraph may be optionally substituted with $C_{1-3}$alkyl, phenyl$C_{0-3}$alkyl or $C_{1-3}$alkoxy;

or $R_5$ is selected from phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c]pyrrolyl or indolyl-CO—, wherein each phenyl, furyl, thienyl, oxazolyl, thiazolyl, pyridinyl, benzofuranyl, 1,2,5,6-tetrahydropyridinyl, pyrrolinyl, 1,2,3,3a,4,6a-hexahydro-cyclopenta[c] pyrrolyl or indolyl-CO— is optionally substituted with one to two:

halogen, $NO_2$, $SO_2NR_8R_9$, $NR_8R_9$, $(CH_2)_nCO_2R_{10}$, ureido, cycloalkyl, phenyl, heteroaryl, heterocycle, cycloalkyl-Z—, heteroaryl-Z— or heterocycle-Z—, or $C_{1-3}$alkyl optionally substituted with $NR_8R_9$, wherein Z is a bridging group selected from $C_{1-3}$ alkylene branched or unbranched or S(O)$_p$, wherein each cycloalkyl, phenyl, heteroaryl or heterocycle is optionally substituted with $NO_2$, $C_{1-3}$alkyl, $CO_2R_{10}$, $NR_8R_9$ or guanidino, wherein one or more of the amino nitrogens in the guanidino group in this paragraph may be optionally substituted with $C_{1-3}$alkyl; and wherein each alkyl and phenyl in this paragraph is optionally partially or fully halogenated;

or $R_5$ is a 7-azabicyclo[2.2.1]heptane ring system, optionally having one or two double bonds in the ring system, wherein said ring system may be optionally substituted with $C_{1-3}$alkyl, $C_{1-3}$alkoxy, halogen, $(CH_2)_nNR_8R_9$, or $O(CH_2)_{2-4}NR_8R_9$;

$R_6$ is selected from H or $C_{1-3}$alkyl branched or unbranched;

$R_7$ is H or $C_{1-3}$alkyl;

$R_8$ and $R_9$ are the same or different and are each independently selected from H or $C_{1-3}$alkyl branched or unbranched; wherein said alkyl is optionally substituted with OH or $C_{1-3}$alkoxy;

or $R_8$ and $R_9$ together form a —(CH$_2$)$_2$—N(CO$_2$R$_{10}$)—(CH$_2$)$_2$—, a —(CH$_2$)$_2$—N(COR$_{10}$)—(CH$_2$)$_2$— group, a —(CH$_2$)$_2$—N(R$_{11}$)—(CH$_2$)$_2$— group or a —(CH$_2$)$_2$—N(C(=NR$_{11}$)NR$_{11}$R$_{12}$)—(CH$_2$)$_2$— group; and wherein said ring is optionally substituted by $C_{1-3}$ alkyl, $C_{1-3}$alkoxy, or OH;

$R_{10}$ is H or $C_{1-3}$alkyl optionally substituted with phenyl, OH or $C_{1-3}$alkanoyloxy; and $R_{11}$ is selected from H and $C_{1-3}$ alkyl.

9. A compound according to any of claims 6, 7 or 8, wherein the Het represents a fused ring having formula B:

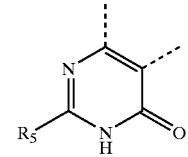

wherein $R_5$ is as defined in claims 6, 7 or 8.

10. A compound according to claim 1, represented by the following formula (Ib):

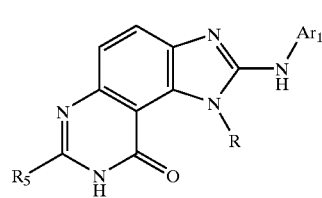

wherein R is H, $C_{1-3}$alkyl or cyclopropyl, and $Ar_1$ and $R_5$ are as defined in claim 1;

or a pharmaceutically acceptable derivative thereof.

11. A compound selected from the group consisting of:
2-(2,6-Dichlorophenylamino)-1-methyl-1,8-dihydro-9H-imidazo[4,5-f]quinazoline-9-one;
2-(2,6-Dichlorophenylamino)-7-furan-2-yl-1-methyl-1,8-dihydro-9H-imidazo[4,5-f]quinazoline-9-one;

2-(2,6-Dichlorophenylamino)-1-methyl-7-phenyl-1,8-dihydro-9H-imidazo[4,5-f]quinazoline-9-one;

2-(2,6-Dichlorophenylamino)-1-methyl-7-(3-nitrophenyl)-1,8-dihydro-9H-imidazo[4,5-f]quinazoline-9-one;

7-(3-Aminophenyl)-2-(2,6-dichlorophenylamino)-1-methyl-1,8-dihydro-9H-imidazo[4,5-f]quinazoline-9-one;

1-{3-[2-(2,6-Dichlorophenylamino)-1-methyl-9-oxo-1,8,-dihydro-9H-imidazo[4,5-f]quinazolin-7-yl]-phenyl}-3-ethylurea;

2-(2,6-Dichlorophenylamino)-1-methyl-7-vinyl-1,8-dihydro-9H-imidazo[4,5-f]quinazoline-9-one;

2-(2,6-Dichlorophenylamino)-1-methyl-7-thiophen-2-yl-1,8-dihydro-9H-imidazo[4,5-f]quinazoline-9-one;

2-(2,6-Dichlorophenylamino)-1-methyl-7-[2-(3-nitrophenyl)-thiazol-4-yl]-1,8-dihydro-9H-imidazo[4,5-f]quinazoline-9-one;

2-(2,6-Dichlorophenylamino)-7-imidazol-2-yl-1-methyl-1,8-dihydro-9H-imidazo[4,5-f]quinazoline-9-one;

2-(2,6-Dichlorophenylamino)-1-methyl-7-(2-phenyloxazol-5-yl)-1,8-dihydro-9H-imidazo[4,5-f]quinazoline-9-one;

2-(2,6-Dichlorophenylamino)-1-methyl-9-oxo-1,8,-dihydro-9H-imidazo[4,5-f]quinazoline-7-carboxamide;

2-(2,6-Dichlorophenylamino)-1-methyl-7-(2-methylpropen-1-yl)-1,8-dihydro-9H-imidazo[4,5-f]quinazoline-9-one;

2-(2,6-Dichlorophenylamino)-1-methyl-7-pyridin-2-yl-1,8-dihydro-9H-imidazo[4,5-f]quinazoline-9-one;

2-(2,6-Dichlorophenylamino)-1-methyl-7-pyridin-3-yl-1,8-dihydro-9H-imidazo[4,5-f]quinazoline-9-one;

2-(2,6-Dichlorophenylamino)-1-methyl-1H-imidazo[4,5-f]quinazoline-7,9-6H,8H-dione;

2-(2,6-Dichlorophenylamino)-1-methyl-7-propen-2-yl-1,8-dihydro-9H-imidazo[4,5-f]quinazoline-9-one;

7-Cyclopent-1-enyl-2-(2,6-dichlorophenylamino)-1-methyl-1,8-dihydro-9H-imidazo[4,5-f]quinazoline-9-one;

7-[2-(3-Aminophenyl)-thiazol-4-yl]-2-(2,6-dichlorophenylamino)-1-methyl-1,8-dihydro-9H-imidazo[4,5-f]quinazoline-9-one;

Ethyl 2-(2,6-Dichlorophenylamino)-1-methyl-9-oxo-1,8,-dihydro-9H-imidazo[4,5-f]quinazoline-7-carboxylate;

7-Benzofuran-2yl-2-(2,6-dichlorophenylamino)-1-methyl-1,8-dihydro-9H-imidazo[4,5-f]quinazoline-9-one;

2-(2,6-Dichlorophenylamino)-1-methyl-7-(1-methylprop-1-enyl)-1,8-dihydro-9H-imidazo[4,5-f]quinazoline-9-one;

2-(2,6-Dichlorophenylamino)-1-methyl-7-(2-methyloxazol-5-yl)-1,8-dihydro-9H-imidazo[4,5-f]quinazoline-9-one;

2-(2,6-Dichlorophenylamino)-7-(1H-indole-3-carbonyl)-1-methyl-1,8-dihydro-9H-imidazo[4,5-f]quinazoline-9-one;

2-(2,6-Dichlorophenylamino)-1-methyl-7-(3-piperazin-1-yl-cyclopent-1-enyl)-1,8-dihydro-9H-imidazo[4,5-f]quinazoline-9-one;

7-Cyclohex-1-enyl-2-(2,6-dichlorophenylamino)-1-methyl-1,8-dihydro-9H-imidazo[4,5-f]quinazoline-9-one;

2-(2,6-Dichlorophenylamino)-1-methyl-7-(1-methyl-1,2,5,6-tetrahydro-pyridin-3-yl)-1,8-dihydro-9H-imidazo[4,5-f]quinazoline-9-one;

2-(2,6-Dichlorophenylamino)-1-methyl-7-[5-(2-nitrophenyl)-furan-2-yl]-1,8-dihydro-9H-imidazo[4,5-f]quinazoline-9-one;

2-(2,6-Dichlorophenylamino)-7-furan-3-yl-1-methyl-1,8-dihydro-9H-imidazo[4,5-f]quinazoline-9-one;

7-(5-Bromofuran-2-yl)-2-(2,6-dichlorophenylamino)-1-methyl-1,8-dihydro-9H-imidazo[4,5-f]quinazoline-9-one;

2-(2,6-Dichlorophenylamino)-1-methyl-7-(3-methylfuran-2-yl)-1,8-dihydro-9H-imidazo[4,5-f]quinazoline-9-one;

7-Cyclopropyl-2-(2,6-dichlorophenylamino)-1-methyl-1,8-dihydro-9H-imidazo[4,5-f]quinazoline-9-one;

2-(2,6-Dichlorophenylamino)-1-methyl-7-[3-(4-methylpiperazine-1-sulfonyl)-phenyl]-1,8-dihydro-9H-imidazo[4,5-f]quinazoline-9-one;

4-{3-[2-(2,6-Dichlorophenylamino)-1-methyl-9-oxo-1,8,-dihydro-9H-imidazo[4,5-f]quinazolin-7-yl]-cyclopent-2-enyl}-piperazine-1-carboxylic acid tert-butyl ester;

2-(2,6-Dichlorophenylamino)-7-(3-hydroxycyclopent-1-enyl)-1-methyl-1,8-dihydro-9H-imidazo[4,5-f]quinazoline-9-one;

2-(2,6-Dichlorophenylamino)-1-methyl-7-[3-(piperazine-1-sulfonyl)-phenyl]-1,8-dihydro-9H-imidazo[4,5-f]quinazoline-9-one;

3-[2-(2,6-Dichlorophenylamino)-1-methyl-9-oxo-1,8-dihydro-9H-imidazo[4,5-f]quinazolin-7-yl]-cyclopent-3-enecarbonitrile;

7-Amino-2-(2,6-dichlorophenylamino)-1-methyl-1,8-dihydro-9H-imidazo[4,5-f]quinazoline-9-one;

3-{2-[2-(2,6-Dichlorophenylamino)-1-methyl-9-oxo-1,8,-dihydro-9H-imidazo[4,5-f]quinazolin-7-yl]-propenyl}-benzonitrile;

3-[2-(2,6-Dichlorophenylamino)-1-methyl-9-oxo-1,8,-dihydro-9H-imidazo[4,5-f]quinazolin-7-yl]-cyclopent-3-enecarboxamide;

2-{4-[2-(2,6-Dichlorophenylamino)-1-methyl-9-oxo-1,8,-dihydro-9H-imidazo[4,5-f]quinazolin-7-yl]-thiazol-2-yl}-pyrrolidine-1-carboxylic acid benzyl ester;

2-(2,6-Dichlorophenylamino)-1-methyl-7-[1-methyl-2-(3-nitrophenyl)-vinyl]-1,8-dihydro-9H-imidazo[4,5-f]quinazoline-9-one;

3-{4-[2-(2,6-Dichlorophenylamino)-1-methyl-9-oxo-1,8,-dihydro-9H-imidazo[4,5-f]quinazolin-7-yl]-thiazol-2-ylmethyl}-piperidine-1-carboxylic acid benzyl ester;

7-[2-(2-Aminocyclohexyl)-thiazol-4-yl]-2-(2,6-dichlorophenylamino)-1-methyl-1,8-dihydro-9H-imidazo[4,5-f]quinazoline-9-one;

2-(2,6-Dichlorophenylamino)-1-methyl-7-(2-piperidin-3-ylmethyl-thiazol-4-yl)-1,8-dihydro-9H-imidazo[4,5-f]quinazoline-9-one;

2-(2,6-Dichlorophenylamino)-1-methyl-7-(2-methylthiazol-4-yl)-1,8-dihydro-9H-imidazo[4,5-f]quinazoline-9-one;

2-(2,6-Dichlorophenylamino)-1-methyl-7-(3-oxocyclopent-1-enyl)-1,8-dihydro-9H-imidazo[4,5-f]quinazoline-9-one;

3-[2-(2,6-Dichlorophenylamino)-1-methyl-9-oxo-1,8,-dihydro-9H-imidazo[4,5-f]quinazolin-7-yl]-2,5-dihydro-pyrrole-1-carboxylic acid tert-butyl ester;

7-[2-(3-Aminophenyl)-1-methylvinyl]-2-(2,6-dichlorophenylamino)-1-methyl-1,8-dihydro-9H-imidazo[4,5-f]quinazoline-9-one;

Acetic acid 2-(4-{3-[2-(2,6-Dichlorophenylamino)-1-methyl-9-oxo-1,8,-dihydro-9H-imidazo[4,5-f]quinazolin-7-yl]-benzenesulfonyl}-piperazin-1yl)-2-oxoethyl ester;

2-(2,6-Dichlorophenylamino)-7-(2,5-dihydro-1H-pyrrol-3-yl)-1-methyl-1,8-dihydro-9H-imidazo[4,5-f]quinazoline-9-one;

7-[2-(3-Aminomethylphenyl)-1-methylvinyl]-2-(2,6-dichlorophenylamino)-1-methyl-1,8-dihydro-9H-imidazo[4,5-f]quinazoline-9-one;

4-{3-[2-(2,6-Dichlorophenylamino)-1-methyl-9-oxo-1,8,-dihydro-9H-imidazo[4,5-f]quinazolin-7-yl]-benzenesulfonyl}-piperazine-1-carboxamidine;

2-(2,6-Dichlorophenylamino)-7-{3-[4-(2-hydroxyacetyl)-piperazine-1-sulfonyl]-phenyl}-1-methyl-1,8-dihydro-9H-imidazo[4,5-f]quinazoline-9-one;

3-{2-[2-(2,6-Dichlorophenylamino)-1-methyl-9-oxo-1,8,-dihydro-9H-imidazo[4,5-f]quinazolin-7-yl]-propenyl}-benzamidine;

7-(7-Azabicyclo[2.2.1]hepta-2,5-dien-2-yl)-2-(2,6-dichlorophenylamino)-1-methyl-1,8-dihydro-9H-imidazo[4,5-f]quinazoline-9-one;

5-[2-(2,6-Dichlorophenylamino)-1-methyl-9-oxo-1,8,-dihydro-9H-imidazo[4,5-f]quinazolin-7-yl]-3,3a,4,6a-tetrahydro-1H-cyclopenta[c]pyrrole-2-carboxylic acid tert-butyl ester;

2-(2,6-Dichlorophenylamino)-7-(1,2,3,3a,4,6a-hexahydro-cyclopenta[c]pyrrol-5-yl)-1-methyl-1,8-dihydro-9H-imidazo[4,5-f]quinazoline-9-one;

2-(2,6-Dichlorophenylamino)-1-methyl-7-(2-pyrrolidin-2yl-thiazol-4-yl)-1,8-dihydro-9H-imidazo[4,5-f]quinazoline-9-one;

7-[2-(3,5-Diaminophenyl)-1-methylvinyl]-2-(2,6-dichlorophenylamino)-1-methyl-1,8-dihydro-9H-imidazo[4,5-f]quinazoline-9-one; and 2-(2,6-Dichlorophenylamino)-1-methyl-7-[4-(piperazine-1-sulfonyl)-phenyl]-1,8-dihydro-9H-imidazo[4,5-f]quinazoline-9-one;

and the pharmaceutically acceptable derivatives thereof.

12. A pharmaceutical composition comprising a therapeutically effective amount of a compound according to claims 1, 6 or 10.

13. A method of treating an autoimmune disease, cancer or a cerebral ischemic condition said method comprising administering to a patient in need thereof a therapeutically effective amount of a compound according to claims 1, 6 or 10.

14. A method according to claim 13, wherein the autoimmune disease is selected from rheumatoid arthritis, multiple sclerosis, Guillain-Barre syndrome, Crohn's disease, ulcerative colitis, psoriasis, graft versus host disease, systemic lupus erythematosus, insulin-dependent diabetes mellitus and asthma.

15. A method according to claim 13, wherein the cancer is selected from a src-dependent tumor or a PDGF-dependent tumor.

16. A method according to claim 15, wherein the src-dependent tumor is selected from mammary carcinoma, colon carcinoma, melanoma and sarcoma.

17. A method according to claim 15, wherein the PDGF-dependent tumor is selected from ovarian cancer, prostate cancer and glioblastoma.

18. A method according to claim 13, wherein the cerebral ischemic condition is stroke.

19. A method of treating a disease selected from osteoporosis, Paget's disease, bone inflammation, and joint inflammation , said method comprising administering to a patient in need thereof a therapeutically effective amount of a compound according to claims 1, 6 or 10.

20. A method of treating a disease selected from fibrotic diseases, restenosis and atherosclerosis , said method comprising administering to a patient in need thereof a therapeutically effective amount of a compound according to claims 1, 6 or 10.

21. A method of enhancing or potentiating the effectiveness of radiation therapy by administering to a patient undergoing such therapy a therapeutically effective amount of a compound according to claims 1, 6 or 10.

* * * * *